(12) United States Patent
Peake et al.

(10) Patent No.: US 11,590,306 B2
(45) Date of Patent: Feb. 28, 2023

(54) TWO-WAY COMMUNICATIONS IN A MEDICAL DEVICE

(71) Applicant: RESMED PTY LTD, Bella Vista (AU)

(72) Inventors: Gregory Robert Peake, Sydney (AU); Timothy Hofler, Escondido, CA (US); Kristina Zlomislic, Sydney (AU); Rowan Furlong, Sydney (AU); Gerard Rummery, Sydney (AU); Nathan Zersee Liu, Sydney (AU); Sakeena De Souza, Sydney (AU); Andrew Weale, San Diego, CA (US); Peter James Dassos, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/551,444

(22) Filed: Dec. 15, 2021

(65) Prior Publication Data
US 2022/0134033 A1    May 5, 2022

Related U.S. Application Data

(63) Continuation of application No. 17/516,372, filed on Nov. 1, 2021.
(Continued)

(51) Int. Cl.
*A61M 16/00* (2006.01)
*G06N 20/00* (2019.01)
(Continued)

(52) U.S. Cl.
CPC ...... *A61M 16/022* (2017.08); *A61M 16/0003* (2014.02); *A61M 16/06* (2013.01);
(Continued)

(58) Field of Classification Search
CPC combination set(s) only.
See application file for complete search history.

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| AU | 2007317446 | 5/2008 |
| AU | 2007317447 | 5/2008 |

(Continued)

OTHER PUBLICATIONS

"*Respiratory Physiology*", by John B. West, Lippincott Williams & Wilkins, $9^{th}$ edition published 2012 (8 pages).
(Continued)

*Primary Examiner* — Margaret M Luarca

(57) ABSTRACT

A respiratory therapy system for providing continuous positive air pressure (CPAP) to a patient may include a flow generator for generating a supply of breathable gas, a sensor to measure a physical quantity while the breathable gas is supplied, and a computing device. The computing device may be configured to: receive sensor data that is based on measured physical property of the supply of breathable gas; control the flow generator to adjust a property of the supply of breathable gas; display a question and a plurality of selectable responses; receive a first input selecting one of the selectable responses; and display a coaching response corresponding to the selected response.

29 Claims, 36 Drawing Sheets

Related U.S. Application Data

(60) Provisional application No. 63/173,978, filed on Apr. 12, 2021, provisional application No. 63/107,794, filed on Oct. 30, 2020.

(51) Int. Cl.
*G16H 10/20* (2018.01)
*A61M 16/06* (2006.01)

(52) U.S. Cl.
CPC ............ *G06N 20/00* (2019.01); *G16H 10/20* (2018.01); *A61M 2205/3553* (2013.01); *A61M 2205/502* (2013.01); *A61M 2205/583* (2013.01)

(56) References Cited

U.S. PATENT DOCUMENTS

| | | |
|---|---|---|
| 6,168,563 B1 | 1/2001 | Brown |
| 6,532,959 B1 | 3/2003 | Berthon-Jones |
| 6,564,797 B1 | 5/2003 | Mechlenburg et al. |
| 6,581,594 B1 | 6/2003 | Drew et al. |
| 6,949,073 B2 | 9/2005 | Sarel |
| 7,051,735 B2 | 5/2006 | Mechlenburg et al. |
| 7,252,636 B2 | 8/2007 | Brown |
| 7,297,119 B2 | 11/2007 | Westbrook et al. |
| 7,310,668 B2 | 12/2007 | Brown |
| 7,516,192 B2 | 4/2009 | Brown |
| 7,533,171 B2 | 5/2009 | Brown |
| 7,717,112 B2 | 5/2010 | Sun et al. |
| 7,866,944 B2 | 1/2011 | Kenyon et al. |
| 7,921,186 B2 | 4/2011 | Brown |
| 7,941,323 B2 | 5/2011 | Brown |
| 8,042,537 B2 | 10/2011 | Mechlenburg et al. |
| 8,060,378 B2 | 11/2011 | Iliff |
| 8,140,663 B2 | 3/2012 | Brown |
| 8,335,992 B2 | 12/2012 | Skidmore et al. |
| 8,548,937 B2 | 10/2013 | Saigal et al. |
| 8,573,209 B2 | 11/2013 | Bathe et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,924,878 B2 | 12/2014 | Palmer et al. |
| 9,076,315 B2 | 7/2015 | Landau et al. |
| 9,119,925 B2 | 9/2015 | Vandine et al. |
| 9,183,720 B2 | 11/2015 | Miladin et al. |
| 9,563,745 B2 | 2/2017 | Saigal et al. |
| 9,788,801 B2 | 10/2017 | Gerder-Kallisch |
| 9,814,850 B2 * | 11/2017 | Paul ................ G16H 80/00 |
| 9,872,965 B2 | 1/2018 | Baloa Welzien et al. |
| 10,115,482 B2 | 10/2018 | Leichner |
| 2003/0213489 A1 | 11/2003 | Mechlenburg et al. |
| 2005/0131273 A1 | 6/2005 | Asano |
| 2007/0000494 A1 | 1/2007 | Banner et al. |
| 2007/0095887 A1 | 5/2007 | Barbosa |
| 2008/0068638 A1 | 3/2008 | Yagi |
| 2008/0114689 A1 | 5/2008 | Psynik et al. |
| 2009/0038616 A1 | 2/2009 | Mulcahy et al. |
| 2009/0044808 A1 | 2/2009 | Guney et al. |
| 2009/0050156 A1 | 2/2009 | Ng et al. |
| 2009/0187121 A1 | 7/2009 | Evans |
| 2009/0205662 A1 * | 8/2009 | Kwok ............... A61M 16/0051 128/204.23 |
| 2009/0293875 A1 | 12/2009 | Kwok |
| 2010/0000534 A1 | 1/2010 | Kooij et al. |
| 2011/0203588 A1 | 8/2011 | Armitstead |
| 2012/0145153 A1 * | 6/2012 | Bassin ............... A61M 16/0069 128/204.23 |
| 2013/0104898 A1 | 5/2013 | Berthon-Jones |
| 2013/0131574 A1 | 5/2013 | Cosentino |
| 2013/0199534 A1 | 8/2013 | Steinhauer et al. |
| 2014/0000604 A1 | 1/2014 | Steinhauer et al. |
| 2015/0154380 A1 | 6/2015 | Duckworth et al. |
| 2016/0071432 A1 | 3/2016 | Kurowski et al. |
| 2016/0193437 A1 | 7/2016 | Bao et al. |
| 2016/0256642 A1 | 9/2016 | Soysa |
| 2016/0270718 A1 | 9/2016 | Heneghan et al. |
| 2016/0275259 A1 | 9/2016 | Nolan et al. |
| 2017/0231528 A1 | 8/2017 | Nathan |
| 2017/0266408 A1 | 9/2017 | Giovannelli et al. |
| 2017/0300652 A1 | 10/2017 | Strobridge |
| 2017/0311879 A1 | 11/2017 | Armitstead |
| 2017/0332906 A1 | 11/2017 | Cribbs et al. |
| 2018/0014777 A1 | 1/2018 | Amir |
| 2018/0015245 A1 | 1/2018 | Frame et al. |
| 2018/0041569 A1 | 2/2018 | Smadja |
| 2018/0092571 A1 | 4/2018 | Wood et al. |
| 2018/0153440 A1 | 6/2018 | Lee et al. |
| 2018/0199882 A1 * | 7/2018 | Klee ................. A61M 16/0683 |
| 2018/0315063 A1 | 11/2018 | Cheesman |
| 2018/0369522 A1 | 12/2018 | Bassin et al. |
| 2019/0000349 A1 | 1/2019 | Narayan et al. |
| 2019/0000350 A1 | 1/2019 | Narayan et al. |
| 2019/0148025 A1 | 5/2019 | Stone |
| 2019/0189258 A1 | 6/2019 | Barrett et al. |
| 2019/0240433 A1 | 8/2019 | Casse et al. |
| 2020/0121873 A1 | 4/2020 | Hudson et al. |
| 2020/0388131 A1 | 12/2020 | Ueda |

FOREIGN PATENT DOCUMENTS

| | | |
|---|---|---|
| AU | 2013244091 | 10/2013 |
| AU | 2018282279 | 1/2019 |
| EP | 1124526 | 8/2001 |
| EP | 2081485 | 7/2009 |
| EP | 2091410 | 8/2009 |
| EP | 2393422 | 12/2011 |
| EP | 2859485 | 4/2015 |
| EP | 3193997 | 7/2017 |
| EP | 3220300 | 9/2017 |
| WO | WO 98/004310 A1 | 2/1998 |
| WO | WO 98/034665 A1 | 8/1998 |
| WO | WO2000018347 | 4/2000 |
| WO | WO 2000/078381 A1 | 12/2000 |
| WO | WO 2004/073778 A1 | 9/2004 |
| WO | WO 2005/063328 A1 | 7/2005 |
| WO | WO2005106758 | 11/2005 |
| WO | WO 2006/074513 A1 | 7/2006 |
| WO | WO 2006/130903 A1 | 12/2006 |
| WO | WO2007145948 | 12/2007 |
| WO | WO2008057951 | 5/2008 |
| WO | WO2008057952 | 5/2008 |
| WO | WO 2009/052560 A1 | 4/2009 |
| WO | WO2010091168 | 8/2010 |
| WO | WO 2010/135785 A1 | 12/2010 |
| WO | WO2012094008 | 7/2012 |
| WO | WO 2012/171072 A1 | 12/2012 |
| WO | WO 2013/020167 A1 | 2/2013 |
| WO | WO2013187776 | 12/2013 |
| WO | WO2015054134 | 4/2015 |
| WO | WO2015062897 | 5/2015 |
| WO | WO2016/019292 | 2/2016 |
| WO | WO2016039950 | 3/2016 |
| WO | WO2016042522 | 3/2016 |
| WO | WO2018001764 | 1/2018 |
| WO | WO2018067637 | 4/2018 |
| WO | WO2018073793 | 4/2018 |
| WO | WO2018106424 | 6/2018 |
| WO | 2018/138675 | 8/2018 |
| WO | WO2019005039 | 1/2019 |
| WO | 2019/163609 | 8/2019 |

OTHER PUBLICATIONS

International Search Report and Written Opinion for PCT/AU2021/051281 dated Feb. 15, 2022.
Written Opinion and International Search Report in International Application No. PCT/IB2020/054641 dated Jul. 15, 2020.
Written Opinion in International Application No. PCT/IB2020/054641 dated May 3, 2021.
European search report issued in EP App. No. 2086392.5 dated Jun. 15, 2022.

(56) References Cited

OTHER PUBLICATIONS

Respironics Philips: "Kurzbedienungsanleitung", May 15, 2016, pp. 1-6.

* cited by examiner

FILTER BY

Therapy adherence

Highly adherent
Trying but struggling
Partially adherent
Not adherent

Feedback: Daytime sleepiness

"Extreme"
"Very High"
"Moderate"
"Slight"
"Not at all"

Feedback: Therapy is

"Challenging"
"Getting there"
"Great!"

Feedback: Failure with

"Mask"
"Device"
"General therapy"

B

FILTER BY

Therapy adherence

Highly adherent
Trying but struggling
Partially adherent
Not adherent

Feedback: Daytime sleepiness

High
Low

Feedback: Therapy difficulty

High
Low

Feedback: Issue with

"Mask"
"Device"
"General therapy"

Company AirView        [Fname Lname] [Logout] ⑦ Help

New patient ⊞    Compliance export 🗔

Patients        Patients   Business   My profile   Administration

˅ Show only...

| User | Location | Status | Notifications | Therapy mode |
|---|---|---|---|---|
| All patients ˅ | All locations ˅ | Active ˅ | -- Select -- ˅ | All modes ˅ |

All therapy
Wireless
Action Groups     [Search patients]
Ventilation patients
Referrals
Patient feedback

[Apply]

| Type | Name | | Available data | Compliant | Last 30 | Last updated |
|---|---|---|---|---|---|---|
| ((•)) | Patient 1 | ⊘ | 00 days | ✓ | 00% | Today |
| ((•)) | Patient 2 | ⊘⚠ | 00 days | ✓ | 00% | Today |
| ((•)) | Patient 4 | (Feedback) | 00 days | ✓ | 00% | Today |

*Company* *AirView*  [Fname Lname] [Logout] ⓘ Help

[New patient] [Card download]

Patients  Business  My profile  Administration

Wireless Patients

| ☐ Name | Initial compliance | Day | Last 30 | 10/9 | 10/10 | 10/11 | 10/12 | 10/13 | 10/14 | 10/15 | 10/16 | 10/17 | 10/18 |
|---|---|---|---|---|---|---|---|---|---|---|---|---|---|
| ☐ Patient 1 | ✗ | 00 | 00% | | | | | | | | ▨ | ▨ | ▨ |
| ☐ Patient 2 | ✗ ⊘ | 00 | 00% | | | | ▨ | ▨ | ▨ | ▨ | ▨ | ▨ | ▨ |
| ☐ Patient 4 | ✗ ⊘△ | 00 | 00% | | ▨ | ▨ | ▨ | ▨ | ▨ | | ▨ | ▨ | ▨ |
| ☐ Patient 3 | ✗ (Feedback) | 00 | 00% | ▨ | ▨ | ▨ | ▨ | ▨ | | | | | |

Received on 00/00 (day 000)

[question to the patient]]?
[[patient response]]

[question to the patient]]?
[[patient response]]

[question to the patient]]?
[[patient response]]

View all feedback

Add note
○ No action
○ Patient contact

[                              ]
350 characters

[Save note]   [Cancel]

*Company* AirView

[Fname Lname] Logout ⓘ Help

Patients   Business   My profile   Administration

| New patient + | Card download | Compliance export |

Patients

∨ Show only...

| User | Location | Status | Notifications | Therapy mode |
|---|---|---|---|---|
| All patients ∨ | All locations ∨ | Active ∨ | -- Select -- ∨ | All modes ∨ |

Apply

Search patients

| Type | Name | Available data | Compliant | Last 30 | Last updated |
|---|---|---|---|---|---|
| 📶 | Patient 1 | ⊘ 00 days | ✓ | 00% | Today |
| 📶 | Patient 2 | ⊘ ⚠ 00 days | ✓ | 00% | Today |
| 📶 | Patient 4 | (Feedback) 00 days | ✓ | 00% | Today |

Received on 00/00 (day 000)

Are you sleepy during the day?
No / A little / A lot

And how is your therapy going?
Challenging / Getting there / Great

Any issue in particular?
Mask / Device / Therapy in general

View all feedback

Add note
◯ No action
◯ Patient contact

[                          ]
350 characters

Save note   Cancel

FIG. 11A

*Company* AirView

[Fname Lname] [Logout] ⊙ Help

Patients   Business   My profile   Administration

[New patient] [Card download]

Wireless Patients

| ☐ Name | Initial compliance | Day | Last 30 | 10/9 | 10/10 | 10/11 | 10/12 | 10/13 | 10/14 | 10/15 | 10/16 | 10/17 | 10/18 |
|---|---|---|---|---|---|---|---|---|---|---|---|---|---|
| ☐ Patient 1 | X | 00 | 00% | | | | | | | ▨ | ▨ | ▨ | ▨ |
| ☐ Patient 2 ⊘ | X | 00 | 00% | | | | | ▨ | ▨ | ▨ | ▨ | ▨ | ▨ |
| ☐ Patient 4 ⊘ △ | X | 00 | 00% | | | ▨ | ▨ | ▨ | ▨ | ▨ | ▨ | ▨ | ▨ |
| ☐ Patient 3 | X | 00 | 00% | ▨ | ▨ | ▨ | ▨ | | | | | | |

(Feedback)

Received on 00/00 (day 000)

Are you sleepy during the day?
No / A little / A lot

And how is your therapy going?
Challenging / Getting there / Great

Any issue in particular?
Mask / Device / Therapy in general

View all feedback

Add note
○ No action
○ Patient contact

[                    ]
350 characters

[Save note]  Cancel

TWO-WAY COMMUNICATIONS IN A MEDICAL DEVICE

1 CROSS-REFERENCE TO RELATED APPLICATIONS

This application is a continuation of U.S. application Ser. No. 17/516,372, filed Nov. 1, 2021, which claims priority to U.S. Provisional Application No. 63/107,794, filed Oct. 30, 2020, and U.S. Provisional Application No. 63/173,978, filed Apr. 12, 2021, the entire contents of which are hereby incorporated by reference.

This application is related to U.S. Provisional Application No. 62/848,991, filed May 16, 2019, and U.S. application Ser. No. 16/875,728, filed May 15, 2020 the entire contents of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use, and more particularly to methods and systems for setting up medical devices and providing tailored coaching and/or personalize therapy for patients using the medical devices.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing. In certain examples, CPAP includes constant Positive Airway Pressure, Automatic Positive Airway Pressure (APAP) therapy, bi-level therapy, and/or other breathing therapies disclosed in this application.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system.

CPAP therapy is highly effective to treat certain respiratory disorders, provided patients comply with therapy. If a mask is uncomfortable, wrongly sized, difficult to use, ill suited to a particular patient characteristic (e.g. a nasal mask for a mouth breather), or difficult to clean (e.g., difficult to assemble or disassemble) a patient may not comply with therapy.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a respiratory pressure therapy system configured to present a patient with demographic and/or subjective questions and receive answers to the questions so that the questions can be analysed to determine settings for the respiratory pressure therapy system.

Another aspect of one form of the present technology is to, e.g., via advanced analytics, determine tailored coaching programs and/or personalized therapy for a patient based on patient's answers to demographic and/or subjective questions and/or data from a plurality of other users.

One form of the present technology comprises applying settings to a respiratory pressure therapy system based on demographic and/or subjective questions answered by a patient.

Another aspect of one form of the present technology is to present demographic and/or subjective questions and receive answers via a web or mobile application.

Another aspect of one form of the present technology is to receive answers for demographic and/or subjective questions via a web or mobile application and using the answers to determine settings for the respiratory pressure therapy system.

Another aspect of one form of the present technology is a processing system including memory storing a plurality of demographic questions and/or a plurality of objective questions and a computing system configured to: transmit demographic and/or objective questions to a medical device and/or a mobile device configured to execute an application for communicating with the medical device, receiving answers to the questions from the medical device and/or the mobile device, determine, e.g., via advanced analytics, based on the received answers, a tailored coaching program for the patient and/or personalised therapy using the medical device An aspect of certain forms of the present technology is a medical device that is easy to use, e.g. by a person who does not have medical training, by a person who has limited dexterity, vision or by a person with limited experience in using this type of medical device.

Another aspect of the present technology is directed to a respiratory therapy system for providing continuous positive air pressure (CPAP) to a patient, the system including a flow generator for generating a supply of breathable gas, a sensor to measure a physical quantity while the breathable gas is supplied, and a computing device. The computing device may be configured to: display a question and a plurality of selectable responses; receive a first input selecting one of the selectable responses; and display a coaching response corresponding to the selected response. The selected response may be transmitted to a remote system and/or the coaching response may be pre-stored.

Another aspect of the present technology is directed to a respiratory pressure therapy (RPT) system for providing continuous positive air pressure (CPAP) to a patient. The system comprising: a flow generator configured to generate a supply of breathable gas for delivery to the patient, wherein the breathable gas is output from the flow generator at a pressure level that is above atmospheric pressure; at least one sensor that is configured to measure a physical quantity while the breathable gas is supplied to the patient; a computing device including memory and at least one hardware processor. The computing device may be configured to: receive, from the at least one sensor, sensor data that is based on measured physical property of the supply of breathable gas; control, based on the received sensor data, the flow generator to adjust a property of the supply of breathable gas that is delivered to the patient; display, on a display device, one or more questions relating to demographic and/or subjective feedback; responsive to displaying the one or more questions, receive one or more inputs indicating answers to the one or more questions; transmit the answers to a remote processing system; receive, from the remote processing system, settings for the respiratory pressure therapy system determined based on the transmitted answers; and adjust, based on the received settings, control settings of the respiratory pressure therapy system.

In examples, (a) the remote processing system may be an on-demand cloud computing platform configured to perform machine learning using data received from a plurality of patients, (b) the questions may be pre-stored in the memory, (c) the computing device may be further configured to perform setup operations, and the one or more questions may be displayed after the setup and after a predetermined condition is satisfied, (d) the predetermined condition may include a predetermined amount of time passing after setup, (e) the questions may include at least one question relating to demographic information about the patient and at least one question relating to subjective feedback from the patient about using the respiratory pressure therapy system, (f) the system may further include the remote processing system and the remote processing system may be configured to determine tailored coaching programs for the patient based on the answers transmitted to the remote processing system, (g) the system may further include the remote processing system and the remote processing system may be configured to determine personalized therapy for the patient based on the answers transmitted to the remote processing system, (h) the one or more questions may be received from the remote processing system, (i) the system may further include a patient interface configured to engage with at least one airway of the patient and supply breathable gas to the patient, and/or (j) the settings for the respiratory pressure therapy system and/or tailored coaching programs are received by an application, website, email, and/or mobile device associated with the patient.

Another aspect of the present technology is directed to an apparatus for treating a respiratory disorder in a patient. The apparatus comprising: a display device; a pressure generator configured to generate a flow of air for treating the respiratory disorder; a transducer configured to generate a flow signal representing a property of the flow of air; a controller, coupled to the display, the pressure generator, and the transducer. The controller may be configured to: receive the flow signal from the transducer; based on the received flow signal, control the pressure generator to adjust a property of the flow of air; display, to the display device, a request for demographic and/or subjective feedback; responsive to the request, receive one or more inputs representing demographic and/or subjective feedback; transmit demographic and/or subjective feedback data determined based on the received one or more inputs to a remote processing system; receive, from the remote processing system, analysis results determined based on the transmitted demographic and/or subjective feedback data; and adjust, based on the received analysis results, control settings of the apparatus.

In examples, (a) the controller, the display, and the pressure generator may be commonly housed, (b) the adjusted control settings may include a treatment pressure provided in a patient mask coupled to the pressure generator, (c) the analysis results may include tailored coaching programs for the patient, (d) the analysis results may include a personalized therapy for the patient, (e) the controller may be configured to transmit, with the demographic and/or subjective feedback data, operational data of the apparatus, and the analysis results may be determined based on the demographic and/or subjective feedback data and the operational data of the apparatus, (f) the request for demographic and/or subjective feedback may be displayed after a predetermined condition is satisfied, (g) the predetermined condition may be a predetermined time period after the apparatus is set up, and/or (h) the predetermined condition may be a predetermined time period that the apparatus has been operated by the patient.

Another aspect of the present technology is directed to a method of operating a respiratory treatment apparatus for generating a flow of air in order to treat a respiratory disorder. The method comprises: measuring a property of the flow of air, using a transducer; calculating, in a controller and based on the measured property, a result comprising at least one of: a respiratory event, a cardio-respiratory characteristic of a patient, and a physiological state of the patient; controlling, in the controller, an adjustment to a property of the flow of air based on the result; displaying one or more questions relating to demographic and/or subjective feedback; responsive to displaying the one or more questions, receiving, in the controller, one or more inputs indicating answers to the one or more questions; transmitting the answers to a remote processing system; and receiving, from the remote processing system, settings for operating the respiratory treatment apparatus and/or tailored coaching programs for the patient based on the answers transmitted to the remote processing system.

In examples, (a) the method may include adjusting, based on the received settings, control settings of the respiratory treatment apparatus, (b) the settings for operating the respiratory treatment apparatus may provide personalized therapy for the patient determined based on the answers transmitted to the remote processing system and control settings of the respiratory treatment apparatus at a time the inputs indicating answers are received, (c) the questions may be displayed on a display of the respiratory treatment apparatus, (d) the questions may be displayed on a mobile device configured to execute an application for controlling the respiratory treatment apparatus, (e) the questions may be displayed after a predetermined condition is satisfied, (f) the predetermined condition may be a predetermined time period after the respiratory treatment apparatus is set up, and/or (g) the predetermined condition may be a predetermined time period that the respiratory treatment apparatus has been operated by the patient.

Another aspect of the present technology is directed to a processing system comprising: memory storing a plurality of demographic questions and a plurality of objective questions; a computing system including at least one hardware processor coupled to the memory, the computing system configured to: transmit, to a medical device associated with a patient, at least one demographic question and at least one objective question stored in the memory; receive, from the medical device, answers to the at least one demographic question and at least one objective question transmitted to the medical device; transmit, to a mobile device configured to execute an application for communicating with the medical device, a notification indicating that unanswered questions are available; receive, from the mobile device, request for the questions; responsive to the request, transmit, to the mobile device, at least one demographic question and at least one objective question stored in the memory; receive, from the mobile device, answers to the at least one demographic question and at least one objective question transmitted to the mobile device; and perform advanced analytics to determine, based on (1) the answers received from the medical device and the mobile device and (2) answers received from a plurality of other medical devices, a tailored coaching program for the patient and personalised therapy using the medical device.

In examples, (a) the computing system may be further configured to receive, from the medical device, answers to questions pre-stored on the medical device and answered using the medical device, (b) the medical device may be a respiratory treatment apparatus, (c) the questions may be transmitted to the mobile device and/or the medical device after a predetermined condition is satisfied, (d) the predetermined condition may be a predetermined time period after the medical device is setup, and/or (e) the predetermined condition may be a predetermined time period that the medical device has been operated by the patient. The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Another aspect of the present technology is directed to a respiratory therapy system for providing continuous positive air pressure (CPAP) to a patient, the system including a flow generator for generating a supply of breathable gas, a sensor to measure a physical quantity while the breathable gas is supplied, and a computing device. The computing device may be configured to: receive sensor data that is based on measured physical property of the supply of breathable gas; control the flow generator to adjust a property of the supply of breathable gas; display a question and a plurality of selectable responses; receive a first input selecting one of the selectable responses; display a coaching response corresponding to the selected response; transmit the selected response to a remote system in response to receiving a second input to continue; receive, from the remote system, settings for the respiratory therapy system; and adjust, based on the received settings, control settings of the respiratory therapy system.

Another aspect of the present technology is directed to a respiratory pressure therapy system for providing continuous positive air pressure (CPAP) to a patient, the respiratory pressure therapy system comprising: a flow generator configured to generate supply of breathable gas for delivery to the patient, wherein the breathable gas is output from the flow generator at a pressure level that is above atmospheric pressure; at least one sensor that is configured to measure a physical quantity while the breathable gas is supplied to the patient; a computing device including memory and at least one hardware processor, the computing device configured to control the respiratory pressure therapy system to: receive, from the at least one sensor, sensor data that is based on measured physical property of the supply of breathable gas; control, based on the received sensor data, the flow generator to adjust a property of the supply of breathable gas that is delivered to the patient; display, on a display device, a first question relating to demographic and/or subjective feedback and a plurality of selectable responses to the first question; responsive to displaying the first question, receive a first input selecting one of the selectable responses to the first question; and in response to receiving the first input, display a first coaching response corresponding to the selected response to the first question.

In examples, (a) a plurality of coaching responses corresponding to the plurality of selectable responses are stored in the memory; (b) a plurality of coaching responses corresponding to the plurality of selectable responses are received from remote processing system; (c) the first coaching response includes insights and/or encouragement to a user of the respiratory pressure therapy system; (d) the computing device is further configured to control the respiratory pressure therapy system to: display a second coaching response corresponding to the selected response to the first question in response to receiving the second input to continue; (e) displaying the second coaching response includes displaying a plurality of selectable options, each of the selectable options corresponding to resolving a different issue in using the respiratory pressure therapy system; (f) the plurality of selectable options include using an application associated with the respiratory pressure therapy system to guide a user of the respiratory pressure therapy system in resolving the issue in using the respiratory pressure therapy system; (g) the computing device is further configured to control the respiratory pressure therapy system to: display, after receiving the second input to continue, a second question relating to demographic and/or subjective feedback and a plurality of selectable responses to the second question; responsive to displaying the second question, receive a third input selecting one of the selectable responses to the second question; display a third coaching response corresponding to the selected response to the second question in response to receiving the third input to continue; and after displaying the third coaching response, transmit the selected response to the second question to the remote processing system in response to receiving a fourth input to continue; (h) the first question is related to how well therapy provided by the respiratory pressure therapy system is going for a user of the respiratory pressure therapy system; (i) the first question and the plurality of selectable responses to the first question are displayed at predetermined intervals of time; (j) the first question and the plurality of selectable responses to the first question are displayed to a user of the respiratory pressure therapy system when the respiratory pressure therapy system is first used by the user; (k) the first question and the plurality of selectable responses to the first question are displayed to a user of the respiratory pressure therapy system on predetermined days from when the user started using the respiratory pressure therapy system; (l) the computing device is further configured to control the respiratory pressure therapy system to: receive, from a system associated with a clinician, additional settings for the respiratory pressure therapy system determined based on the transmitted response to the first question; (m) the system associated with the clinician is an on-demand cloud computing platform configured to perform machine learning using data received from a plurality of patients; (n) the respiratory pressure therapy system further comprising the system associated with the clinician and the system associated with the clinician is configured to determine tailored coaching programs for the patient based on responses to questions transmitted to the remote processing system from the computing device; (o) the respiratory pressure therapy system further comprising the system associated with the clinician and the system associated with the clinician is configured to determine personalized therapy for the patient based on responses to questions transmitted to the remote processing system from the computing device; (p) the respiratory pressure therapy system further comprising a patient interface configured to engage with at least one airway of the patient and supply breathable gas to the patient; (q) the first question includes a question relating to subjective feedback from the patient about using the respiratory pressure therapy system; (r) the respiratory pressure therapy system further comprising the remote processing system and the remote processing system is configured to determine tailored coaching programs for the patient based on responses to questions transmitted to the remote processing system from the computing device; (s) the settings and additional settings for the respiratory pressure therapy system and/or tailored coaching programs are received by an application, website, email, and/or a mobile device associated with the patient; and/or (t) the computing device is further configured to control the respiratory pressure therapy system to: after displaying the first coaching response, transmit the selected response to the first question to a remote processing system in response to receiving a second input to continue; receive, from the remote processing system, settings for the respiratory pressure therapy system; and adjust, based on the received settings, control settings of the respiratory pressure therapy system.

Another aspect of the present technology is directed to a method for providing continuous positive air pressure (CPAP) to a patient. The method comprising: receiving, from at least one sensor configured to measure a physical quantity while breathable gas is supplied to the patient, sensor data that is based on measured physical property of the supply of breathable gas; controlling, based on the received sensor data, the flow generator to adjust a property of the supply of breathable gas that is delivered to the patient; displaying, on a display device, a first question relating to demographic and/or subjective feedback and a plurality of selectable responses to the first question; responsive to displaying the first question, receiving a first input selecting one of the selectable responses to the first question; in response to receiving the first input, displaying a first coaching response corresponding to the selected response to the first question; after displaying the first coaching response, transmitting the selected response to the first question to a remote processing system in response to receiving a second input to continue; receiving, from the remote processing system, settings for the respiratory pressure therapy system; and adjusting, based on the received settings, control settings of the respiratory pressure therapy system.

Another aspect of the present technology is directed to an apparatus for treating a respiratory disorder in a patient, the apparatus comprising: a display; a pressure generator configured to generate a flow of air for treating the respiratory disorder; a transducer configured to generate a flow signal representing a property of the flow of air; a controller, coupled to the display, the pressure generator, and the transducer. The controller may be configured to: receive the flow signal from the transducer; based on the received flow signal, control the pressure generator to adjust a property of the flow of air; control the display to display a first question relating to subjective feedback and a plurality of selectable responses to the first question; responsive to displaying the first question, receive a first input selecting one of the selectable responses to the first question; after receiving the first input, display a first coaching response corresponding to the selected response to the first question and transmit information about the selected response to the first question to a remote processing system.

In examples, (a) the controller is further configured to: receive, from the remote processing system, analysis results determined based on the transmitted response to the first question; and adjust, based on the received analysis results, control settings of the apparatus; (b) the controller is configured to transmit operational data of the apparatus to the remote processing system, and the analysis results are determined based on the demographic and/or subjective feedback data and the operational data of the apparatus; (c) the analysis results include tailored coaching program for the patient; (d) the controller is further configured to receive, from the remote processing system questions for the patient and a plurality of selectable responses for each question; (e) the further coaching responses include instructions for using the apparatus; (f) the further coaching responses include a personalized therapy for the patient; and/or (g) the controller is further configured to: receive, from the remote processing system, further coaching responses; and control the display to display the further coaching responses.

Another aspect of the present technology is directed to a method for treating a respiratory disorder in a patient. The method comprising: receiving a flow signal from a transducer configured to generate a flow signal representing a property of the flow of air; based on the received flow signal, controlling a pressure generator to adjust a property of the flow of air; controlling a display to display a first question relating to subjective feedback and a plurality of selectable responses to the first question; responsive to displaying the first question, receiving a first input selecting one of the selectable responses to the first question; after receiving the first input, displaying a first coaching response corresponding to the selected response to the first question and transmitting information about the selected response to the first question to a remote processing system; receiving, from the remote processing system, further coaching responses; and controlling the display to display the further coaching responses.

Another aspect of the present technology is directed to a home medical equipment managing system comprising: communication circuitry configured to communicate with a plurality of respiratory pressure therapy devices and other devices executing applications associated with the plurality of respiratory pressure therapy devices; and a processing system including memory and at least one hardware processor coupled to the communication circuitry, the processing system configured to: receive, from each of the plurality of respiratory pressure therapy devices and the applications executing on the other devices, patient information, respiratory pressure therapy device use history and responses to questions; output a user interface including a list of patients associated with the plurality of respiratory pressure therapy devices and the applications executing on the other devices, and selectable filters for filtering patients displayed in the list; in response to selecting one or more filters, display a filtered list of patients satisfying the selected filters; and in response to receiving a selection of a patient in the list of patients or filtered lists, output information about use of the respiratory pressure therapy devices by the selected patient.

In examples, (a) the processing system is further configured to: in response to receiving the selection of the patient in the list of patients or filtered lists, output information about questions displayed to the selected patient via the respiratory pressure therapy devices or the applications executing on the other devices and subjective feedback entered by the patient in response to the questions; (b) the selectable filters include a plurality of filter groups, each filter group including a plurality of selectable filters; (c) each filter group corresponds to feedback received from the respiratory pressure therapy devices or the applications executing on the other devices in response to questions presented to the patients associated with the respiratory pressure therapy devices or the applications executing on the other devices; (d) each selectable filter in at least one of the plurality of filter groups corresponds to a different characteristic assignable to a patient based on the received feedback from the patient; (e) multiple selectable filter in at least one of the plurality of filter groups corresponds to a same characteristic assignable to a patient based on the received feedback from the patient; (f) the processing system is further configured to: receive subjective feedback entered by patients in response to questions presented to the patients from the respiratory pressure therapy devices and/or the applications executing on the other devices; and transmit to the respiratory pressure therapy devices therapy setting determined based on the subject feedback received from the corresponding respiratory pressure therapy device or the corresponding application associated with the corresponding respiratory pressure therapy device.

Another aspect of the present technology is directed to a method for managing home medical equipment. The method comprising receiving, from each of a plurality of respiratory pressure therapy devices and applications executing on other devices, patient information, respiratory pressure therapy device use history and responses to questions; outputting a user interface including a list of patients associated with the plurality of respiratory pressure therapy devices and the applications executing on the other devices, and selectable filters for filtering patients displayed in the list; in response to selecting one or more filters, displaying a filtered list of patients satisfying the selected filters; and in response to receiving a selection of a patient in the list of patients or filtered lists, outputting information about use of the respiratory pressure therapy devices by the selected patient.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1 shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 2 shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 3 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.3 Humidifier

Figure 5A:
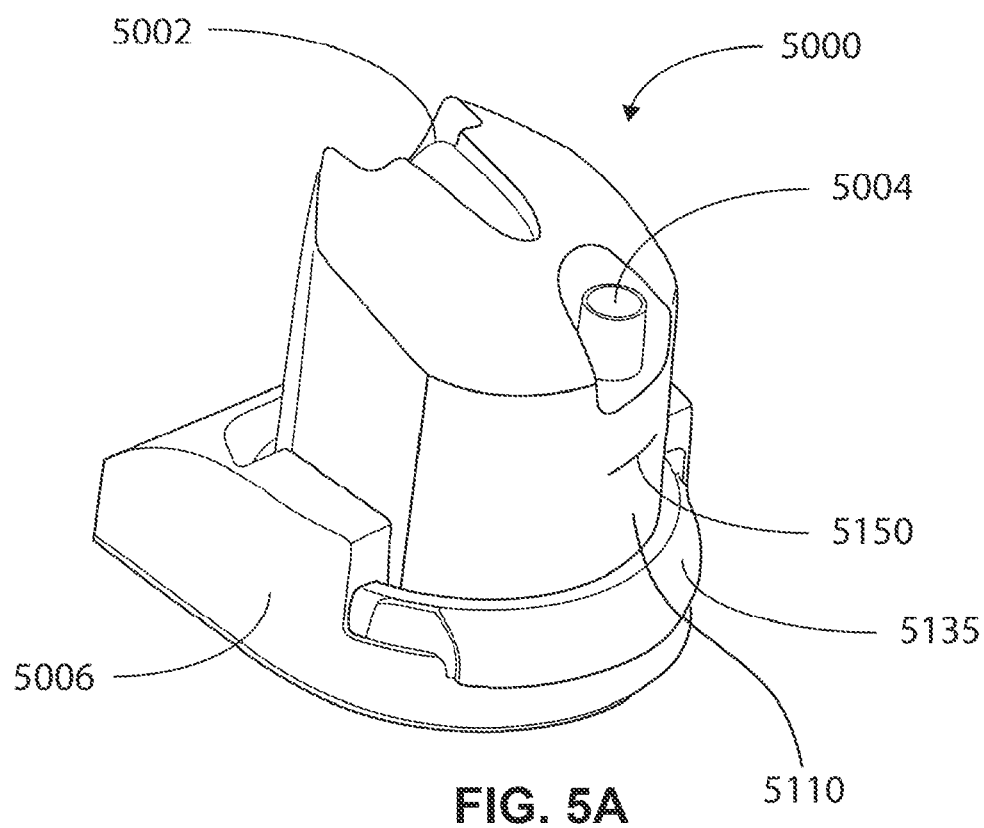

FIG. 5A shows an isometric view of a humidifier in accordance with one form of the present technology.

Figure 5B:
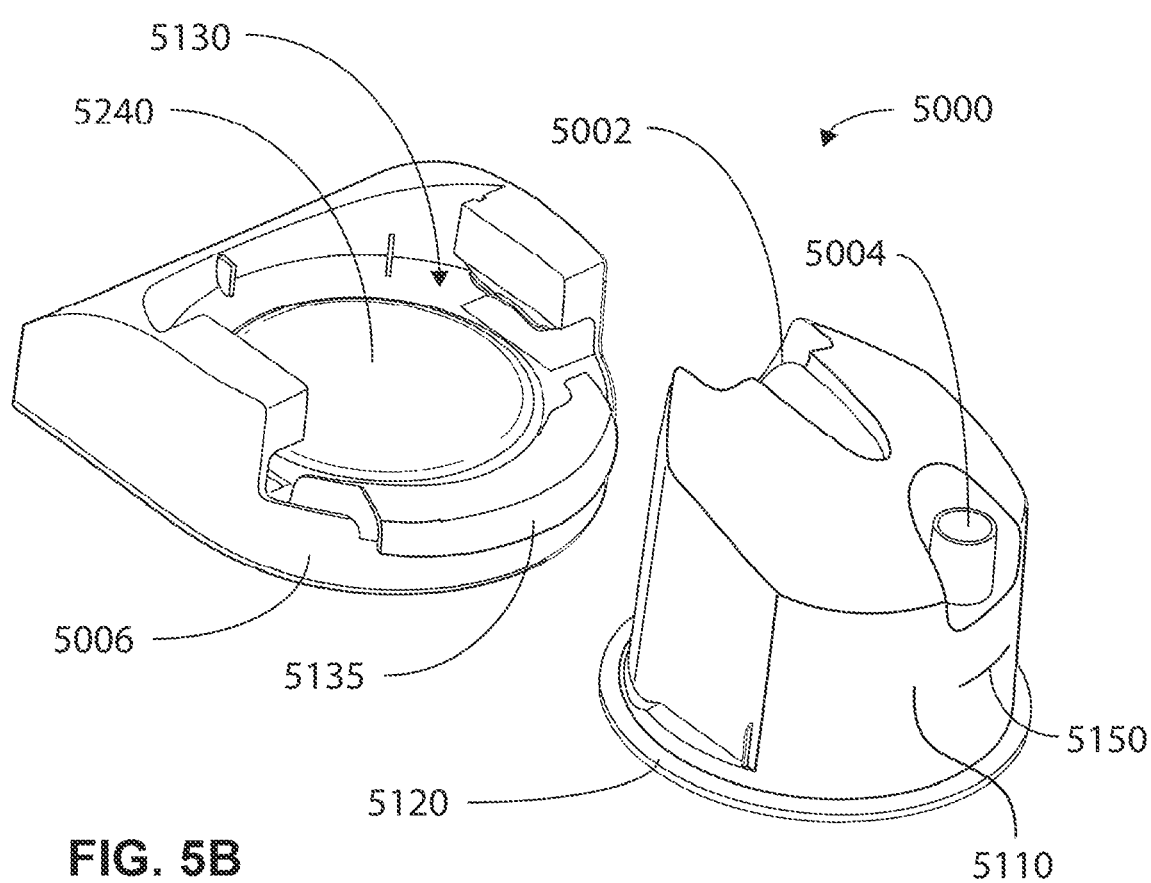

FIG. 5B shows an isometric view of a humidifier in accordance with one form of the present technology, showing a humidifier reservoir 5110 removed from the humidifier reservoir dock 5130.

Figure 5C:
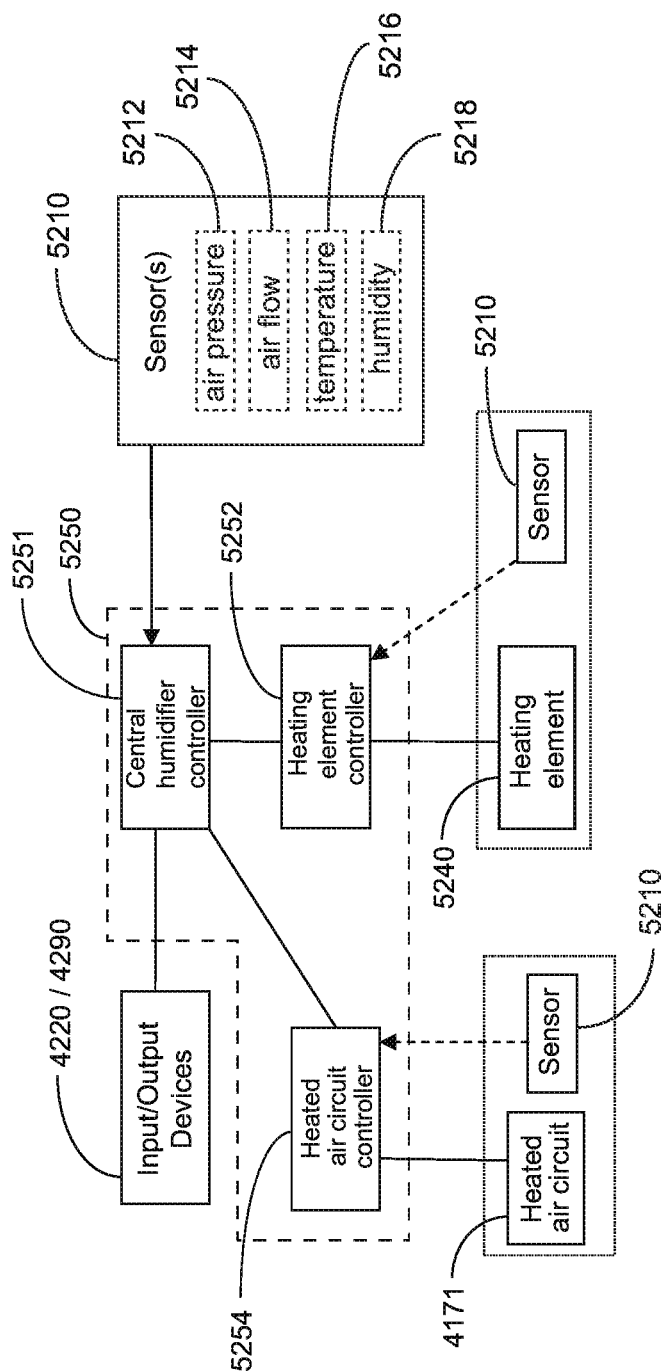

FIG. 5C shows a schematic of a humidifier in accordance with one form of the present technology.

Figure 6:
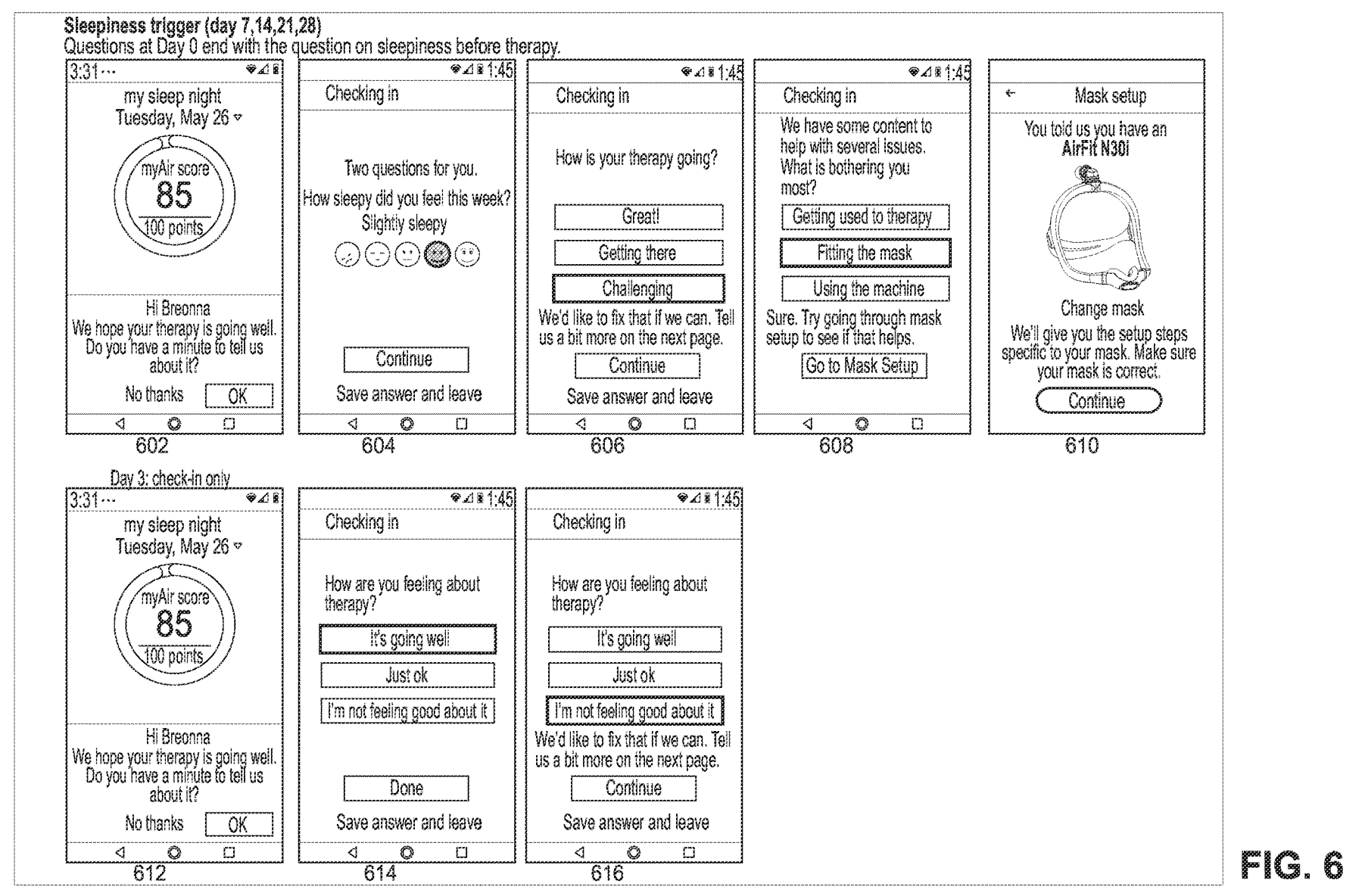

FIG. 6 shows a user interface that may be provided in an application executed on a device in accordance with one form of the present technology.

Figure 7A:
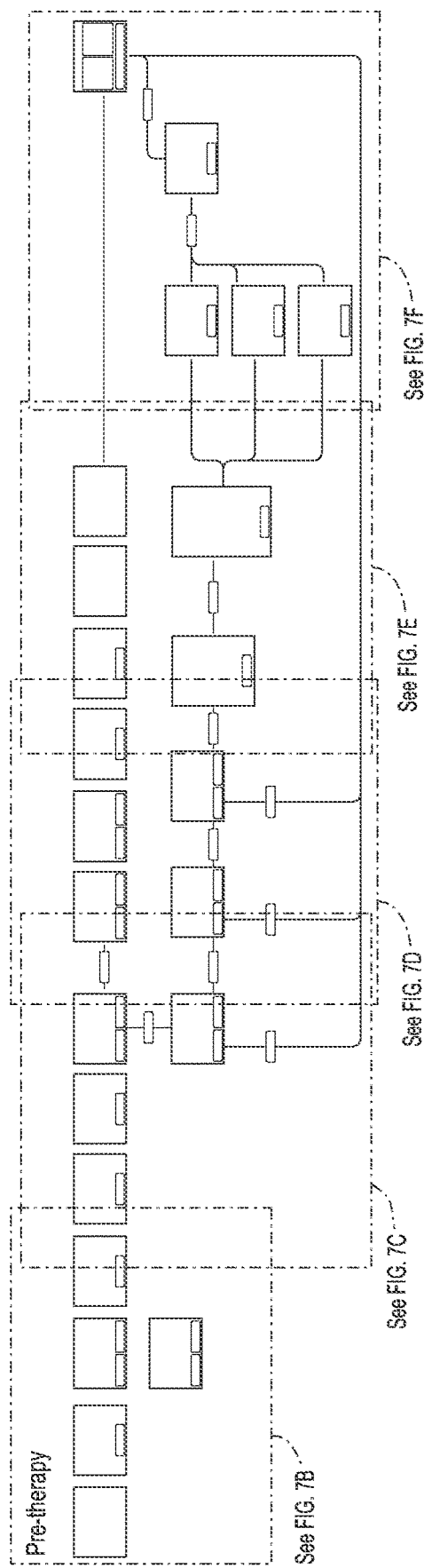

FIG. 7A illustrates an overview of pre-therapy flow and questions to be provided in the medical device and/or outside of the medical device in accordance with one form of the present technology.

FIGS. 7B-7F illustrate detailed views of the flow and questions shown in FIG. 7A.

Figure 8A:
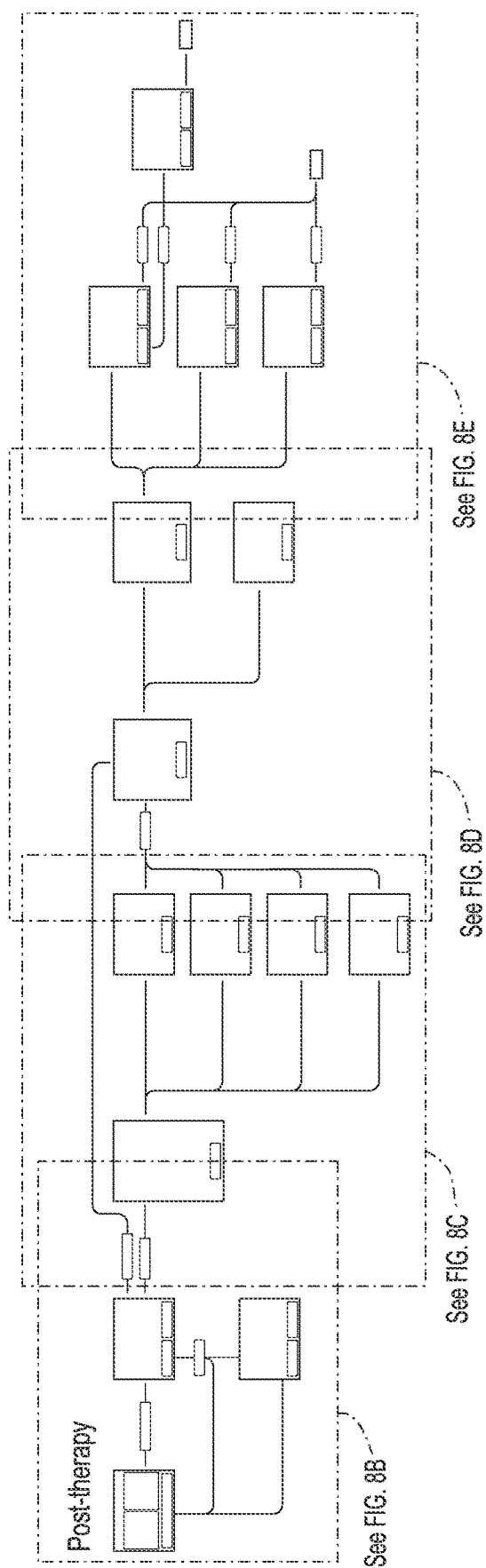

FIG. 8A illustrates an overview of post-therapy flow and questions to be provided in the medical device and/or outside of the medical device in accordance with one form of the present technology.

FIGS. 8B-8E illustrate detailed views of the flow and questions shown in FIG. 8A.

Figure 9A:
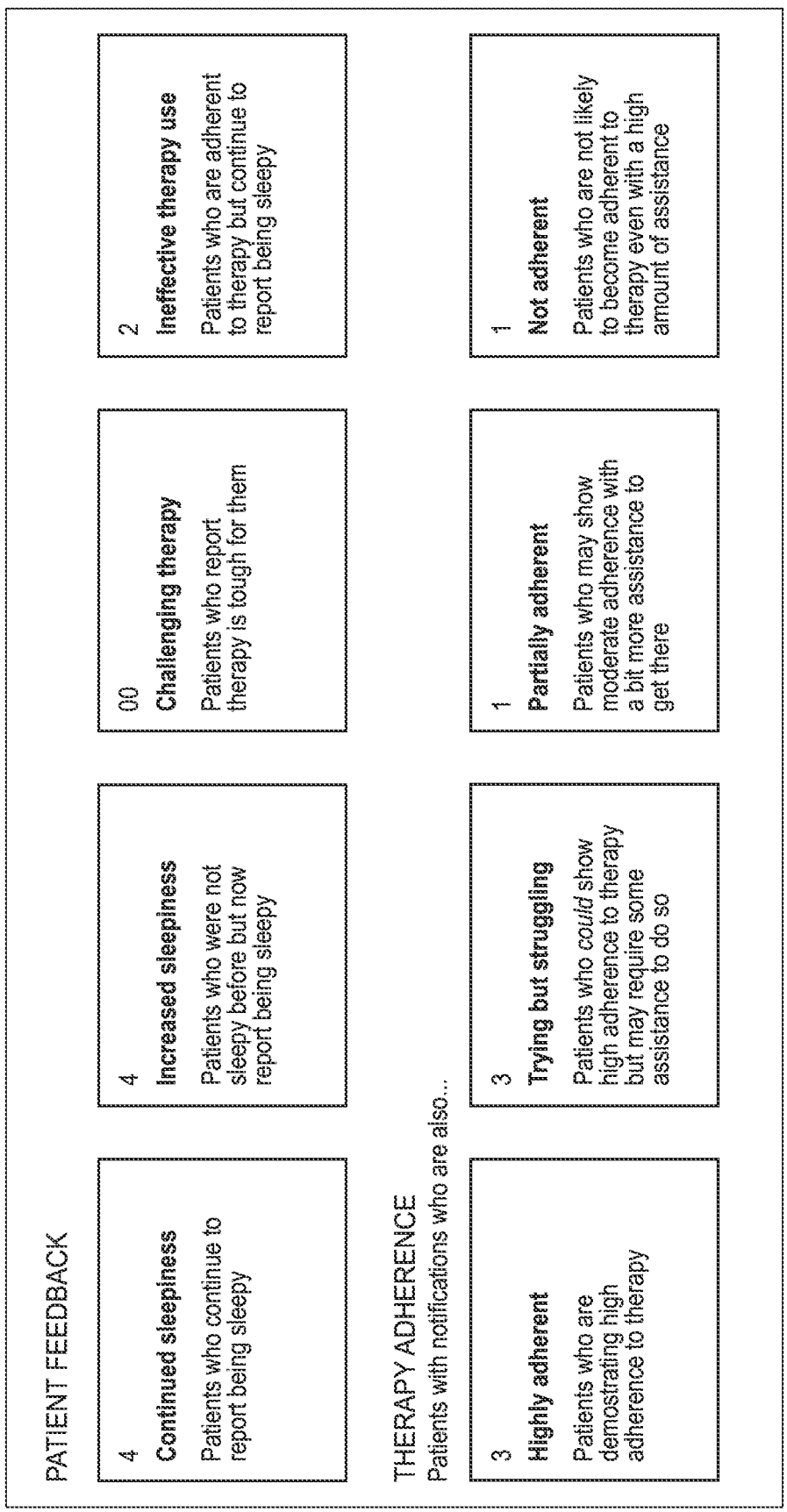

FIG. 9A shows an example home view of patient groups/buckets in accordance with one form of the present technology.

Figure 9B:

FIG. 9B illustrates an example of a sleep concierge patient's exception management in accordance with one form of the present technology.

Figure 9C:

FIG. 9C illustrates an example of a patient detail panel in accordance with one form of the present technology.

FIG. 9D illustrates an example of Red/Green Thumbs logic for the filtering options in accordance with one form of the present technology.

FIG. 10A illustrate an example of an interface providing information about a plurality of patients in accordance with one form of the present technology.

FIG. 10B illustrates another example of an interface providing information about a plurality of patients in accordance with one form of the present technology.

FIG. 11A illustrates another example of an interface providing information about a plurality of patients in accordance with one form of the present technology.

FIG. 11B illustrates another example of an interface providing information about a plurality of patients in accordance with one form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises one or more of the following functional aspects: a seal-forming structure, a plenum chamber, a positioning and stabilising structure, a vent, one form of connection port for connection to air circuit 4170, and a forehead support. In some forms a functional aspect may be provided by one or more physical components. In some forms, one physical component may provide one or more functional aspects. In use the seal-forming structure is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 4 cmH$_2$O with respect to ambient, at least 6 cmH$_2$O with respect to ambient, at least 10 cmH$_2$O with respect to ambient, at least 20 cmH$_2$O with respect to ambient, at least 30 cmH$_2$O with respect to ambient or any positive pressure between 4 cmH$_2$O and 30 cmH$_2$O with respect to ambient.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142 including a motor 4144), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

An RPT device may comprise one or more of the following components in an integral unit. In an alternative form, one or more of the following components may be located as respective separate units. For example, the RPT device may comprise one or more of an air filter 4110, side panel, muffler (e.g., muffler 4120, inlet muffler 4122, outlet muffler 4124), pressure generator, pneumatic block, chassis, transducer 4270 (flow transducer, pressure transducer, motor speed transducer), light sensor, anti-spillback valve 4160, air circuit, air circuit connector, oxygen delivery port, power supply, central controller, therapy device controller, protection circuit, data connection interface, memory, output devices (e.g. display, alarms, etc. . . . ) and a user interface panel(s), such as those described in PCT application PCT/AU2014/050426 (WO2015089582), which is incorporated herein by reference.

According to one example, the user interface panel includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.1.1 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fiber) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.1.2 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.1.2.1 Display Driver

A display driver 4292 receives as an input the characters, symbols, or images intended for display on the display 4294, and converts them to commands that cause the display 4294 to display those characters, symbols, or images.

5.4.1.2.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules. The modules may include a pre-processing module 4310 providing pressure compensation 4312, vent flow rate estimation 4314, leak flow rate estimation 4316, and respiratory flow rate estimation 4318. The processing of the pre-processing module 4310 may be used as an input into a therapy engine module 4320. The therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329. A therapy control module 4330 receives as inputs the therapy parameters from the therapy parameter determination algorithm 4329 of the therapy engine module 4320, and controls the pressure generator 4140 to deliver a flow of air in accordance with the therapy parameters. In one form of the present technology, the central controller 4230 executes one or more methods 4340 for the detection of fault conditions. Details regarding one or more operations performed by algorithms are described in the PCT application PCT/AU2014/050426 (WO2015089582), which is incorporated herein by reference.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.6 Two-Way Communication for Personalised Therapy and/or Coaching

In one form of the present technology, a medical device (e.g., a RPT device) may include two-way communication with one or more remote processing system to facilitate tailored coaching programs, personalized therapy, and/or targeted care. The medical device may be configured to capture data and/or transmit the data to the remote processing system for processing. The captured data may include, sensor data, demographic feedback, and/or subjective feedback. The remote processing system may perform patient segmentation and/or advanced analytics using the received data and provide the medical device with tailored solutions. The tailored solutions may include tailored coaching programs for increased engagement and motivation, personalized therapy with automated comfort and/or therapy setting updates to increase long term adherence, and/or targeted care and follow up based on knowing which patients need help. The patient segmentation and advanced analytics may include performing machine deep learning using data from other users and using one or more trained models to provide the tailored solutions.

Unlike conventional systems in which settings for a medical device had to be pre-loaded and were modified by a highly trained technician, examples of the present technology provide for the medical device to be configured automatically after the device is deployed for use. The settings for the medical device and recommendations for the patient can be accurately determined remotely and quickly without needing a clinician to perform multiple iterations of modifying the device settings before a patient feels comfortable when using the medical device. In addition, the feedback received from the user and settings of the medical device can be used to improve settings of other medical devices and provide relevant recommendations to other patients.

Figure 1:
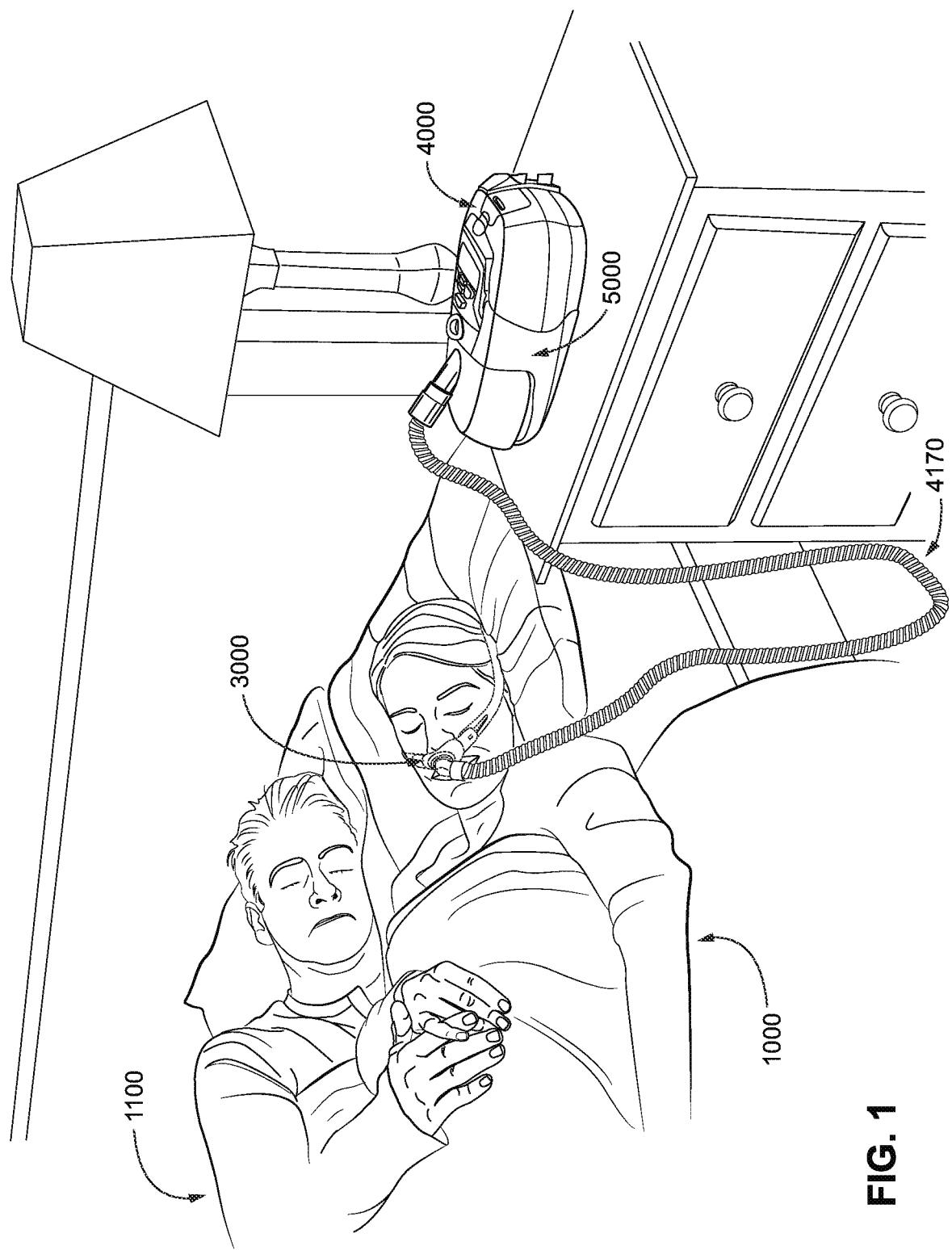
Figure 2:
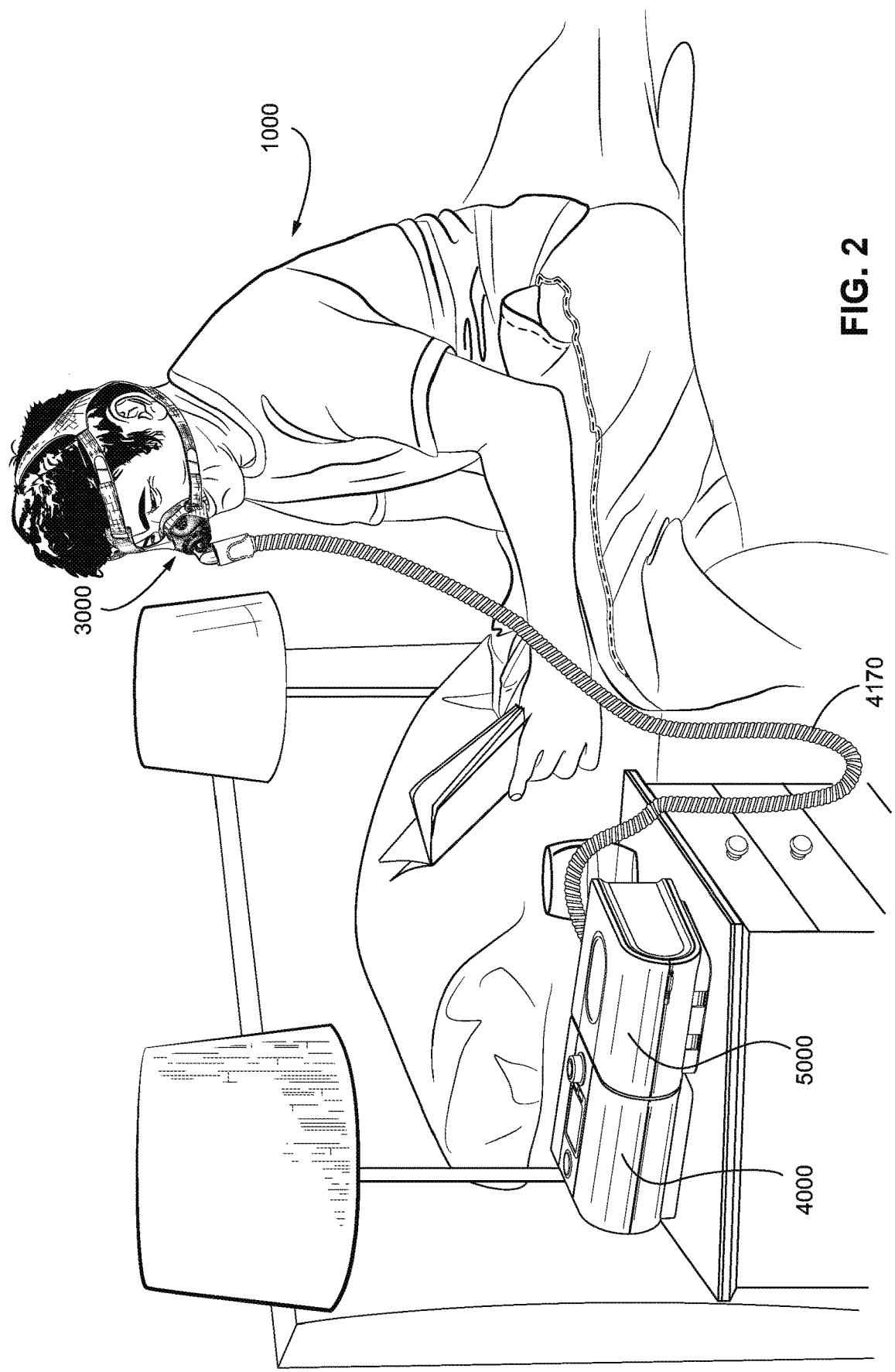
Figure 3:
Figure 4A:
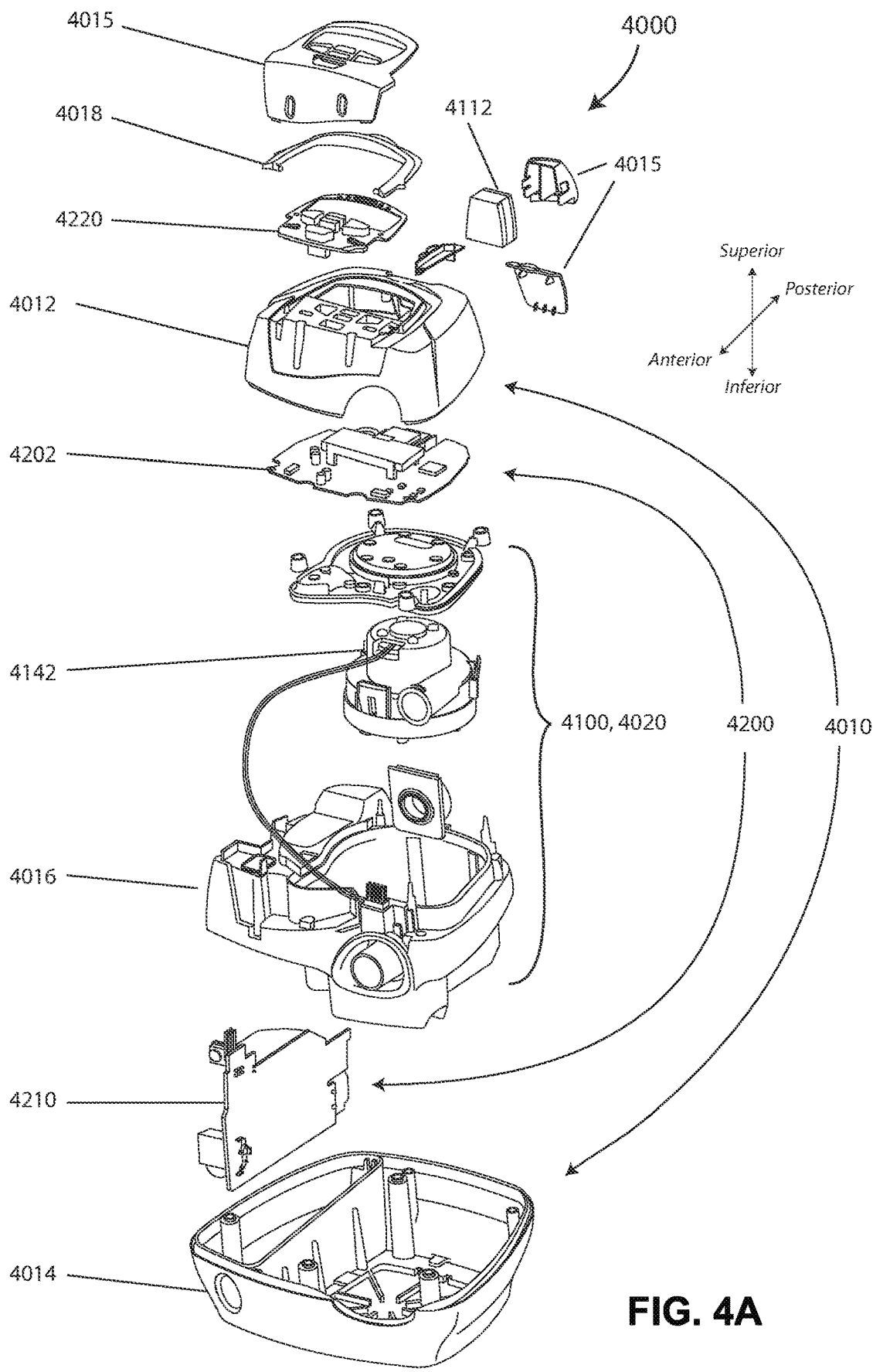
FIG. 4C is a schematic diagram of the electrical components of an RPT device in accordance with one form of the present technology.
FIG. 4D is a schematic diagram of the electrical components of an RPT device in accordance with one form of the present technology.
FIG. 4E is a schematic diagram of the algorithms implemented in an RPT device in accordance with one form of the present technology.
FIG. 4F is a flow chart illustrating a method carried out by the therapy engine module of FIG. 4E in accordance with one form of the present technology.
FIG. 4G shows a diagram of a communication system between an RPT device and a remote computing system in accordance with one form of the present technology.
FIG. 4H shows exemplary operations performed by an RPT device and a remote computing system in accordance with one form of the present technology.
FIG. 4I shows example display screens including demographic and/or subjective feedback requests that may be displayed to a patient in accordance with one form of the present technology.
FIG. 4J shows another example of operations performed by an RPT device and a remote computing system in accordance with one form of the present technology.
FIG. 4K shows a data flow diagram in a system providing communication between a medical device, a patient portal 8030 and a patient survey service 8010 in accordance with one form of the present technology.
Figure 4B:
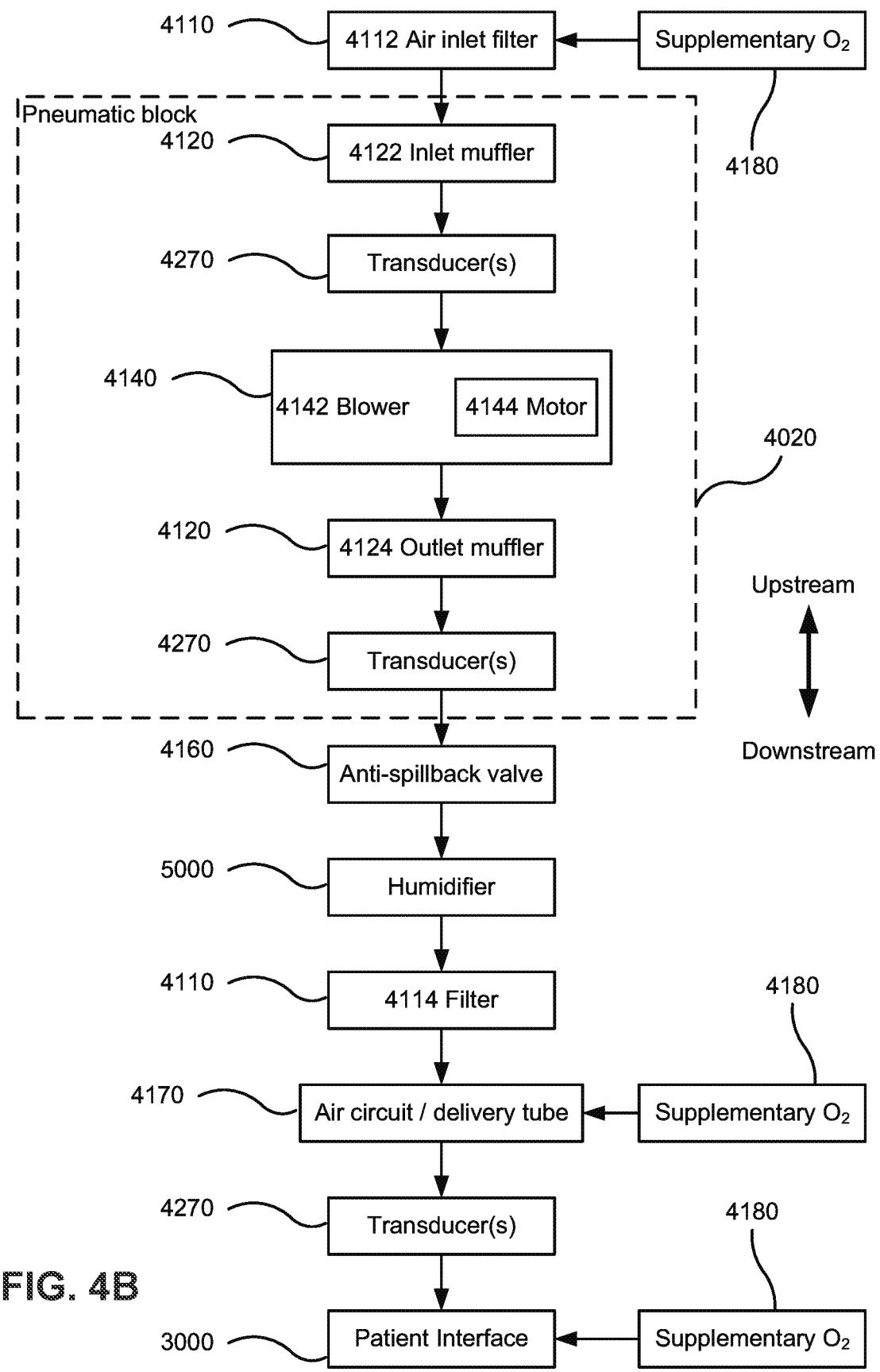
Figure 4C:
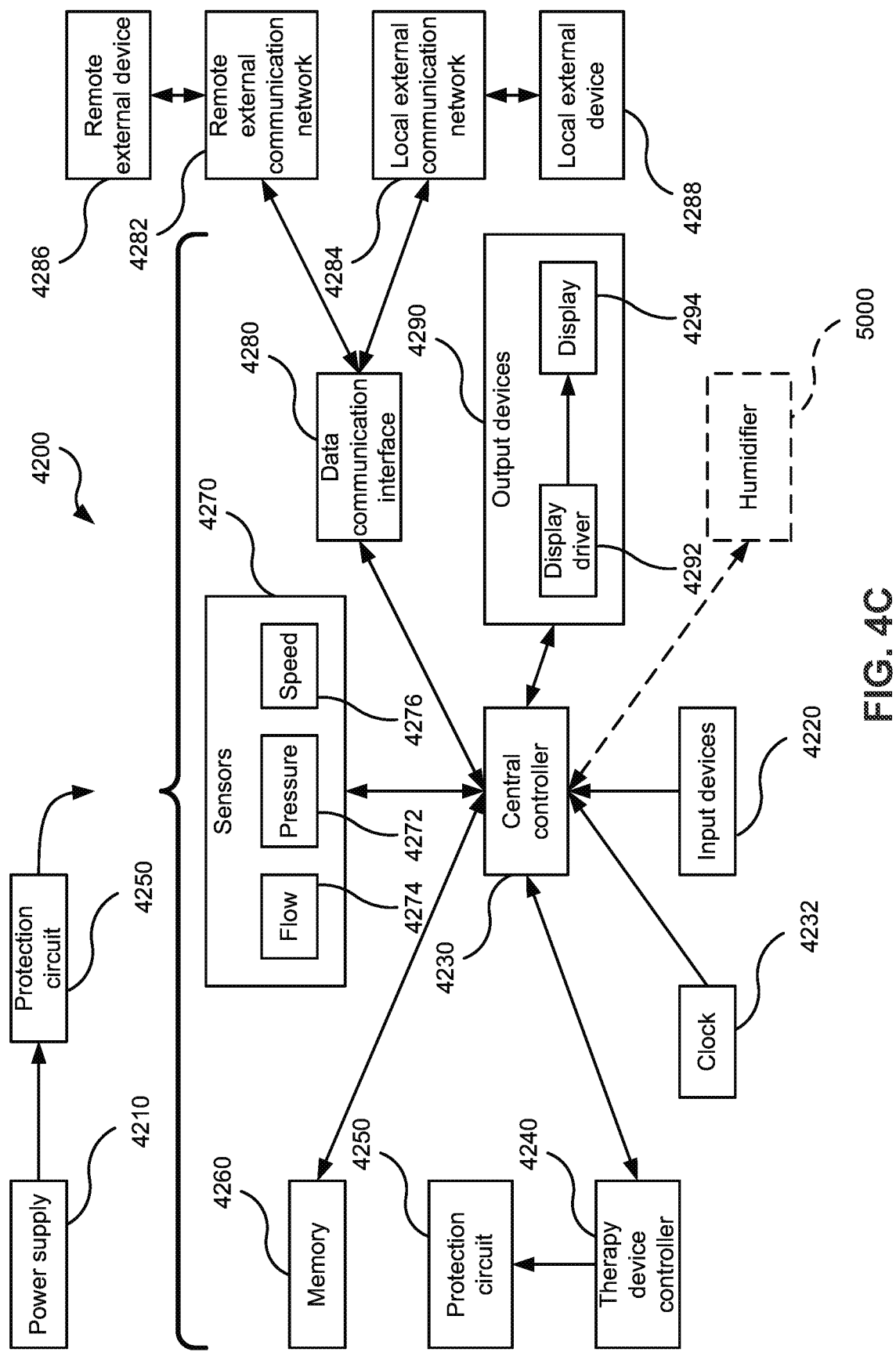
Figure 4D:
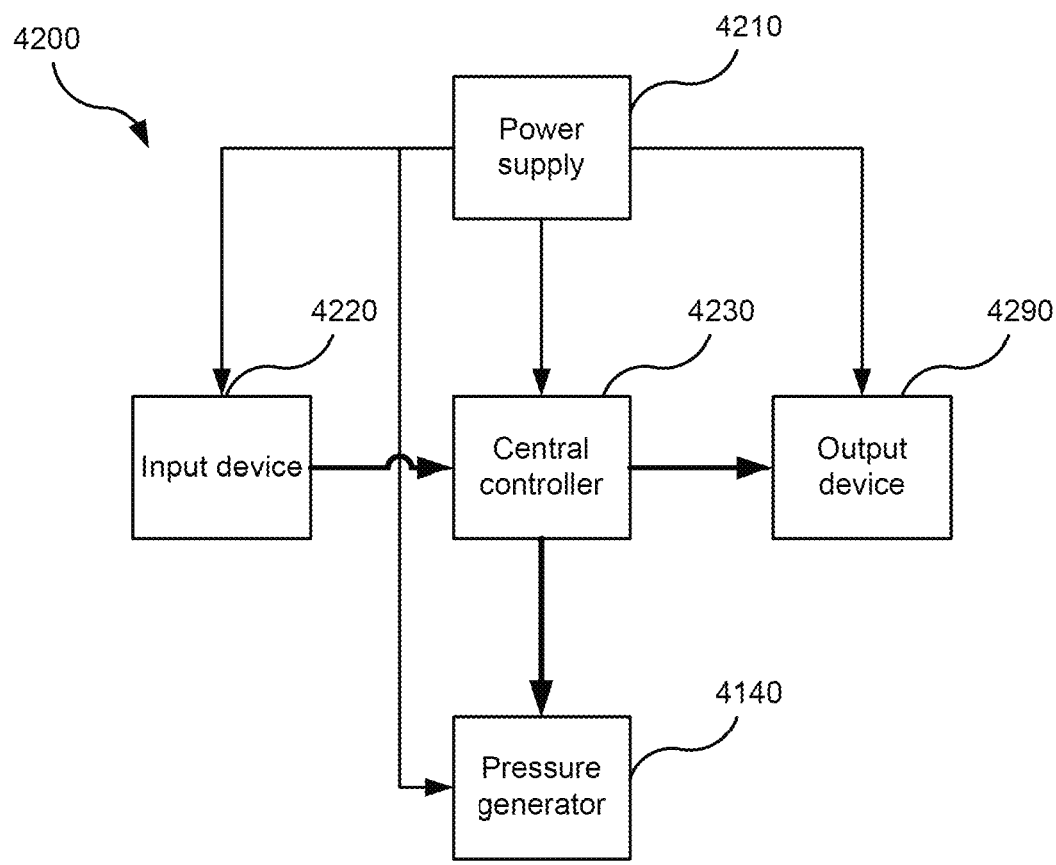
Figure 4E:
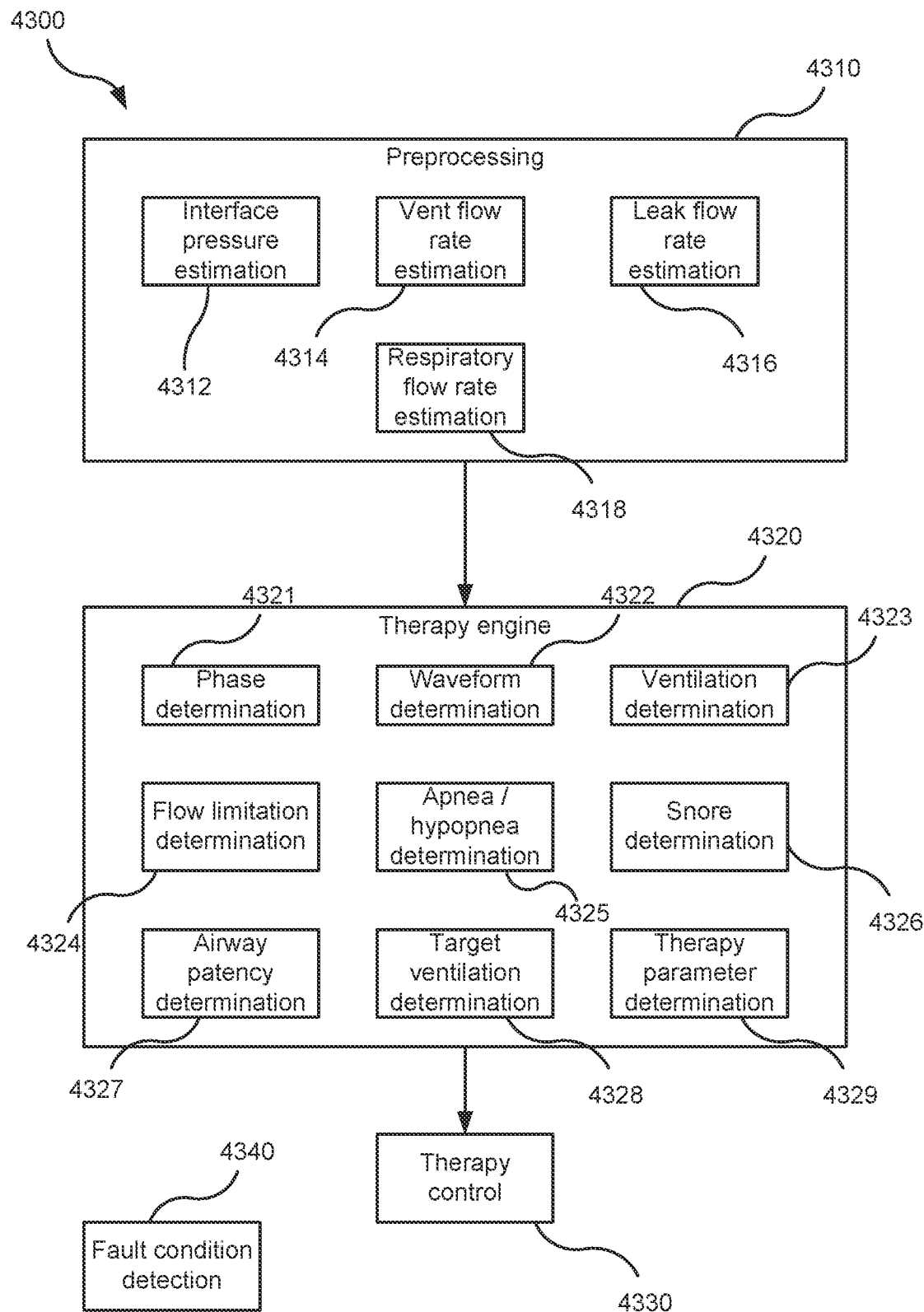
Figure 4F:
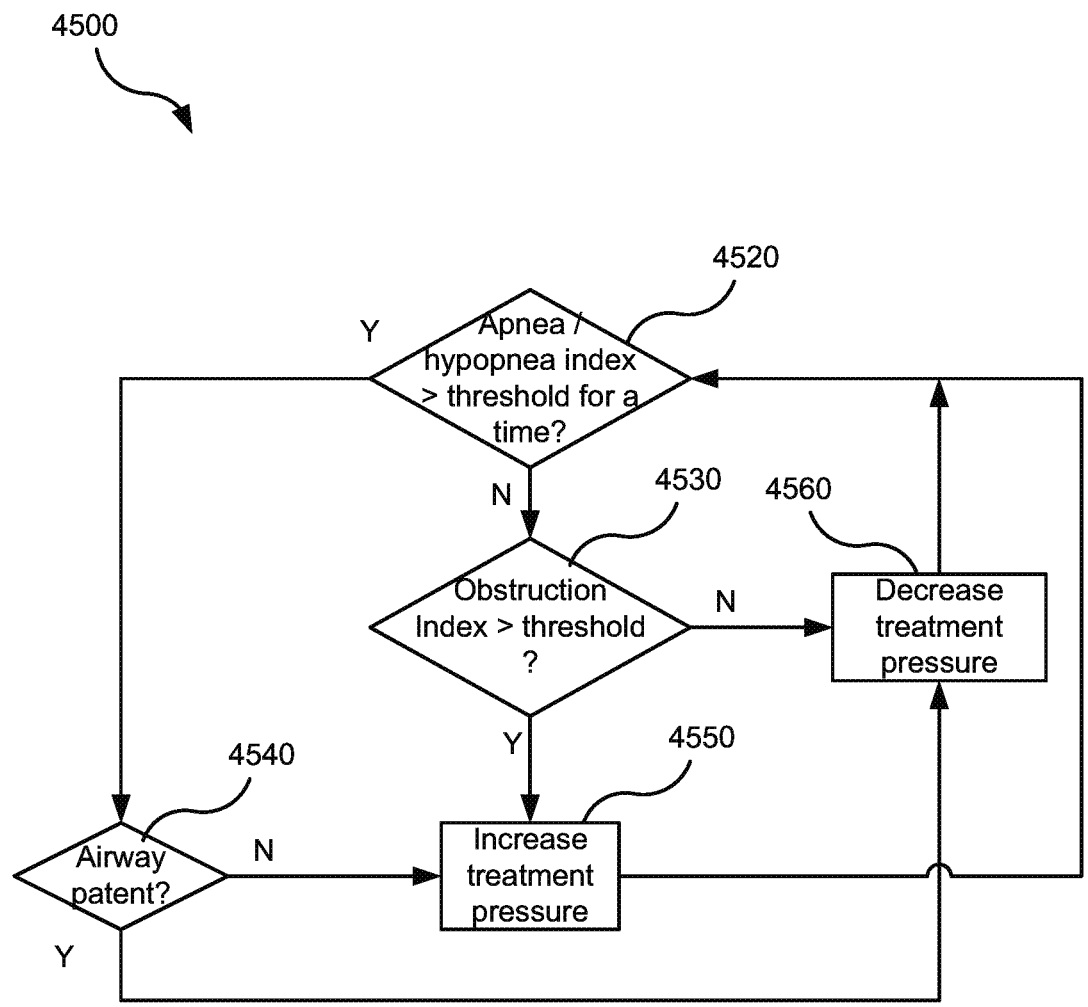
Figure 4G:
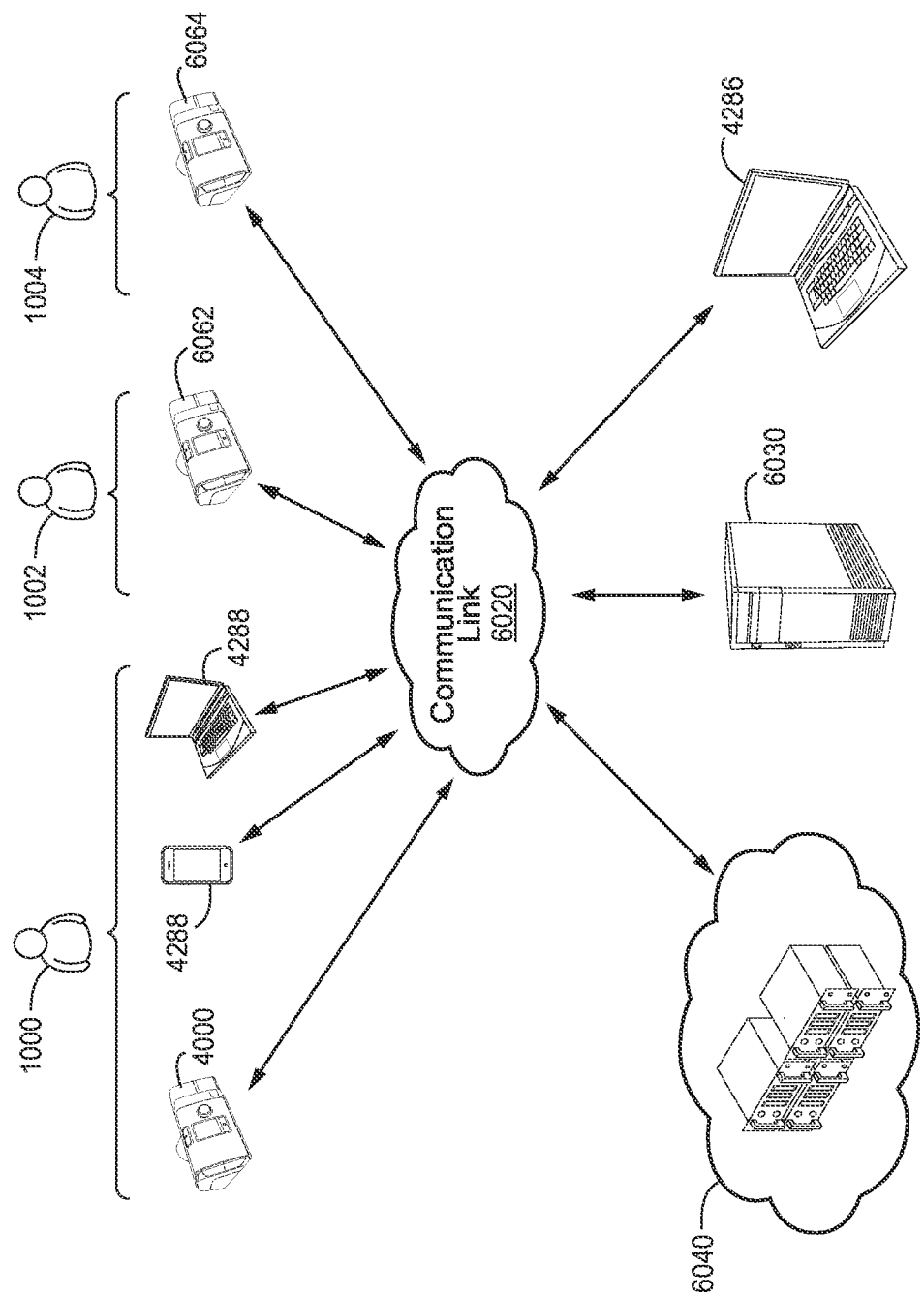

FIG. 4G shows a diagram of a communication system between an RPT device 4000 and a remote computing system. FIG. 4G includes one or more RPT devices 4000 associated with a patient 1000. Each RPT device can be associated with a different patient and/or multiple RPT devices may be associated with a same patient. The present technology is not limited to RPT device, but may be applied to other medical devices. The RPT device 4000 may be configured to communicate via a data communication interface 4280 with a remote external device 4286 and/or local external devices 4288 (e.g., a personal computer, mobile phone, tablet and/or remote control) and/or remote external device. The local external devices 4288 may be configured to communicate directly with the RPT device 4000 when located in the vicinity of the RPT device 4000 or remotely via a local or external network when the local external device 4288 is not located near the RPT device 4000. The remote external device 4286 may be accessible to an appropriately authorised person such as a clinician, manufacturer, and/or supplier of the device. As shown in FIG. 4G, the RPT device 4000 may also communicate with a remote computing system including a server 6030 and/or a cloud computing platform 6040 (e.g., Amazon Web Services™ Google™ cloud platform, Microsoft™ Azure).

One or more other medical devices 6062 or 6064 (which may be RPT devices), associated with other patients 1002 and 1004, may be configured to communicate with the remote external device 4286, the server 6030 and/or the cloud computing platform 6040.

The devices illustrated in FIG. 4G may communicate via a communication link 6020 comprising a remote external communication network 4282 and/or a local external communication network 4284.

The RPT device 4000 and/or medical devices 6062 and 6064 may be configured to transmit, via the communication link 6020, sensor data, demographic feedback, and/or subjective feedback to the server 6030 and/or the cloud computing platform 6040. The server 6030 and/or the cloud computing platform 6040 may be configured to perform patient segmentation and/or advanced analytics using the received data and provide the RPT devices with tailored solutions. The tailored solutions may include tailored coaching programs, personalized therapy, and/or targeted care. The server and/or cloud computing platform may also be configured to provide notifications to provider/clinician portals that are used to manage patient therapy. The notifications may for example indicate that tailored coaching programs, personalized therapy, and/or targeted care may be beneficial for the user and allow the provider/clinician to push those solutions to the RPT device and/or contact the user to discuss the tailored solution.

Figure 4H:
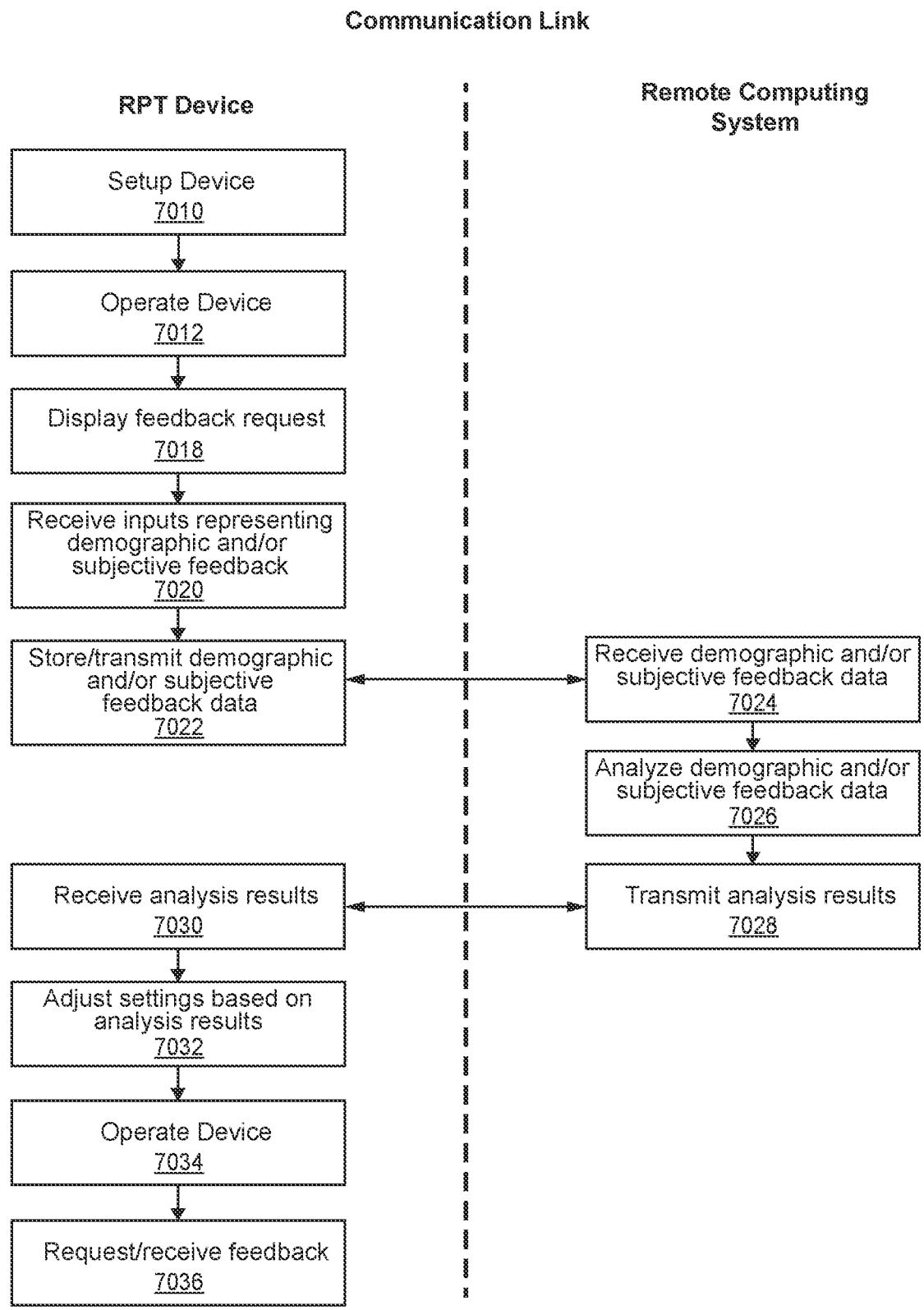

FIG. 4H shows exemplary operations performed by an RPT device 4000 and a remote computing system in accordance with one form of the present technology. While FIG. 4 shows the operations being performed by specific devices, the operations shown are not so limited. One or more operations may be performed by other devices operationally coupled to the RPT device 4000 and/or remote computing system. In some examples, one or more operations shown as being performed by the RPT device 4000 may be performed using a web or mobile application executing on another device (e.g., a local external device 4288).

The RPT device 4000 may be configured to perform setup of the RPT device 4000 (step 7010). The setup may include associating a patient with the RPT device 4000, configuring initial settings of the RPT device 4000 for the patient, and/or providing instructions on how to use the device. One or more operations disclosed in U.S. Provisional Application No. 62/749,430 filed on Oct. 23, 2018, titled "SYSTEMS AND METHODS FOR SETUP OF CPAP SYSTEMS", and U.S. application Ser. No. 16/661,250 filed on Oct. 23, 2019, titled "SYSTEMS AND METHODS FOR SETUP OF CPAP SYSTEMS", each of which is hereby incorporated by reference in its entirety, may be performed during setup of the RPT device 4000.

The setup may be performed when the RPT device 4000 is powered on for a first time after being purchased or reset, or when the RPT device 4000 is assigned to a new patient. The setup may be performed without user interaction by applying settings for the RPT device 4000 stored in memory (e.g., memory 4260 or memory external to the RPT device 4000) or receiving instructions from a remote external device 5286 controlled by a clinician, manufacturer, and/or distributer of the device.

Patient inputs may be requested and received during the setup from the RPT device 4000 and/or other devices. In some examples, instructions and/or questions may be provided using the output devices 4290 and the patient inputs may be received by using the input devices 4220. In other examples, only the RPT device 4000 may be used to receive the inputs during the setup. In other examples, a local external device 4288 may be used, instead of or in addition to the RPT device 4000, to receive user inputs for setting up the RPT device 4000. Display screens may be generated on the RPT device 4000 and/or the external device to request patient inputs during the setup of the device. In some examples, audio instructions and/or audible responses may be received by the RPT device 4000 and/or local external device 4288. In some examples, the data input by a user and/or tailored coaching programs, personalized therapy, and/or targeted care and follow up (e.g., provided in response to the input data) may be provided via a range of different mechanisms (e.g., applications, web, email, phone etc.).

The RPT device 4000 may be operated (step 7012) based on the setting of the device made during the setup. During operation of the RPT device 4000, the operation of the device may be adjusted based on sensor data (e.g., flow sensor 4274, pressure sensor 4272, and/or speed sensor 4276) and/or additional settings received from the patient and/or clinician.

After one or more predetermined conditions are satisfied, feedback requests may be displayed to the patient (step 7018). The feedback request may be displayed on the display 4294 or the device and/or the local external device 4288 (e.g., in an application). The feedback request may request demographic and subjective feedback from the user in the form of a question or instruction. The feedback request may be made automatically when the predetermined condition is satisfied. The feedback is not limited to demographic and subjective feedback and may include additional questions. The feedback, demographic, and/or subjective feedback may include sleep study result, symptoms, comorbidities or other health information, including the presence of other sleep issues (e.g., insomnia), level of knowledge on sleep apnea, level of comfort in approaching therapy, stage in the pathway (new to therapy or experienced user), and/or motivation.

The predetermined condition may include a predetermined amount of time passing after the RPT device 4000 is setup, the patient reaching a specified goal such as using the device for a predetermined period of time (e.g., a pre-set number of hours, days, or weeks), using a specific feature offered by the RPT device 4000 (e.g., operating the device in a low power mode) a predetermined number of times or for a predetermined time period, completing setup of the RPT device 4000, receiving a signal from the remote computing system or device operated by a clinician, receiving feedback requests from another device, having a flag set indicating that feedback requests are available for display to the patient, and/or receiving a notification that feedback request are available for download.

Responsive to the feedback request, inputs may be received representing the patient's demographic and/or subjective feedback (step 7020). The inputs may be received using only the RPT device 4000 (e.g., via the input devices 4220), only the local external device 4288, or the RPT device 4000 and the local external device 4288.

Figure 4I:
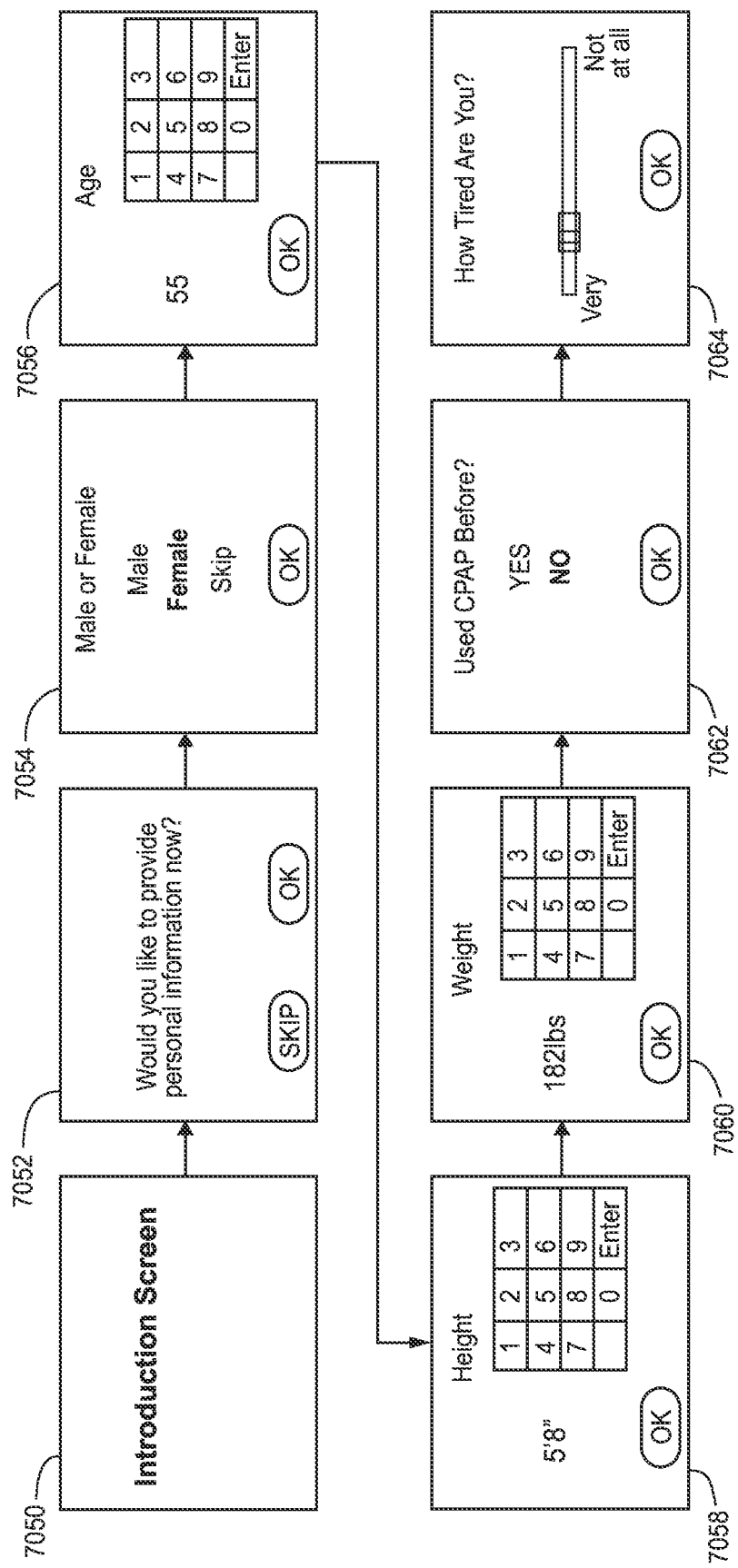

FIG. 4I shows example display screens including demographic and/or subjective feedback requests that may be displayed to a patient. The feedback requests may be displayed on a display 4294 of the RPT device 4000 and/or display associated with the local external device 4288. While FIG. 4I shows the display screens in a specific order, implementation is not so limited. One or more of the display screens may be provided in a different order or not included in the sequence. One or more other display screens may also be included in the sequence.

Introduction screens 7050 and 7052 may include an introduction text, graphics, and/or a video with information introducing the patient to the personalisation features of the system, components, and/or therapy. Introduction screen 7050 may be displayed for a predetermined period of time before automatically transitioning to display screen 7052. Display screen 7052 may provide selectable options for the user to continue with responding to the displayed feedback request or skipping the personalisation feature of the RPT device 4000. In some examples, instead or in addition to skipping the personalisation feature, the user may be provided with an option to provide the information later. The introduction screens 7050 and/or 7052 may be displayed only when the unit is first turned on by a user (e.g., after purchasing the unit or after resetting) or a predetermined number of times until personalized information is received.

Display screen 7054 shows an option for the patient to select his or her sex. As shown in display screen 7054, the patient may be provided a selectable option to skip the feedback request. One or more of the other feedback requests may also include an option to skip a response request.

Display screen 7056 shows an option to enter a patient's age. In other examples, the feedback request may include entering day, month, and/or year of the patient's birthday.

Display screen 7058 shows an option to enter a patient's height and display screen 7060 shows an option to enter a patient's weight.

Display screen 7062 show a question for whether the patient has used the RPT device 4000 before. In some examples, the question may include providing a number of other RPT devices the patient has used, or level of expertise the patients thinks they have on a predetermined scale in using the RPT device 4000.

Display screen 7064 shows a question for the patient to rate how sleepy they usually feel during the day. The user may be provided with a varying scale between not being sleepy and being very sleepy. Other subjective sleep feedback questions may include sleep regularity, sleep satisfaction, sleep alertness, sleep timing, sleep efficiency, and/or sleep duration. The questions may include: do you usually wake up about the same time (within 1 hour) every day, how often are you satisfied with your sleep, how often are you able to stay awake all day without dozing or napping, is the period of 2 am to 4 am usually in the middle of your night-time sleep, are you usually awake for less than 39 min throughout the night, and/or do you usually sleep between 6 and 8 hours per day. One or more of the responses to the questions may be provided with a sliding scale and/or plurality of selectable responses (e.g., rarely, sometimes and usually).

In one example of the present technology, the feedback may include non-subjective feedback. The feedback may include an apnea-hypopnea index entered by the patient and/or retrieved form a database or a physician or clinician.

Based on the results of the feedback, the patient may be assigned a sleep score, coaching programs and/or personalized therapy of the patient. This information may be determined by the RPT device 4000 and/or other devices (e.g., devices shown in FIG. 4G). The sleep score may be displayed to the patient and/or updated as additional feedback is received periodically from the patient. Other sleep score measures may be generated based on therapy measurements captured by the RPT device and shown to the patient on the RPT device display. The sleep score may be based on 1 or more parameters including overall sleep time, number of awakenings, time to fall asleep, time in different sleep stages, AHI, etc. . . . . The sleep score may be recalculated and displayed at the end of each therapy session. Aggregates or averages may be calculated over various time parameters including, but not limited to, weekly, monthly and yearly to provide sleep scores over time. Sleep scores based on sleep measurements may be combined with sleep scores based on feedback to increase the depth of the sleep score and/or provide further discretion on coaching programs and/or personalized therapy that may be directed to the patient.

Other display screens may include other feedback requests such as, level of how well the patient slept at night, mask comfort level, comfort of breathing while using the CPAP, and/or satisfaction level with operation of the device. In some example, the subjective questions (e.g., comfort of sleep) may be received a plurality number of times, each for a different time period. For example, the RPT device 4000 may be configured to request a patient to provide feedback on the comfort of sleep for a predetermined number of days (e.g., seven days).

The display screens requesting feedback may include an option to select that the response is not known and/or provide with an option to retrieve the information from an external source (e.g., a database, physician's records, external device etc.).

In some examples, a single feedback request may be displayed on the display or two or more feedback requests may be displayed simultaneously on a single screen. For example, the request to enter the age and the height of the patient may be simultaneously displayed on one screen.

In one form of the present technology, the display screens with feedback requests may be displayed on a touch input display. In one form of the present technology, inputs to the questions displayed on the display may be input using one or more input devices 4220 including physical buttons, switches or dials, or software devices accessible via the touch screen.

In one form of the present technology, the feedback requests may be audibly output to the patient using speakers and/or verbal feedback responses may be captured via a microphone.

After the responses to the feedback requests are received, the responses can be stored in memory and/or transmitted (step 7022) to the remote computing system. In one form of the present technology, the data may be transmitted directly to an on-demand cloud computing platform (e.g., Amazon Web Services™, Google™ cloud platform, Microsoft™ Azure). The responses may include demographic and/or subjective feedback data. In one form of the present technology, if a connection to the remote computing system is not available the feedback data may be stored in memory 4260 until the connection becomes available.

In step 7022, other data may be transmitted with the feedback data to the remote computing system. For example, the other data may include therapy data for determining whether the patient has used the RPT device according to the compliance rule, the RPT device 4000 identification information (e.g., serial number, model number, and/or software version on device, manufacturing information), the RPT device 4000 location information, user profile data, data captured by sensors (e.g., transducer 4270), settings applied during setup of the RPT device 4000, type of accessories coupled to the RPT device 4000, and/or modification made to settings by the patient and/or when such modifications were made.

The remote computing system, receives data (step 7024), analyses the data (step 7026), and transmits analysis results (step 7028) to the RPT device 4000 and/or web or mobile application. The remote computing system may receive the demographic and/or subjective feedback, and other data from the RPT device 4000 or local external device. The data may be directly received by the remote computing system for processing. The remote computing system may include a server 6030 and/or a cloud computing platform 6040. The server 6030 may be a non-cloud based server managed by the manufacturer or clinician.

The remote computing system may segment the patient's data (e.g., age range, gender, weights, environment, etc. . . . ), and use models developed using similar and/or different data from other users to determine what the patient needs and/or what settings on the RPT device 4000 should be modified.

The models may be predetermined by advanced analytics, artificial intelligence, and/or machine learning. The remote computing system may include models determined based on information about operation of other RPT devices (e.g., medical devices 6062 and/or 6064) associated with other patients 1002 and/or 1004, and demographic and subjective feedback received from the other patients 1002 and/or 1004. The advanced analytics, artificial intelligence, and/or machine learning may be performed on data from a large number of patients and the models may be updated with new data as new data (e.g., data including demographic feedback, subjective feedback, and/or changes to compliance standards) become available. The analysis results may include tailored coaching programs, personalized therapy, and/or targeted care and follow up.

In response to transmitting the feedback data, the RPT device 4000 may receive analysis results (step 7030) from the remote computing system. The analysis results may include tailored coaching programs, personalized therapy, and/or targeted care and follow up. Alternatively, the analysis results may not be sent to the RPT device directly. Instead the analysis results may be sent to a remote provider portal or clinician portal. The provider/clinician could then contact the user to discuss the analysis results, or through the portal the provider/clinician could then approve, modify, and/or push the analysis results to the RPT device. The feedback data itself may also be sent to the provider/clinician portal to allow the provider or clinician to perform their own assessment and direct targeted care and follow up.

The tailored coaching programs may be provided to increase engagement and motivation of the patient. The tailored coaching programs may include instructions on how to properly use the device, explain benefits of using features provided by the device, and/or suggest other medical devices and/or accessories that may be beneficial for the patient. For example, information about an accessory (e.g., different type of mask) that will improve the patient's experience using the RPT device 4000 may be displayed on the display 4294 or the local external device 4288.

The personalized therapy may provide for automated comfort setting which have been proven to increase long term adherence (LTA). The personalized therapy may be automatically applied to the RPT device 4000 without patient interaction. In some examples, the patient may be provided with information about changes to the therapy and be requested to accept the proposed changes before they are applied.

The targeted care and follow up may include notifying the patient of need to make modifications in care or need to schedule a meeting with a clinician or another expert. In some example, the RPT device 4000 and/or the local external device 4288 may be used to schedule and/or conduct a meeting with a clinician or other expert.

The analysis results may be used to adjust settings (step 7032) of the RPT device 4000. Modifying the settings may include adjusting one or more comfort settings of the RPT device 4000. For example, the analysis results may include instructions to modify, pressure ramp settings, expiratory relief settings, humidity settings, and air temperature settings. In one form of the present technology, the analysis results may indicate that continued use of the RPT device 4000 is not safe and the use of the RPT device 4000 may be disabled.

After the analysis results are applied, the operation of the RPT device 4000 may be continued (step 7034). Applying the analysis results and operating the RPT device 4000 using the updated settings will control the RPT device 4000 more effectively to meet the needs of the patient. In some example, the modifications may be made to operate the device more efficiently (e.g., using less power or lower temperature of a heated tube delivering air) without significantly sacrificing the patients comfort.

After a predetermined time, one or more of the feedback requests made earlier and/or new feedback requests may be presented to the patient and responses received (step 7036). The response may be used to determine whether the previously applied settings were effective and/or whether additional changes to the operation and/or use of the RPT device 4000 need to be made. The additional feedback request may be made periodically or when new feedback requests are made available by the remote computing system.

In some examples, the additional feedback request may be displayed every time the user powers on the RPT device 4000. When the RPT device 400 is used, the patient may be displayed with a sleep score (based on 1 or more of the previous sessions sleep measurements, aggregates or averages of sleep measurements from multiple sleep sessions, user feedback, or some combination thereof), a daily insight (e.g., daily recommendation that may be tailored based on the patients and/or other patient's feedback). Providing the additional feedback may include the user updating one or more of the previously provided feedback (e.g., age, height, weight and/or sleep feedback).

In one form of the present technology, some feedback requests may be presented on the RPT devices 4000 and other feedback requests may be presented on the local external device 4288 or another medical device associated with the same patient 1000. Feedback requests that are presented on one device may be marked as displayed and not requested on other devices.

In one form of the present technology, the operations relating to displaying feedback requests and receiving inputs for the feedback requests may be performed during the setup (step 7010) of the device.

In an alternative, or preferably in addition, to transmitting responses to the feedback requests for remote analysis, the RPT device may further have pre-stored micro-coaching responses (e.g. insights, encouragement, identification of helpful resources, etc. . . . ) to provide based on the input feedback response. For example, FIGS. 7A-7F described below, illustrate a workflow on the RPT Device including questions and micro-coaching responses that may be used during the set-up of the device (pre-therapy). For example, the feedback request may present the question "Prior to starting therapy how sleepy did you usually feel during the day?" with the option to select an answer from one of "Extremely", "Very", "Moderately", "Slightly", and "Not at all". If the feedback response from the patient is "Extremely" or "Very" the RPT device may display an insight such as "X % of extremely or very sleepy users will feel less tired after 4 weeks of therapy". Similarly, if the feedback response from the patient is "Moderately" or "Slightly" the RPT device may display an insight such as "X % of moderately or slightly sleepy users will feel less tired after 4 weeks of therapy". If the feedback response from the patient is "Not at all" the RPT device may display an insight such as "CPAP therapy can also improve many quality of life factors beyond sleepiness." Providing relevant insights in response to feedback can improve patient confidence, help them understand and better see the benefits of their therapy, and increase motivation to continue with therapy.

By way of another example, FIGS. 8A-8E described below illustrate a workflow on the RPT device including questions and micro-coaching responses that may be presented after therapy has begun to check-in with the patient's therapy journey at predetermined intervals or specific days (e.g. the data may be collected on days 3, 7, 14, 21, and 28, but is not so limited). For example, on the $3^{rd}$ day the feedback request may present the question "How is therapy going?" with the option to select an answer from one of "Challenging", "Getting There", and "Great". If the feedback response from the patient is "Great", the RPT device may display an encouraging note such as "You're doing so well. Keep up the great work!". If the feedback response is one of "Challenging" or "Getting there" the RPT device may present a follow up question to identify any specific trouble areas. For example, presenting the question "Any particular issue?" with the option to select an answer from one of "Mask", "Getting used to therapy", and "Device". In response to the input feedback response, the RPT device may present the patient with resources that may be useful to the patient for trouble shooting. For example, the RPT device may alert the patient to troubleshooting aids that can be run on a mobile application executing on another device (e.g., a local external device 4288), such as the one illustrated in FIG. 6. Additionally, the RPT device may provide the patient with instruction for downloading the mobile application, connecting the PRT device to the mobile application, and employing the appropriate trouble shooting aid.

By way of still further example, the RPT device may also present questions at predetermined intervals (e.g. weekly) that aim to compare answers over the course of therapy. For example, on the 7th day, the RPT device may present the question "How sleepy did you fell this past week?" with the same answer options that were used during setup for the initial sleepiness questions, that is, "Extremely", "Very", "Moderately", "Slightly", and "Not at all". Depending on whether the input feedback response indicates that the patient has seen a decrease in sleepiness, an increase in sleepiness, or minimal or no changes to sleepiness the RPT device may present micro-coaching insights, encouragements and resource identification to keep the patient engaged with therapy facilitate improvement, and achieve compliance and OTA. While micro-coaching using pre-stored responses has been illustrated in connection with subjective feedback related to sleepiness and therapy progress, it should be understood that responses may be utilized for any feedback request, including but not limited to any of the subjective and/or demographic feedback described throughout this application. It should also be understood that the pre-stored responses may be updated over time based on the advanced analytics, artificial intelligence, and/or machine learning that may be performed on remote computing systems as described elsewhere throughout this application. It should still further be understood, that the micro-coaching responses may not be pre-stored on the PRT device memory, but rather, may be driven by the remote computing/processing system as described herein.

Figure 4J:
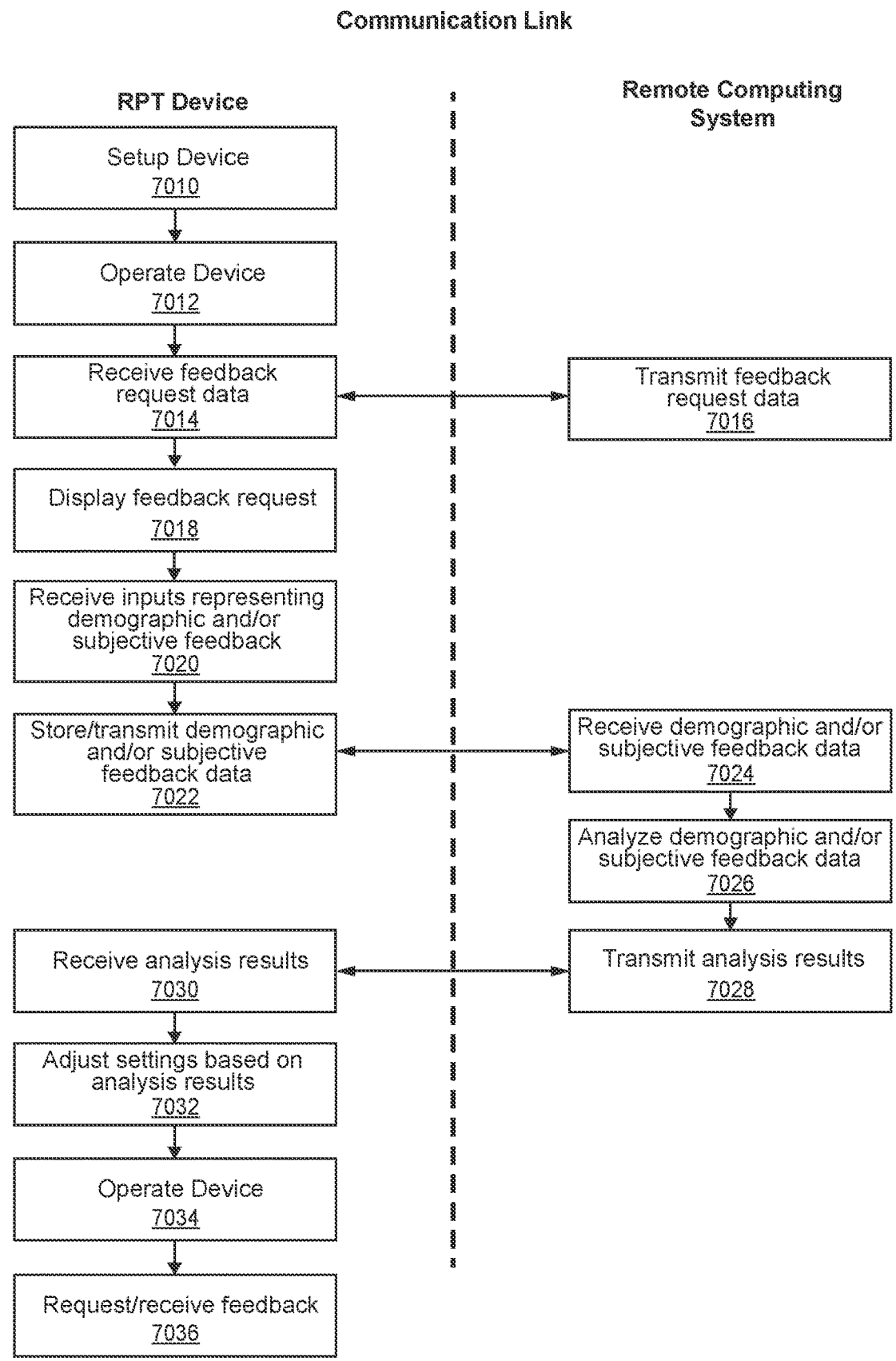

FIG. 4J shows another example of operations performed by an RPT device 4000 and a remote computing system. In the example, illustrated in FIG. 4H, the feedback request data was pre-stored on the RPT device 4000. For example, feedback request data may have been pre-stored in memory by the manufacturer, distributer or clinician. In the example illustrated in FIG. 4J, the remote computing system transmits the feedback request data (step 7016). The RPT device 4000 receives the transmitted feedback request data (step 7014) from the remote computing system and uses the data to receive feedback from the patient. In some examples, the system transmitting the feedback request data may be a different system from the system performing the analysis using the demographic and/or subjective feedback data transmitted from the RPT device 4000.

The remote computing system may transmit the feedback request data in response to a request from the RPT device 4000. In some examples, the remote computing system may push the feedback request data to the RPT device 4000 at some predetermined period of time, or ad hoc (either directly or through the home medical equipment).

The feedback request data may be entered by a provider or clinician. The provider or clinician may be provided with a user interface to enter their own questions as part of the feedback request data. The user interface may be provided as part of the provider or clinician portal on the remote computing system. The provider or clinician may be provided with a feature to ask their own patient questions via the RPT device 4000 or device associated with the RPT device 4000 (e.g., the local external device 4288). For example, the provider or clinician may enter the questions using the remote computing system. The provider or clinician may associate one or more of the questions with one or more conditions for distributing the questions to the RPT device 4000. The conditions may include one or more patient characteristics, device type, peripheral devices (e.g., type of mask, tube etc.) connected to the RPT device 4000, and/or device operating parameters. Feedback input in response to the feedback request may be shown back to the provider or clinician through the provider or clinician portal.

Figure 4K:
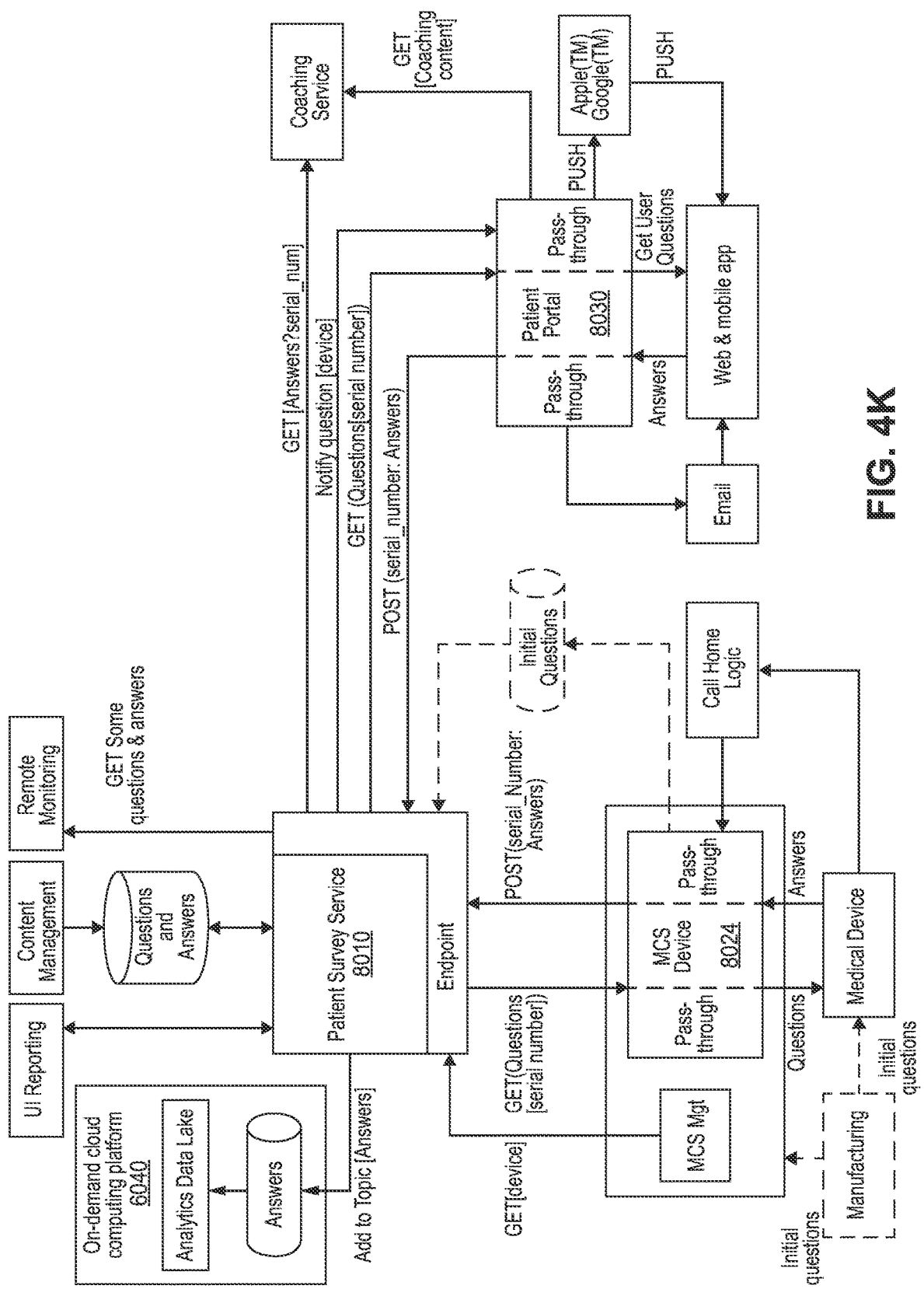

FIG. 4K shows a data flow diagram in a system providing communication between a medical device (e.g., RPT device 4000), a patient portal 8030 and a patient survey service 8010.

The patient survey service 8010 may be implemented on one or more servers which may include cloud and/or dedicated servers (e.g., server 6030). The patient survey service 8010 may coordinate the management and communication of questions and answers for the demographic and subjective feedback and/or micro-coaching insights, encouragements and/or resource identification. As shown in FIG. 4K, the patient survey service 8010 may support sending information (e.g., questions micro-coaching insights, encouragements and/or resource identification) to a patient's account associated with a medical device. The patient's account may be accessed via a web application or mobile application executed on a local device 4288 or via the RPT device 4000. The patient's account accessed via the web or mobile application can provide for monitoring, reporting and/or setting of the medical device, coaching to the patient, micro-coaching insights, encouragements and/or resource identification.

The patient survey service 8020 may notify clients of questions being available. The questions may be made available when they are added (e.g., by marketing) to a content management system. The questions may be retrieved from the patient survey service 8020 via GET calls. In one example, the patient's account accessed via the web or mobile application may call home and get questions via proxy through the patient portal 8030. The questions may be provided in JavaScript Object Notation (JSON) format, representing, the content of the questions and possible answers. The presentation of the questions may be embedded in the application as HTML content. The patient's account accessed via the web or mobile application may send answers back to the patient survey service 8020 via proxy through the patient portal 8030 (e.g., via a POST instruction).

The medical device may call home and get questions via proxy through the MCS device 8024 and send answer back to the patient survey service 8020 via proxy through the MCS device 8024 (e.g., via a POST instruction). The GET calls may include a serial number of the medical device for the patient survey service 8010 to keep track of which questions have been sent to which device and/or application.

According to one aspect, the patient survey service 8010 may manage the questions such that questions are made available to the patient portal after a predetermined period of time (e.g., 48 hours). This may minimize the questions being asked twice.

According to another aspect, the patient survey service 8010 may manage the questions such that questions already answered by a patient are not shown again. In one example, the patient survey service 8010 may keep track of answered questions on one platform (e.g., a medical device) and not display those questions on a patient's account accessed via a web or mobile application.

Responses to the questions may be received by the patient survey service 8010 from the medical device or the patient's account accessed via the web or mobile application. The answers may be transmitted to a cloud computing platform 6040 for advanced analytics. The cloud computing platform may include an analytics data lake with data from a large number of other patients. Deep neural networks may be used to build models and analyse the received answers. In some examples, the patient survey service 8010 may put the received answers on a queue for advance analytics consumption.

The patient survey service 8010 may support providing the questions and/or answers to a remote patient monitoring system. The remote monitoring may be provided via a web or mobile application executing on a remote external device 4286. The remote monitoring may provide for a secure, cloud-based patient management system for online patient monitoring, and enable clinician quick access to patient data, share clinical insights with other health professionals and reduce costs related to patient follow-up. The remote monitoring may receive operation information of the medical device, compliance information, setting of the device, changes made to the settings of the device, questions presented to the patient, and/or answers received from the patient. The clinician may use the data provided by the remote monitoring to suggest further changes to the coaching programs and/or personalized therapy of the patient.

The patient survey service 8010 may support receiving initial hard coded questions from the medical device. During manufacturing, initial questions may be loaded to the medical device. The medical device may present the initial questions and receive responses to the questions during setup or when a predetermined condition is satisfied (e.g., after the medical device has been used for a predetermined period of time or after a predetermined period of time has passed after setup). The initial questions may be transmitted by the medical device to the patient survey service 8010 for distribution to the remote monitoring and/or the web or mobile application. In some examples, the initial questions may be made available via the web or mobile application if the initial questions have not been answered on the medical device. The patient survey service 8010 may keep track of which initial questions have been answered.

In some examples, the initial questions stored on the medical device may be separately provided to the patient survey service 8010 by the manufacturer. In this example, the patient survey service 8010 may receive identification of the medical device (e.g., serial number) and the initial questions that have been stored on the medical device. The initial questions stored on different medical device may depend on the type of device and/or features provided by the device.

The patient portal 8030 may receive coaching content to provide the patient with instructions on how to use the device, how to improve use of the device, and/or get better results from the device. The coaching service may provide coaching content based on analysis results of the patient's demographic and/or subjective feedback.

5.7 Two-Way Communication for Patient Reporting and Providing Therapy and/or Coaching In one form of the present technology, a medical device (e.g., a RPT/flow generator) may include two-way communication with one or more remote processing systems to provide insight into operation of the medical device and/or patient's use of the medical device. The medical device may collect operation and/or patient information (e.g., demographic and/or subjective feedback) and provide this information to another device for processing and reporting to other devices associated with home medical equipment (HME) providers and/or other individuals associated with producing, distributing and/or maintaining of the medical device (Provider Portal), and/or managing the therapy of the medical device users (clinician portal). The provider portal and the clinician portal may run the same software program, different modules within a software program, or different software programs tailored to the various needs of the HME Providers, and/or other individuals associated with producing, distributing and/or maintaining of the medical device, and clinicians. The HME providers, clinicians, and/or other individuals may use this information to improve the production, distribution, maintaining, advising patients, modifying settings or therapy parameters, making updates and/or addressing patient concerns.

In one example, feedback collected from the patient on the medical device or input from the patient portal may be collected and output on provider portal (or clinical portal) accessible by the HME (or clinician). The feedback data may be filterable to allow the HME and/or clinician to quickly find, sort, filter, and/or manually flag patients, based on the feedback, for some follow-up action (e.g. contact, settings change, coaching suggestions, etc. . . . ). In one further example, feedback and/or other data from the medical device (e.g., a flow generator) or input from the patient/clinical portal may be run through an analysis on a back end and then, instead of pushing it back to the medical device for some action (e.g. settings change, coaching suggestions, etc. . . . ), insights may be pushed to the provider portal (or clinical portal) with some possible actions (e.g., to push one or more notification, setting, suggestion, etc.) to the medical device. Examples of the possible actions include notifications, and/or settings for tailored coaching programs, personalized therapy, and/or targeted follow-up contact or care. Instead of receiving the action information from the back end of the medical device (e.g., remote computing system in FIGS. 4H and 4J), the action information may be received from another device that receives the analysis and generates the action information. These other devices may be controlled and managed by HMEs and gain insight via the provider portal. In some examples, information collected in the clinical portal (e.g., from patients and/or entered by clinician) may be provided to the backend system for processing and/or distribution to other HMEs.

As will be discussed in more detail, the provider (or clinical) portal may provide insight into a plurality of patients. The provider (or clinical) portal may provide insight into a plurality of patients associated with an HME (or clinician) and insight into a plurality of patients not associated with the HME (or clinician). Sensitive and personal information about the plurality of patients not associated with the HME is not provided to the HME (e.g., hidden). The HME may use this information to provide helpful information to the patient, and/or improve medical device and/or accessory use.

Unlike conventional systems in which information for a medical device and/or use had to be pre-loaded and were modified by a highly trained technician, examples of the present technology provide for the medical device to be configured automatically after the device is deployed for use by a device associated with a HME supplier, based on the device associated with a HME supplier receiving information received from the medical device by a backend system. In addition, examples of the present technology provide insight into use of the medical device not previously provided by conventional systems.

Examples of the present technology can increase the HME (or clinician) business efficiency. For example, the present technology can gain HME patient follow-up efficiency by reducing new patient follow-up calls (e.g. by directing follow-up through a mobile device and/or in a browser, and flow generator or App; or by distinguishing users in higher need of follow-up to focus follow-up effort efficiently). Long term patient adherence can be increased by increasing new patient adherence during initial therapy and increasing confidence of new patients acclimating to therapy.

Examples of the present technology can increase compliant medical device use. A portion of patients may still feel tired after using an RPT device 4000 (e.g. flow generator) for a predetermined period of time (e.g., a week or more of therapy). This group of patients may have lower compliance and poorer long term adherence, which can be captured by collecting patient data and performing the analysis. The system can collect data from 100,000s of patients and provide insight into use of the medical device. The insight may help in the system or a user identifying corrective actions, improved instructions, and/or modified therapies that can be made to improve compliance and reduce long term dropout rate for using the medical device.

Examples of the present technology address issues with patients who may be struggling to acclimate to sleep apnea therapy. A feedback module provided through a patient portal may ask patients questions such as "how they are feeling", "how sleepy they felt in the past week" and "how therapy is going," for example. The questions may be asked multiple times over a certain time period (e.g. about 5 times during the first 30-day compliance period) in an effort to better understand the patient so as to provide them a higher level of care. These questions may be asked via a patient portal from either the flow generator (see e.g., FIGS. 7-8) or the remote device (e.g. user mobile app (see e.g. FIG. 6)). In some examples, the system may be configured to not ask the questions from both the flow generator OR the patient app.

On both the user app and the flow generator these questions will result in follow-up questions about any problems the user is facing and micro-coaching responses, such as those shown in the pre-therapy workflows of FIGS. 7A-7F and post-therapy workflows of FIGS. 8A-8E) aimed at providing the new and/or struggling pap user with valuable insights about their therapy acclimation journey. Supporting the patient with these insights can improve confidence, help them understand and better see the benefits of their therapy, and increase motivation to achieve compliance and long term adherence. Other follow-up questions may be generated by a clinician (or HME) based on received information about the patient/medical device and pushed to the user via the clinician (or provider) portal.

Micro-coaching responses (e.g. insights, encouragement, identification of helpful resources, etc. . . . ) to the user can be provided in response to questions provided to the user pre-therapy and/or post therapy. The micro-coaching responses can be provided when a user makes an initial selection of a response to a question and/or when the user confirms a selection of a selected response. The responses received from the user in response to the questions may be subjective and/or non-subjective. Same or different questions may be presented to the user on predetermined days and/or at predetermined intervals (e.g., days 7, 14, 21 and 28) after satisfying a predetermined condition (e.g., after initial setup, completion of a predetermined therapy procedure). In one example, a same plurality of questions may be asked at the predetermined days and/or predetermined intervals. The questions, responses to the questions and coaching responses may be pre-stored on the device and/or may be received from a remote device, where they are generated by a user and/or automatically (e.g., based on preset settings, advanced analytics, artificial intelligence, and/or machine learning).

In some examples of the present technology, one or more check-in questions may be asked outside of the predetermined intervals. Based on the response to a check-in question, a determination can be made as to whether other questions (e.g., the questions asked at predetermined intervals) should also be asked before reaching the next scheduled inquiry. In some examples, the check-in question may be asked in response to detecting one or more predetermined conditions. The predetermined conditions may include detecting operating of the medical device outside of preset parameters (e.g., noise during use exceeding a preset value, vibration exceeding a preset value, failure of user to use the device, and/or detecting air leak).

FIG. 6 illustrates a user interface that may be provided in an application executed on a device (e.g., mobile device (as shown), computer, medical device and/or a browser executed on a device). As shown in FIG. 6, the user interface may include receiving subjective and non-subjective responses.

In FIG. 6 the first set of screens 602-610 may be displayed on predetermined days and/or at predetermined intervals, and the second set of screens 612-616 may be displayed when providing a check-in question.

In the first sequence of screens 602-610, a user may be first asked (screen 602) whether they have time to provide feedback on the therapy. If the user answers "no thanks", the system may request for feedback again on the next predetermined day and/or when the predetermined interval expires.

If the user selects to provide feedback (OK in screen 602), one or more questions may be displayed simultaneously or sequentially. In FIG. 6, two questions are displayed sequentially in screens 604 and 606. Screen 604 shows a first question "How sleepy did you feel this week?" being presented to the user. Screen 606 shows a second question "How the therapy is going?" being presented to the user. One or more options for providing a response to the questions may be simultaneously displayed with each of the questions. The one or more of the responses to the questions may be provided with a sliding scale and/or plurality of selectable responses.

As shown in screen 604, a plurality of selectable objects, each corresponding to a different level of how sleepy the user feels, are displayed with the first question. The different selectable objects may respectively corresponds to "extremely", "very", "moderately", "slightly", and "not at all". In screen 604, the fourth object corresponding to slightly sleepy is selected. As the user selects different objects, text indicating the level of sleepiness may be displayed above the selectable objects. Alternatively, the text representation (e.g. "extremely", "very", "moderately", "slightly", and "not at all") itself may be the selectable object.

As shown in screen 606, a plurality of selectable options are displayed simultaneously with the second question. In response to the question "How is your therapy going?" the selectable options can include "Great," "Getting there" and "Challenging." In response to each selection, additional text (e.g., micro-coaching responses) may be displayed to encourage the user to continue with the workflow so that coaching can be provided. For example, in screen 606, in response to selecting "Challenging" encouraging response "We'd like to fix that if we can. Tell us a bit more on the next page." is displayed below the selectable options. Same or different encouraging response can be displayed when one of the selectable options is selected. After selecting one of the options, the user may continue with the workflow (select "Continue" in screen 606 or save the answer and leave the workflow.

If the user continues with the workflow after answering the first and/or second questions, the system may display one or more options for addressing issues identified from the responses to the plurality of questions (screen 608). Screen 608 illustrates three selectable options determined based on the responses received from the user to the first and second questions. The selectable options include "Getting used to therapy", "Fitting the mask" and "Using the machine." In response to an initial selection of one of the responses, an encouraging response to proceed with the selected option may be displayed. For example, in response to selecting "Fitting the mask", the screen 608 may display "Sure. Try going through mask setup to see if that helps." to encourage the user to perform mask setup by continue with the workflow by selecting "Go to Mask Setup." In response to selecting "Go to Mask Setup", the mask setup of the RPT device may be initiated (screen 610).

While not shown in the screens of FIG. 6, an option to skip a question may be provided with one or more of the questions. In some examples, an option to skip the question may be provided only for some questions. A selectable object to skip the question may be simultaneously displayed with the question when the question is displayed. In another example, the object providing an option to skip the question may be displayed only after a predetermined period of time has passed without receiving a response to the question. The delay in displaying the object with skip option may encourage the user to provide a response before providing the option to skip the question.

The second set of screens 612-616 may be displayed when providing a check-in question. In screen 612, the user is asked whether they have time for a question. The screen 612 including the question may be asked when the user begins using the RPT device, after detection completion of using the RPT device, during therapy by the RPT device, and/or when the user checks for a sleep score (e.g. myAir score) in the application.

If the user selects that they have time (OK in screen 612), screen 614 may display (sequentially or simultaneously) a check-in question "How are you feeling about therapy?" and a plurality of selectable responses.

Depending on the selection, the check-in may be completed without requesting additional questions or additional questions may be displayed to the user. For example, if the user selects "Its going well" and "Done", then the system may determine that there is no need to provide the user with additional questions and/or micro-coaching responses (e.g. insights, encouragement, identification of helpful resources, etc. . . . ). However, if the user selects "Just ok" or "I'm not feeling good about it," micro-coaching responses may be provided. For example, if the user selects "Just ok", as shown in screen 616, the system may display "We'd like to fix that if we can. Tell us a bit more on the next page" and provide an option to "Continue" with the workflow or to save the answer and leave. If the user selects "Continue" in screen 616, then the system may display the questions shown in screens 604 and/or screen 606 and based on responses display screen 608 and/or 610.

In some examples of the present technology, the selection of the responses to the questions may include the processing system receiving a first user input to the displayed response (e.g., a response in screens 604, 606, 608, 614, or 616). The first input may include a touch input received via the display or a selection made by an input device (e.g., a mouse, a touch pad provided outside of the display, physical buttons on a device). As discussed above, in response to the first input, micro-coaching responses and/or indications of what the responses represent may be displayed on the screens. In some examples, the first input may include a user moving a cursor over the displayed responses and the micro-coaching responses and/or indications being displayed when the cursor is positioned at least partially over one of the displayed responses.

After the first input is received a second input to a confirmation of the selection may be made by the user selecting another displayed object and/or text. The other object or text may include "Ok", "Continue" or "Next." In some examples, the confirmation may include receiving a second input to the response selected by the first input. While the object and/or text to confirm the selection in FIG. 6 is displayed on a same screen with the selectable responses, the object and/or text to confirm the selection may be displayed on a different screens after the selection of the response is made. The different screen may maintain or remove the display of the selected response.

In some examples of the present technology, the processing system may be configured to perform voice recognition and the selection of the response to questions may be performed in response to a voice instruction. The processing system may receive voice data, analyse the voice data, and determine to which of the available responses the analysed voice data matches. The voice data may also be analysed to determine whether "Ok", "Continue" or "Next" is spoken by the user.

FIGS. 7A-7F illustrate pre-therapy flow, including questions and insights, as provided in the medical device, but which may also be provided outside of the medical device (e.g., application executing on a remote device and/or in browser). In some examples of the present technology, one or more of the screens shown in FIGS. 7A-7F may be displayed by the remote device and/or the browser. FIG. 7A illustrates an overview of the pre-therapy flow and FIGS. 7B-7F illustrate a detailed view of the portions of the overview shown in FIG. 7A. One or more of the screens shown in FIGS. 7A-7F may be optional and/or may be displayed in a different sequence, and/or may be combined and displayed simultaneously on a same screen.

Figure 7B:
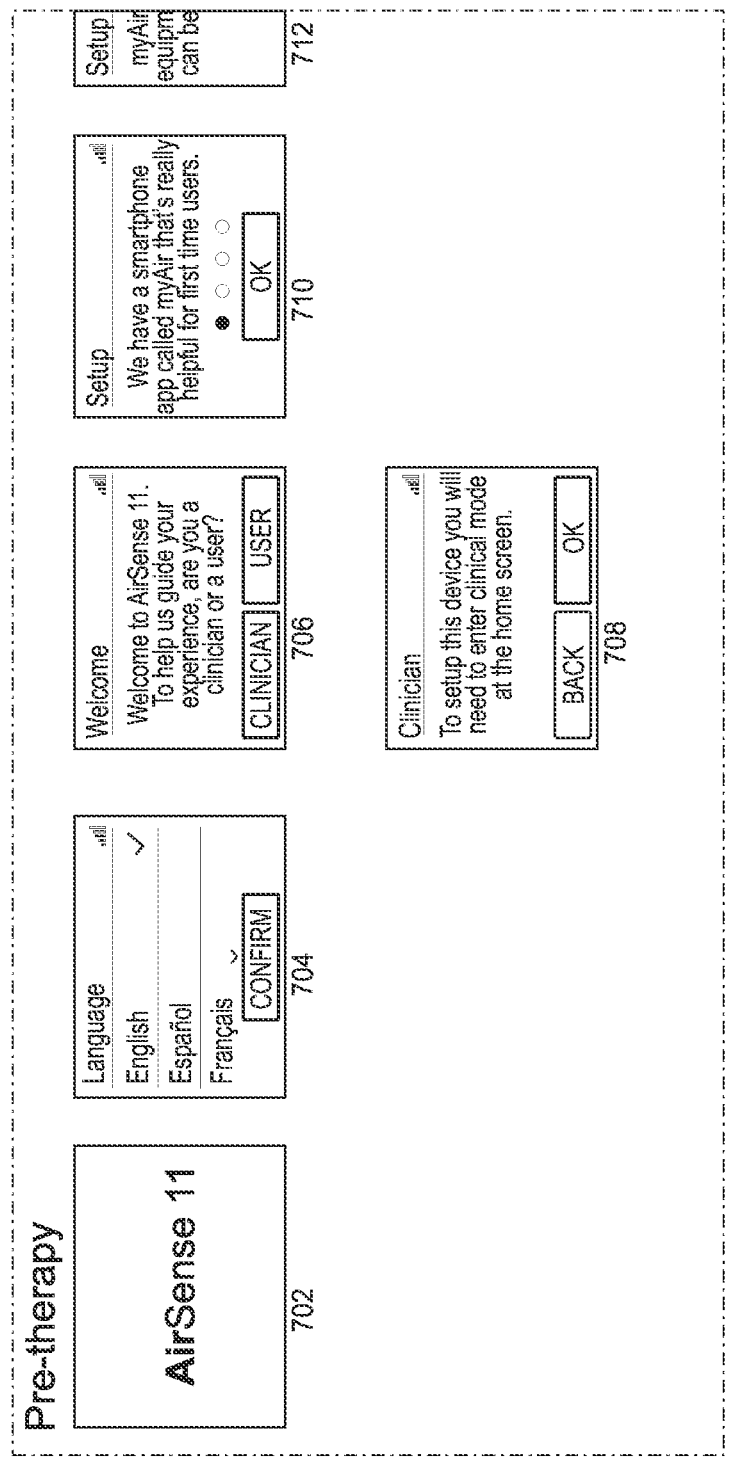

In FIG. 7B, screen 702 may be displayed during startup of the device, screen 704 may display options for selecting a language, and screen 706 may provide for selecting whether the device is being used by a user or a clinician. Based on the clinician being selected, screen 708 may be displayed to provide instructions for entering the clinical mode.

Based on the user being selected, screens 710-716 may be displayed to provide information about and instructions for obtaining an application associated with the RPT device for use outside of the RPT device (e.g., on a smartphone). In Screen 716, the user may be provided with an option to setup the application or to skip setting up the application.

Figure 7C:
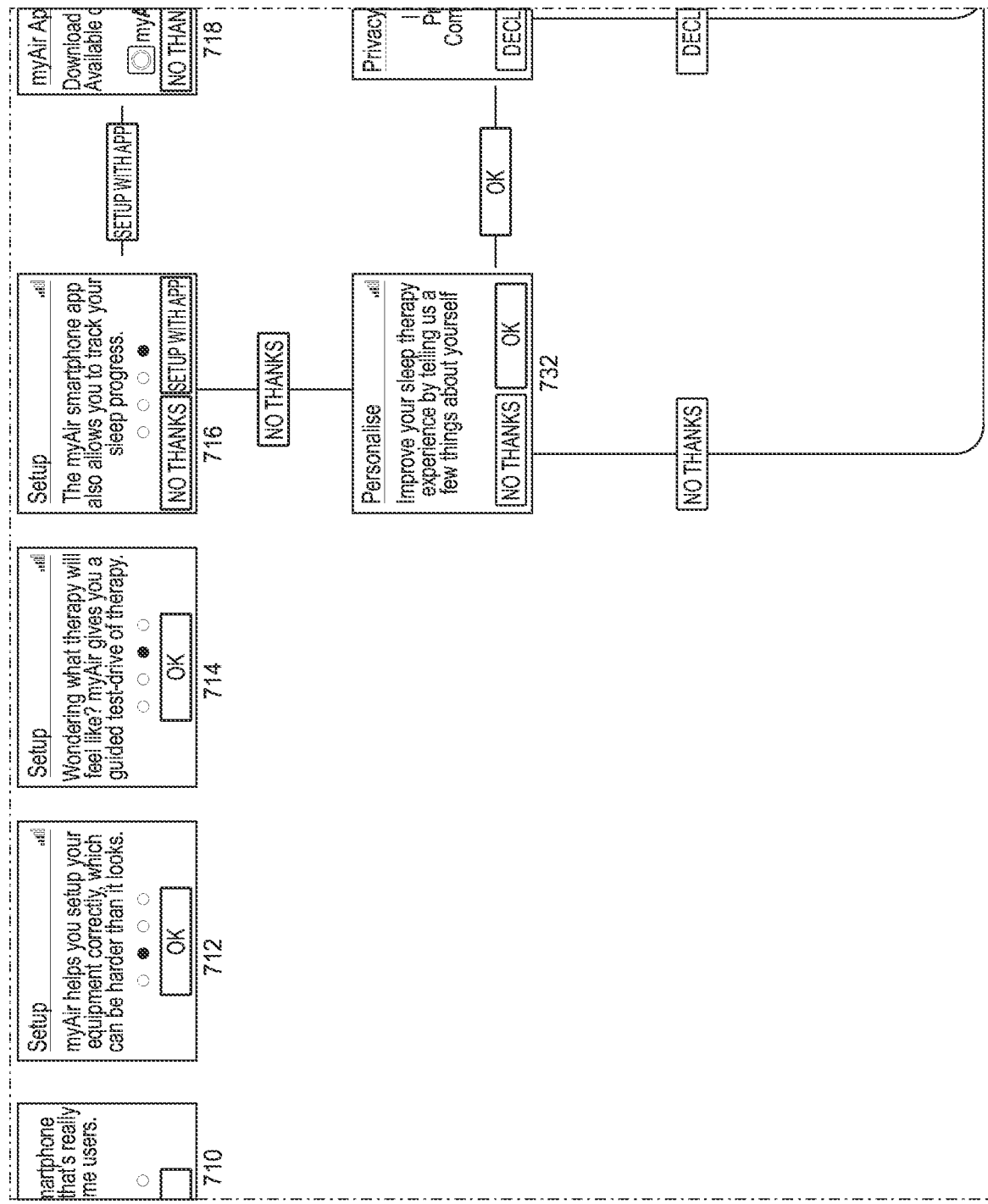
Figure 7D:
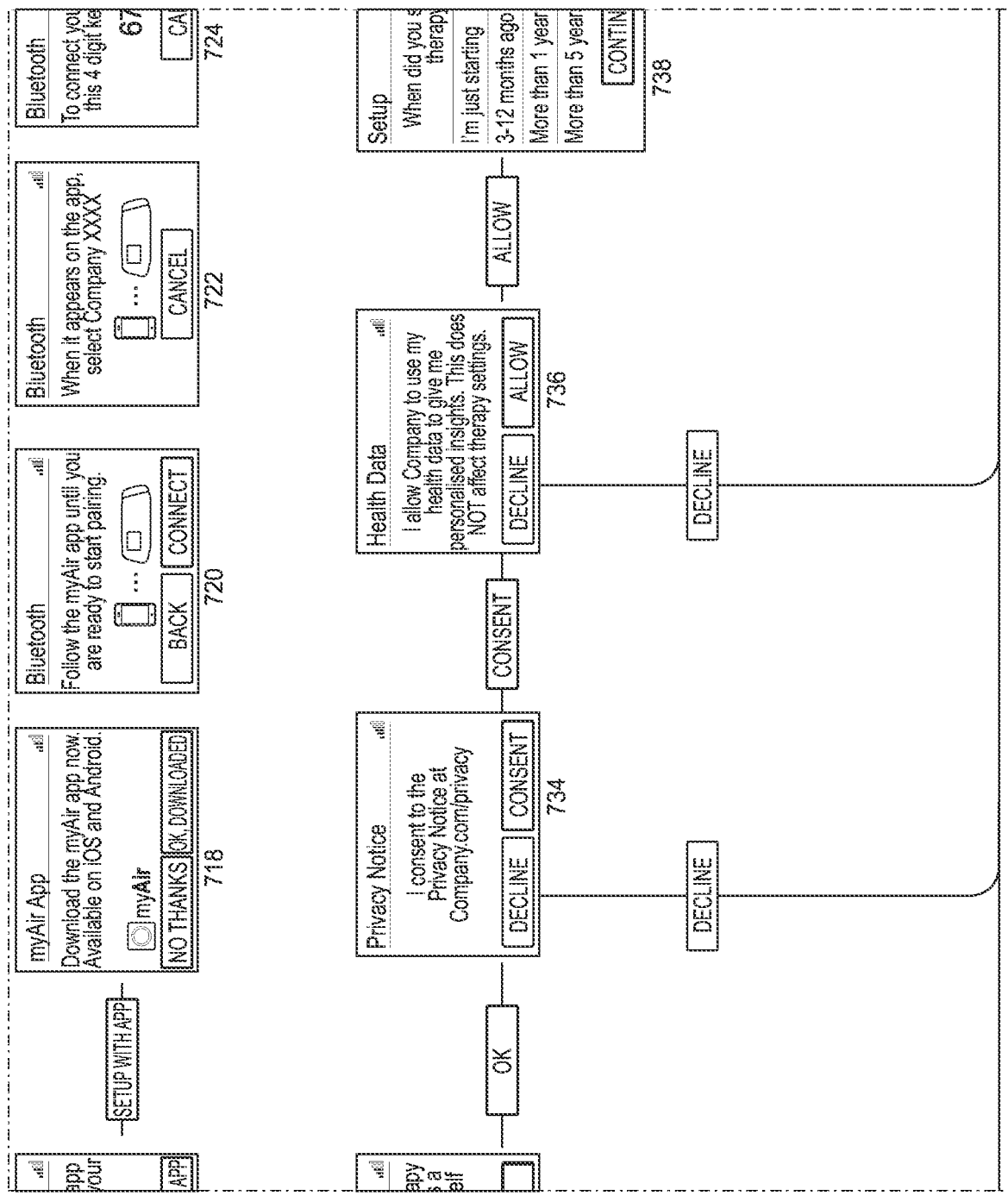
Figure 7E:
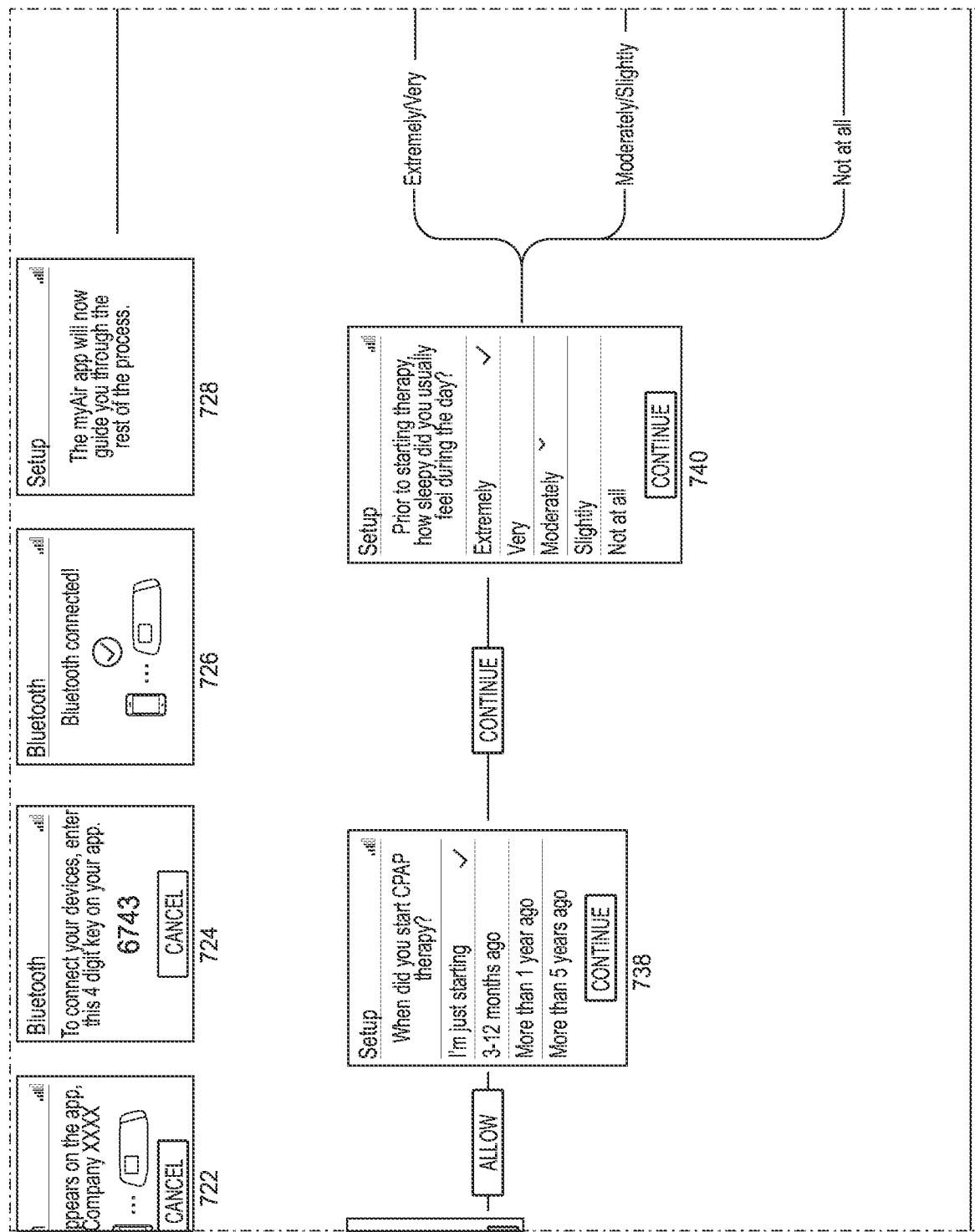
Figure 7F:
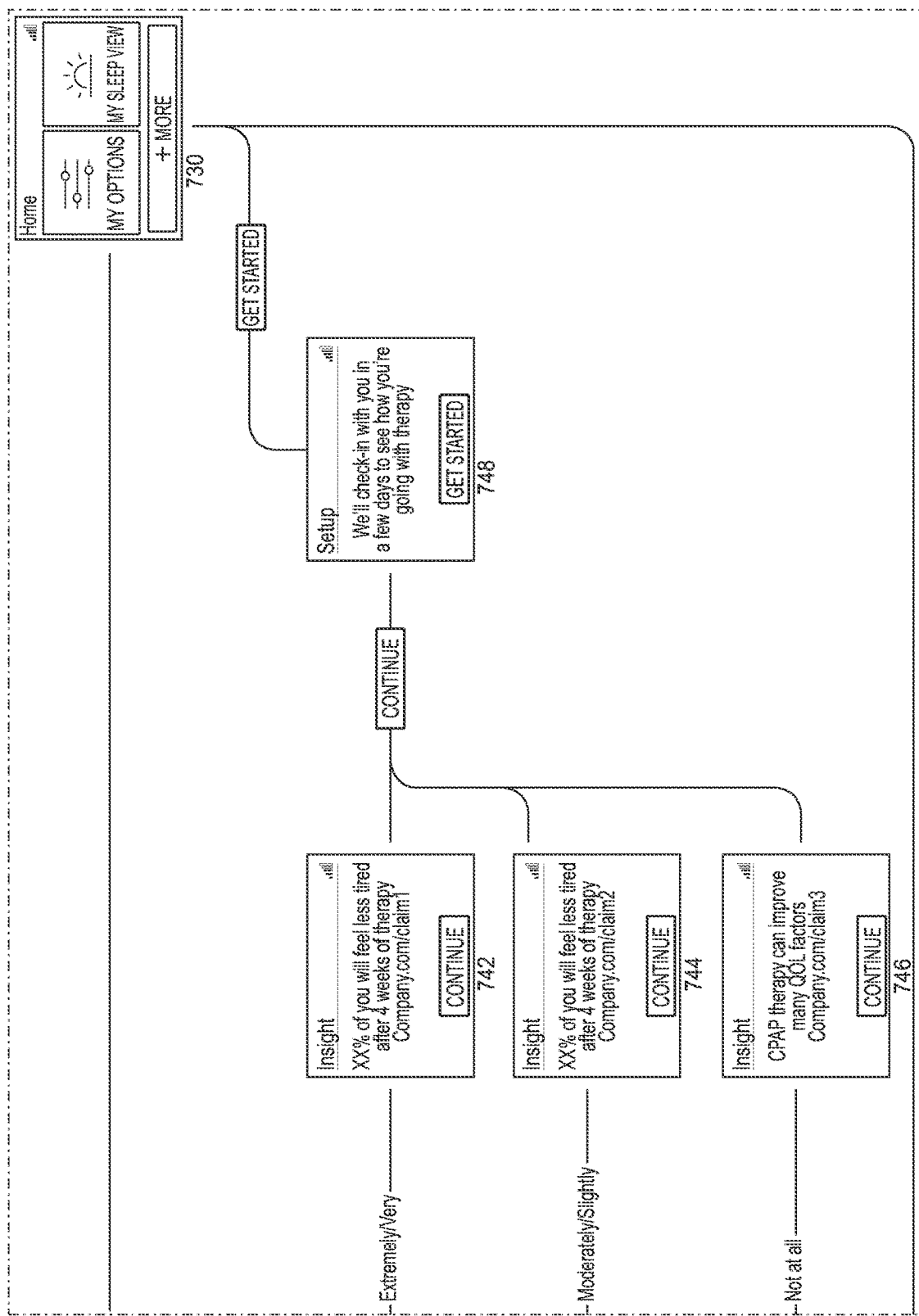

Based on the user selecting to setup the application (Setup With App in screen 716), screens 718-728 may be displayed to guide the user in setting up the application outside of the RPT device and connecting the RPT device to the external device executing the application. At screen 728, the user is provided with an indication that the remaining instructions will be provided through the application. Screen 730 in FIG. 7F is displayed at completion of providing the instructions to setup the application. Based on the user selecting to setup the application (Setup With App in screen 716), the RPT Device may disable the RPT device for requesting user feedback using the RPT device (e.g., when switching between screens 716 and 718.

Based on the user selecting not to setup the application (No thanks in Screen 716), screens 732-748 may be displayed for obtaining feedback from the user. If the application is installed on the external device, information in screens 732-748 may be displayed in the application.

In screen 732, the user is provided with an option to provide feedback. In response to selecting "OK", screens 734 and 736 are displayed to consent to privacy notice and/or sharing the user's health data, respectively. As shown in FIGS. 7C and 7D, a user may decline to provide feedback, consent and/or share health data.

Screen 738 shows the user being asked a first question of "When did you start CPAP therapy?". Screen 738 displays a plurality of selectable responses and a confirmation to continue with the feedback.

Screen 740 shows the user being asked a second question of "Prior to starting therapy how sleepy did you usually feel during the day?" and a plurality of selectable responses. The plurality of selectable responses include "Extremely", "Very", "Moderately", "Slightly", and "Not at all". As shown in FIGS. 7E and 7F, a different screen may be displayed with micro-coaching responses based on which of the responses is selected.

If the feedback response from the patient is "Extremely" or "Very" the RPT device may display screen 742 including an insight such as "X % of extremely or very sleepy users will feel less tired after 4 weeks of therapy". If the feedback response from the patient is "Moderately" or "Slightly" the RPT device may display screen 744 including an insight such as "X % of moderately or slightly sleepy users will feel less tired after 4 weeks of therapy". If the feedback response from the patient is "Not at all" the RPT device may display screen 746 including an insight such as "CPAP therapy can also improve many quality of life factors beyond sleepiness." Providing relevant insights in response to feedback can improve patient confidence, help them understand and better see the benefits of their therapy, and increase motivation to continue with therapy. While in screens 742-746, multiple responses may correspond to a same insight, in some examples of the present technology a different insight may be provided for each of the questions. For some questions and responses, a same insight may be provided for all of the responses.

After displaying the insight in screens 742-746, screen 748 may be displayed indicating that the system will check in with the user after a predetermine number of days to see how they are doing.

One or more additional questions with or without micro-coaching responses may be included in the workflow illustrated in FIGS. 7A-7F. For examples, questions shown in FIGS. 4G-4K and 6 may be included in the workflow illustrated in FIGS. 7A-7F. In one example, micro-coaching responses may be provided for each response provided to a question of a workflow.

FIGS. 8A-8E illustrate post-therapy flow, including questions and insights, as provided in the medical device, but which may also be provided outside of the medical device (e.g., application executing on a remote device and/or in browser). In some examples of the present technology, one or more of the screens shown in FIGS. 8A-8E may be displayed by the remote device and/or the browser. FIG. 8A illustrates an overview of the pre-therapy flow and FIGS. 8B-8E illustrate a detailed view of the portions of the overview shown in FIG. 8A. One or more of the screens shown in FIGS. 8A-8E may be optional and/or may be displayed in a different sequence, and/or may be combined and displayed simultaneously on a same screen.

Screen 802 shown a home screen of the RPT device, which may corresponds to screen 730 shown in FIG. 7F. Based on reaching predetermined days (e.g., days 3, 7, 14, 21, 28) and/or after expiration of a predetermined time period, screen 804 may be displayed requesting whether the user has time for a check-in. If the user selects "No Thanks" in screen 804, the user may return to the home screen 802. If the user selects "No Thanks" in screen 804 a predetermined number of times (e.g., 2 times), screen 806 may be displayed to determine whether the check in should be turned off. If the check-ins are turned in screen 806, the display of screen 804 may be disabled on the RPT device. In some examples, disabling the check-ins on the RPT device may still keep the check-ins enabled on the application associated with the RPT device. In other example, disabling the check-ins on the RPT device may disable the check-ins on the application.

Figure 8B:
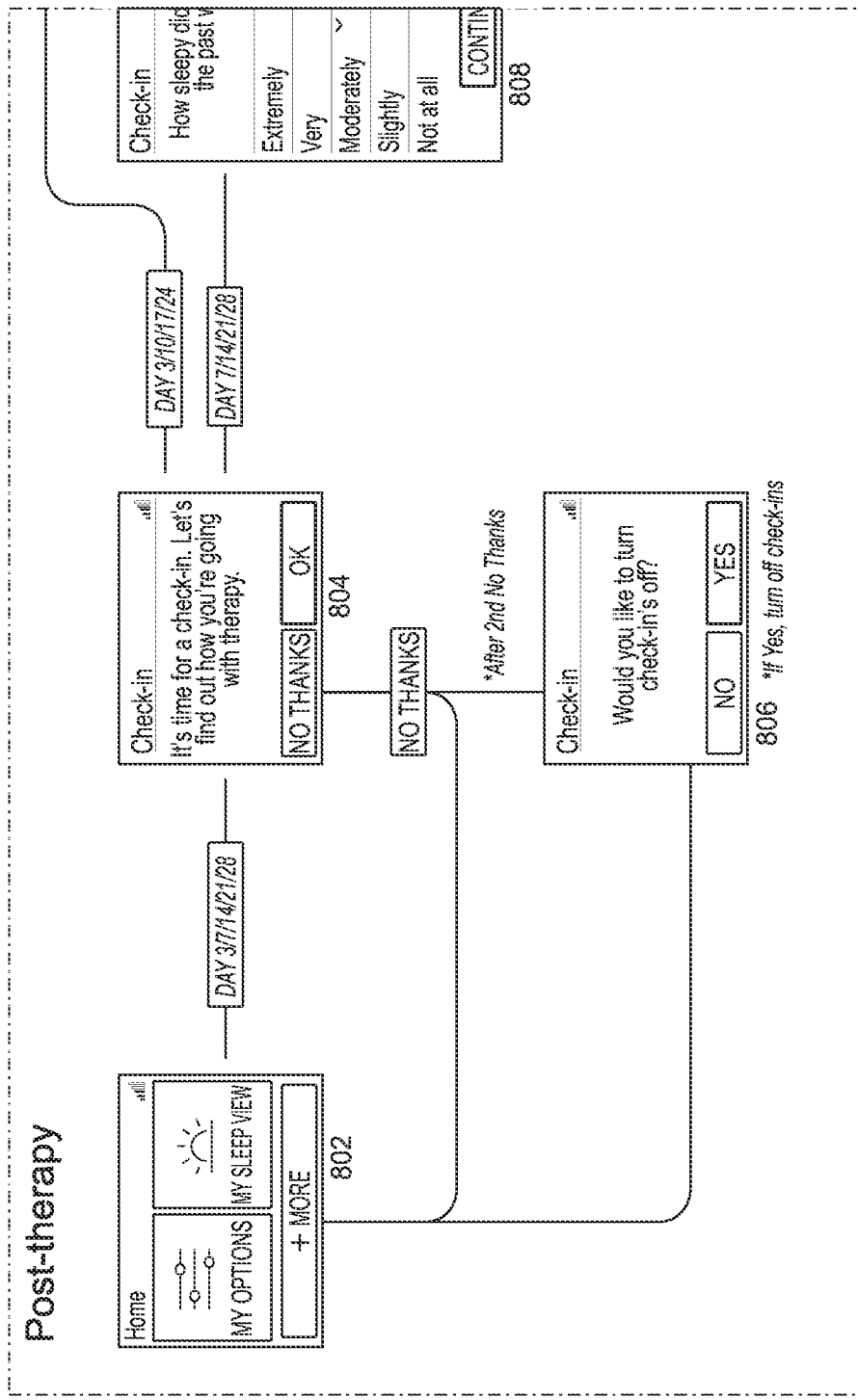
Figure 8C:
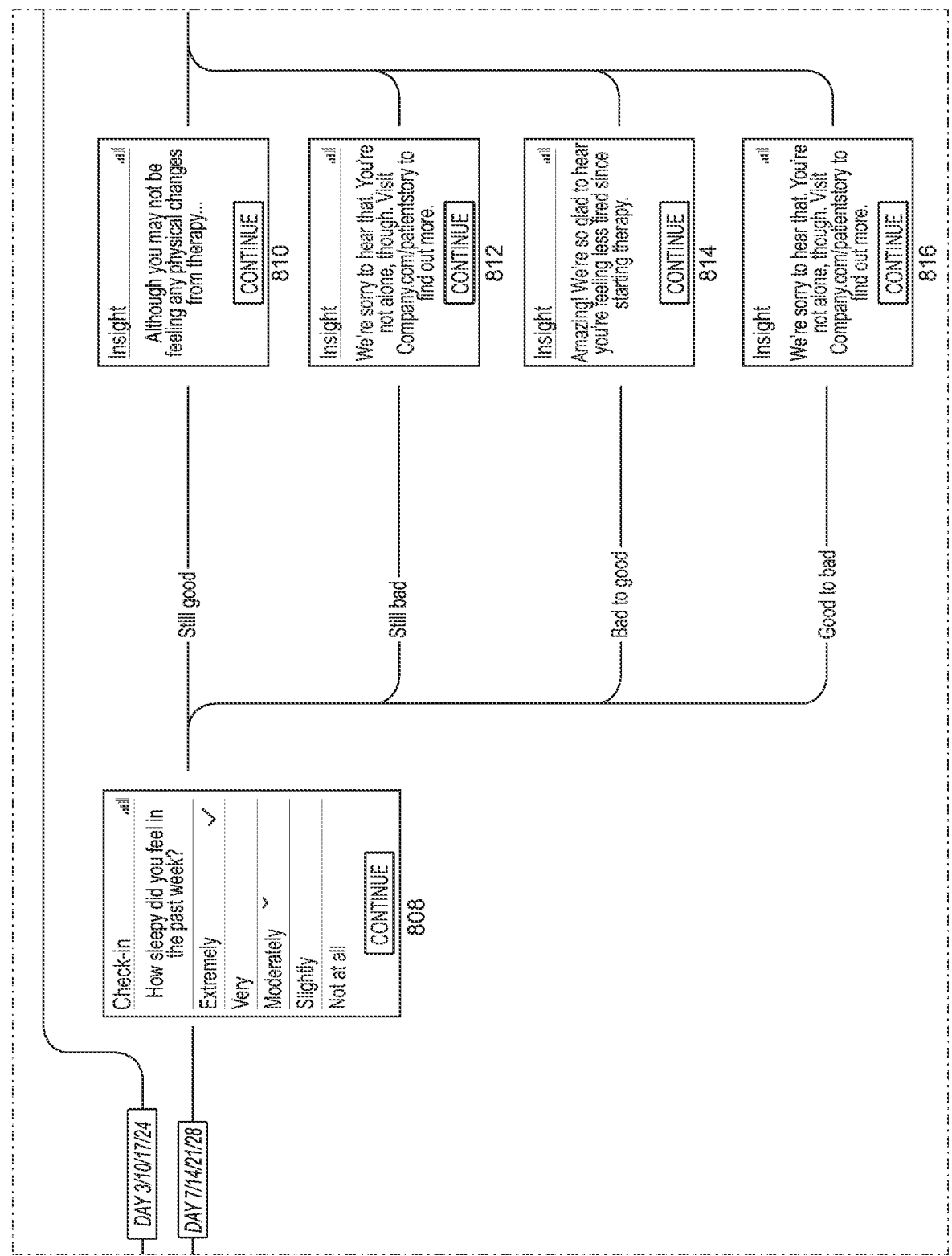
Figure 8D:
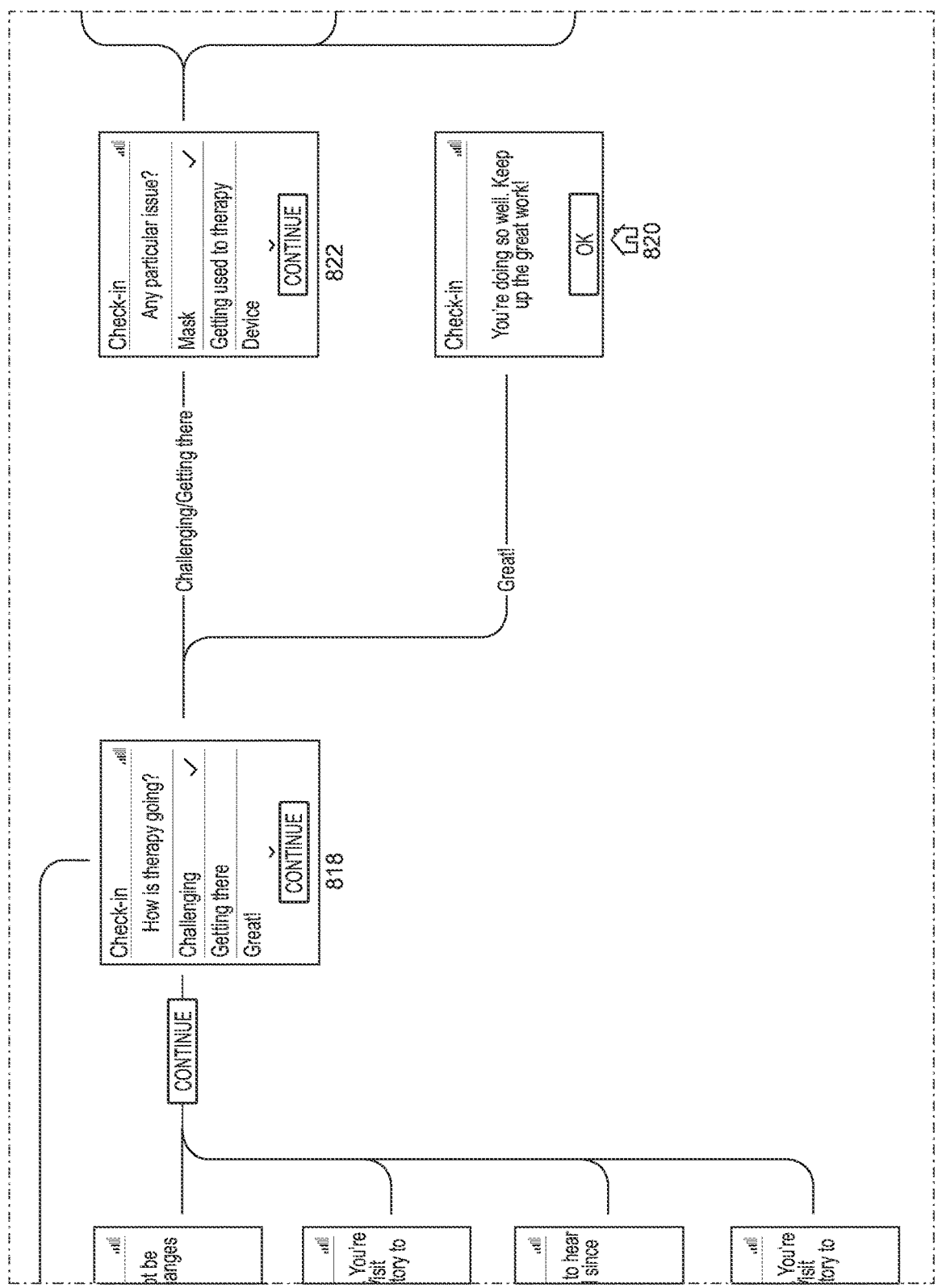

Based on the user selecting to perform a check-in, one or more questions can be displayed to the user. As shown in FIGS. 8B and 8C, different questions may be displayed depending on which day the check in is being performed. If the check in is on a first set of days (e.g., days 7, 14, 21, 28) one or more questions from a first set of questions may be displayed. If the check in is on a second set of days (e.g., days 3, 10, 17, 24) one or more questions from a second set of questions may be displayed. One or more questions in the first and second set of questions may be the same. In some examples, the number of questions displayed to the user on the first set of days may be larger than the number of questions displayed on the second set of days.

Screen 808 shows a first question that may be displayed on days 7, 14, 21 and 28. The first question may ask "How sleepy did you feel in the past week?" with an option to select an answer from one of "Extremely", "Very", "Moderately", "Slightly", and "Not at all". In response to each of the questions a different screen 810-816 may be displayed with micro-coaching responses (e.g., insights) and a selectable options to continue with the workflow.

Screen 818 may be displayed after the user selects to continue in one of the screens 810-816 or when asking questions on the second set of days. Screen 818 may include question "How is therapy going?" and a plurality of selectable responses. The selectable responses may include "Challenging", "Getting there" and "Great!". After selecting one of the response, the user may be provided with an option to continue to screens providing micro-coaching responses. Screen 820 may be displayed when "Great" is selected and screen 822 may be displayed when "Challenging" or "Getting there" is selected. Screen 820 may provide an encouragement and direct the user to the home screen 802 after the user selects "OK."

Screen 822 may display another questions asking the user to identify an area where the user is having issues. Screen 822 provided selectable options "Mask" "Getting used to therapy" and "Device." An option to continue is provided after the user makes a selection to one the issues.

In response to one of the selectable issues in screen 822, screens 824-830 may be displayed. In response to identifying a mask issue, screen 824 is displayed encouraging the user to us the application associated with the RPT device to help with mask fitting. In response to identifying an issue with getting used to therapy, screen 826 is displayed encouraging the user to us the application associated with the RPT device to help with adjusting the therapy. In response to identifying an issue with the device, screen 828 is displayed encouraging the user to us the application associated with the RPT device to help setup the equipment. Each of the screens 824-828 may include an option to try the app or no thanks, which may return the user to the home screen 802. When the user selects to try the application, screens for obtaining the application on an external device and connecting the application (e.g., screens 718-728) may be displayed on the RPT device.

Figure 8E:
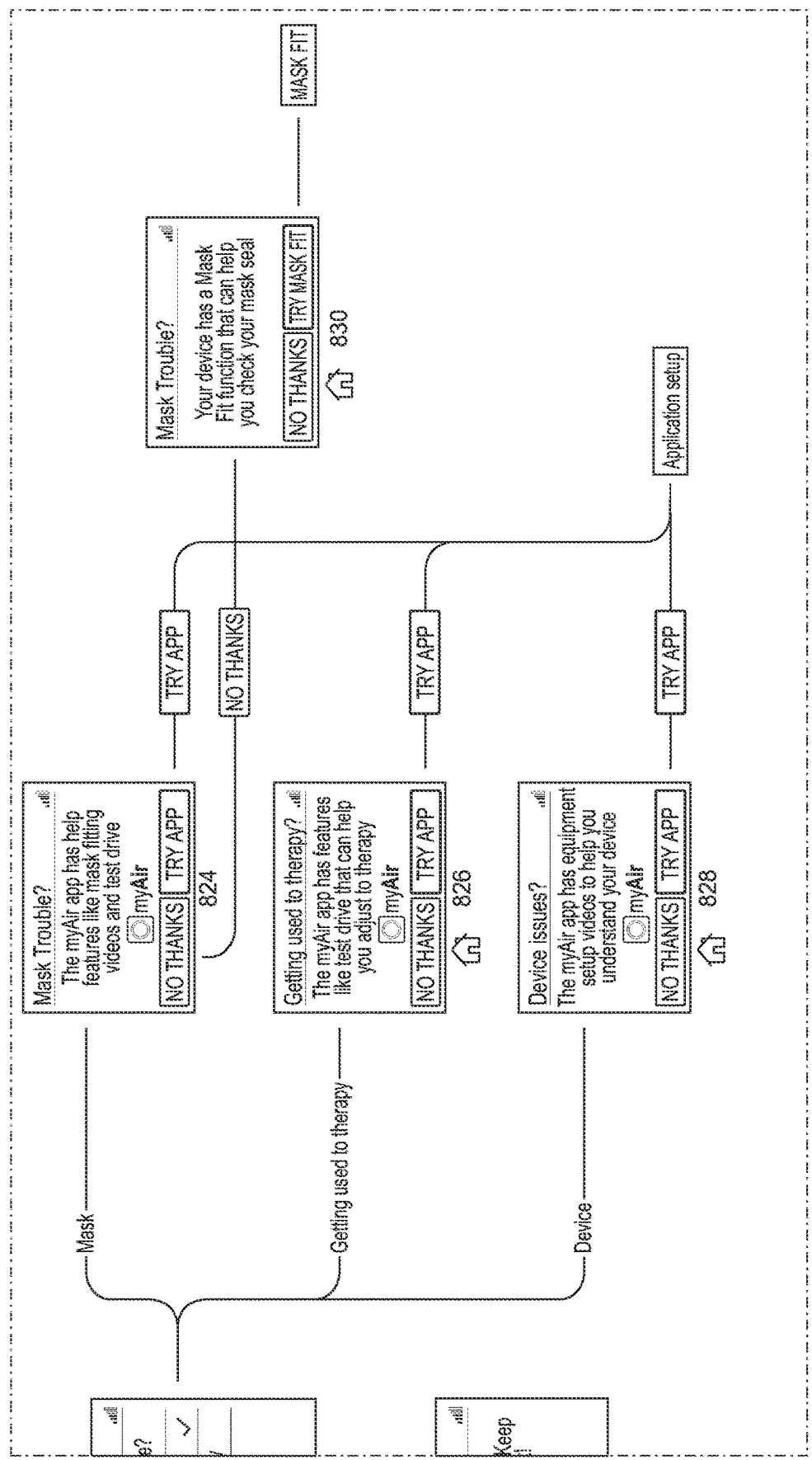

While screens 824-828 provide a user with an option to try the app, in some examples, screens 824-828 may include instructions for addressing the identified issue. As shown in FIG. 8E, when the user selects not to try the application, screen 830 may be displayed with an option for the RPT device to display instructions for checking the mask seal.

Examples of the present technology allow the HME to gain efficiencies in patient outreach and follow-up. Feedback from the patient questions and answers from the RPT device and/or user app may be combined with the users flow generator therapy data in the clinician portal to assist the HME's with an extra level of triaging and allow accurate follow-up targeting of the most impactful patient follow-ups. In some examples, the data may be provided via a web application view targeted at helping the HME increase their follow up efficiencies. This view may be integrated with provider portal software such that it appears as another page in portal.

FIGS. 9A-9D illustrate representative HME screens that may be displayed according to examples of the present technology.

FIG. 9A illustrates an example home view of patient groups/buckets. The patient feedback may be generated by the backend system (e.g., using information obtained via the patient portal) based on information received from a plurality of patients and/or medical devices associated with the patient and provided to the HME.

FIG. 9B illustrates an example of a user interface 900 providing a provider portal patient exception management feature. The information for the patient's exception management may be generated by the backend system based on information received from a plurality of patients, medical devices and/or applications associated with the patient and provided to the HME.

The user interface 900 may display information about a plurality of patients (Patients 1-8) for which information is received from the medical devices and/or application associated with the patients. The user interface 900 provides a summary for each patients which corresponds to one of the patient feedback groups/buckets shown in FIG. 9A. The user may be assigned to one of the patient feedback groups/ buckets based on the responses to questions received from the user and/or history of operating the RPT device. In one example, the user may be assigned to one of the patient feedback groups/buckets only based on the responses to questions received from the user. As shown in FIG. 9B, Patient 1 is assigned to "Challenging therapy" group/bucket and Patient 2 is assigned to "Continued sleepiness" group/ bucket. Each of the Patients 1-8 is assigned to one of the patient feedback groups/buckets shown in FIG. 9A.

In response to selecting one of the patient, a detailed view of the patient may be shown in the user interface 900. In FIG. 9B, in response to selecting Patient 1, the user interface 900 shows a detailed view of the Patient 1. The user interface shows the date of birth, patient ID, contact information, whether the user is registered with an application, HME location, and payor information for Patient 1. The user interface 900 may also show compliance of the user for a plurality of days and feedback received for one or more of the days. In response to selecting a day on which feedback was provided by the user, the responses provided by the user to questions may be displayed. For example, in FIG. 9B, selecting days 7/26 or 7/19 may provide details on feedback provided by Patient 1.

As shown in FIG. 9B, the interface includes an option to select information for a plurality of patients. Filtering options may be used to display patients satisfying the selected filters. The filters may include filtering based on therapy adherence, sleepiness trend, and/or feedback received from the user. The feedback received from the user may correspond to the responses received form the user in response to displayed questions.

The plurality of patients may include patients associated with the HME and patients not associated with the HME. Sensitive information for patients not associated with the HME may be hidden from the provider portal. The HME may use the information from the two groups of patients to compare performance (e.g., compliance) of their patients with other patients and identify areas where performance can be improved. In some examples, information about non associated patients may be provided in a statistical manner, without providing patient specific information.

FIG. 9C illustrates an example of a patient detail panel. As shown in FIG. 9C, sleepiness trend filter option is selected and from the patients satisfying this filter, a first patient (Patient 2) is selected to provide information specific to the selected patient. The patient feedback can be provided for a specific day on which the user provided feedback corresponding to the selected filter. In FIG. 9C, the day on which the patient selected that the daytime sleepiness is "Extreme" and that the therapy is "Going well" is shown. The patient feedback may also identify particular issues, any self-help attempted by the user, and/or whether the patient says using the device is helpful.

FIG. 9D illustrates an example of logic between selectable filtering options and characterizations assigned to the user based on the responses received from the user. In some examples of the present technology multiple filter groups may be provided in each of which a plurality of selectable filters are provided. One or more of the filters in each group may be selected. In some examples, a single filter may be selected in each group. As shown in FIG. 9D some filter groups may include filters having a one to one correspondence between the selectable filters and how the user is characterized. For example, each of the therapy adherences filters that are selectable by the user correspond to a respective therapy adherences that is applied to the user. Similarly, each of the Feedback—Failure filters with options that are selectable by the user correspond to a respective Feedback— Failure with that is applied to the user. Other filter groups may include a plurality of selectable filter options grouped into a single characterization of the user. For example, in FIG. 9D, the selectable filter options "Extreme" and "Very High" under Daytime sleepiness may correspond to the user's daytime sleepiness being characterized as "High." The selectable filter options "Moderate", "Slight" and "Not at all" may correspond to the user's daytime sleepiness being characterized as "Low."

FIGS. 10A and 10B illustrate examples of an interface 950 providing information about a plurality of patients. The displayed information may include range over which data is available (number of days), patient compliance or noncompliance, and when information was last updated for each patient. One or more filters may be selected to filter the plurality of patients for which information is displayed. As shown in FIG. 10B, compliance or non-compliance may be shown on a daily basis with options to generate and/or transmit questions to the patient (e.g., via the medical device and/or application executed on a mobile devices linked to the medical device). The questions may be pre-stored or generated by the user in real time. The questions may include "How the patient feels about their therapy?", what problems they faced with (i.e. Mask, Machine etc. . . . ).

In some examples, micro-coaching responses (e.g. insights, encouragement, identification of helpful resources, etc. . . . ) to selected response may be pre-stored or generated by the user in real time. In response to selecting a patient (e.g., Patient 3 in FIG. 10B), the interface 950 may display questions and responses presented to the patient. In response to selecting view all feedback, the responses received from the patient may be displayed. The interface may provide for the patients displayed to the user to be filtered by user name, location, status, notification and/or therapy mode.

FIGS. 11A and 11B illustrate additional examples of an interface 980 providing information about a plurality of patients. The interface includes a view of wireless and all patients and drop down menu (new page) screens—with specific feedback content. In FIG. 11A, feedback including questions and responses presented or scheduled to be presented to the Patient 4 are displayed in the interface 980 in response to selecting feedback icon for Patient 4. The responses to the questions entered by the patient may be displayed by selecting "View all feedback." In FIG. 11B, feedback including questions and responses presented or scheduled to be presented to the Patient 3 are displayed in the interface 980 in response to selecting feedback icon for Patient 3. The responses to the questions entered by the patient may be displayed by selecting "View all feedback."

In some examples, the information about the patient may be used by the user during their conversations with the patient (remotely or in person). The conversation may be performed via an option provided on the medical device or an application executing on a mobile devices. In some examples, the interface may provide an option to contact and start a conversation with the patient.

In some examples, the information may be collected from the patient (automatically or via displayed questions) at predetermined intervals or specific days. For example, the data may be collected on days 3, 7, 14, 21, and 28, but is not so limited. In some examples, the days to collect the data may be pre-set (e.g., to days 3, 7, 14, 21, and 28) such that a plurality of medical devices provide the data at the same intervals and/or days, providing an appropriate frequency and days for most HME's. Same durations and/or days for collecting data may allow for better comparison of data from the plurality of patients.

The information provided in the interface (e.g., information about the patient, device, device use and patient feedback) may be used to evaluate how the medical device and/or accessories (e.g., specific masks) are used and/or effectiveness of therapies and/or medical device accessories. This information can be used to make modifications to medical devices, accessories, therapies and/or patient training. As an example, the interface may share patient reported sleepiness information that has been collecting via user app with the HME (e.g., collected on days 3, 7, 14, 21, 28). The sleepiness information and/or other information may provide a new opportunity to better understand the patient and improve patient treatment efficacy, compliance and adherence.

The feedback data points (e.g., from interface shown in FIGS. 10A-11B) provided in the HME portal may support additional insight and further improve the user feedback module's efficacy in helping HME's (or clinicians) help patients achieve compliance and long term adherence. For example, patients who report they are still sleepy after weeks of therapy may show worse compliance and long term adherence than those who are feeling less sleepy). The insight may show, for example, what portion of the patients don't feel less tired after a couple of weeks of therapy and that these patients suffer worse compliance and higher dropout rate in longer term.

In some examples of the present technology, the user interfaces of FIGS. 9B, 9C, 10A, 10B, 11A and/or 11B may be provided by and/or operations performed in relation to the features shown in the user interfaces of FIGS. 9B, 9C, 10A, 10B, 11A and/or 11B may be implemented by an external device 4286, a server 6030 and/or a cloud computing platform 6040.

The external device 4286, a server 6030 and/or a cloud computing platform 6040 may include communication circuitry configured to communicate with a plurality of respiratory pressure therapy devices 4000, 6062 and 6064 and other devices (e.g., local external device 4288) executing applications associated with the plurality of respiratory pressure therapy devices, and a processing system including memory and at least one hardware processor coupled to the communication circuitry. The processing system may, for example, control a display to display the user interface shown in FIGS. 9B, 9C, 10A, 10B, 11A and/or 11B. The processing system may also receive information from the respiratory pressure therapy devices and/or applications associated with the respiratory pressure therapy devices (e.g., patient information, respiratory pressure therapy device use history and responses to questions) to be displayed in the user interfaces. The user interface may display a list of patients associated with the plurality of respiratory pressure therapy devices and the applications, and selectable filters for filtering patients displayed in the list. The displayed list of patients may be filtered in response to selecting one or more filters. In response to receiving a selection of a patient in the list of patients or filtered lists, information about use of the respiratory pressure therapy devices by the selected patient may be displayed.

In some examples, the processing system may transmit information to the respiratory pressure therapy devices and/or applications associated with the respiratory pressure therapy devices. The transmitted information may include, questions, responses to questions, personalized therapy and/or coaching information. As discussed above, the transmitted information may be transmitted in real time in response to responses received from the patient. The transmitted information may be generated by a user and/or automatically (e.g., based on preset settings, advanced analytics, artificial intelligence, and/or machine learning).

Examples of the present technology may be implemented in an on-demand cloud computing platform, that can be configured to perform machine learning using data received from a plurality of patients/medical devices. The cloud computing system may be an AMAZON WEB SERVICES (AWS), MICROSOFT AZURE, GOOGLE CLOUD, IBM CLOUD, ORACLE CLOUD or another cloud computing service.

In one form of the present technology, a memory one or more of the devices shown in FIG. 4G may act as a non-transitory computer readable storage medium on which is stored computer program instructions expressing the one or more methodologies described herein. As used herein, the term "non-transitory computer-readable storage medium" includes a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or Blu-Ray Disc, or other type of device for non-transitory electronic data storage. The term "non-transitory computer-readable storage medium" does not include a transitory, propagating electromagnetic signal.

5.7.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.8 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

According to one arrangement, the reservoir 5110 comprises a conductive portion 5120 configured to allow efficient transfer of heat from the heating element 5240 to the volume of liquid in the reservoir 5110, a humidifier reservoir dock 5130 (as shown in FIG. 5B) configured to receive the humidifier reservoir 5110 with a locking lever 5135 configured to retain the reservoir 5110 and/or a water level indicator 5150 (as shown in FIGS. 5A-5B), and/or one or more humidifier transducers (sensors) 5210 instead of, or in addition to, transducers 4270 described above. The humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

Examples of the humidifier components are described in PCT application PCT/AU2014/050426 (WO2015089582), which is incorporated herein by reference.

5.9 Respiratory Pressure Therapy Modes

Various respiratory pressure therapy modes may be implemented by the RPT device 4000 depending on the values of the parameters A and P0 in the treatment pressure equation $Pt=A\Pi(\Phi, t)+P_0$ used by the therapy parameter determination algorithm 4329 in one form of the present technology.

5.9.1 CPAP Therapy

In some implementations of this form of the present technology, the amplitude A is identically zero, so the treatment pressure Pt is identically equal to the base pressure $P_0$ throughout the respiratory cycle. Such implementations are generally grouped under the heading of CPAP therapy. In such implementations, there is no need for the therapy engine module 4320 to determine phase Φ or the waveform template Π(Φ). At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$–Pmin, so that the decrease in $P_0$ to the minimum treatment pressure Pmin in the absence of any detected events is exponential. In one implementation, the constant of proportionality is set such that the time constant τ of the exponential decrease of $P_0$ is 60 minutes, and the minimum treatment pressure Pmin is 4 cmH$_2$O. In other implementations, the time constant τ could be as low as 1 minute and as high as 300 minutes, or as low as 5 minutes and as high as 180 minutes. In other implementations, the minimum treatment pressure Pmin can be as low as 0 cmH$_2$O and as high as 8 cmH$_2$O, or as low as 2 cmH$_2$O and as high as 6 cmH$_2$O. Alternatively, the decrement in $P_0$ could be predetermined, so the decrease in $P_0$ to the minimum treatment pressure Pmin in the absence of any detected events is linear.

5.9.2 Bi-Level Therapy

In other implementations of this form of the present technology, the value of amplitude A in equation $Pt=A\Pi(\Phi, t)+P_0$ may be positive. Such implementations are known as bi-level therapy, because in determining the treatment pressure Pt using equation $Pt=A\Pi(\Phi, t)+P_0$ with positive amplitude A, the therapy parameter determination algorithm 4329 oscillates the treatment pressure Pt between two values or levels in synchrony with the spontaneous respiratory effort of the patient 1000. That is, based on the typical waveform templates Π(Φ, t) described above, the therapy parameter determination algorithm 4329 increases the treatment pressure Pt to P0+A (known as the IPAP) at the start of, or during, or inspiration and decreases the treatment pressure Pt to the base pressure P0 (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH$_2$O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation $Pt=A\Pi(\Phi, t)+P_0$ to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A=G\int(Vent-Vtgt)dt \qquad (1)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure $P_0$. As with the base pressure $P_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure $P_0$ in constant CPAP therapy.

Alternatively, the therapy parameter determination algorithm 4329 may repeatedly compute the base pressure $P_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.10 Glossary

For the purposes of the present technology disclosure, in certain forms of the present technology, one or more of the following definitions may apply. In other forms of the present technology, alternative definitions may apply.

5.10.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.10.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
 (i) Flattened: Having a rise followed by a relatively flat portion, followed by a fall.
 (ii) M-shaped: Having two local peaks, one at the leading edge, and one at the trailing edge, and a relatively flat portion between the two peaks.
 (iii) Chair-shaped: Having a single local peak, the peak being at the leading edge, followed by a relatively flat portion.
 (iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
 (i) a 30% reduction in patient breathing for at least 10 seconds plus an associated 4% desaturation; or
 (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.11 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.12 REFERENCE SIGNS LIST

| | |
|---|---|
| screen | 602 |
| screen | 604 |
| screen | 606 |
| screen | 608 |
| screen | 610 |
| screen | 612 |
| screen | 614 |
| screen | 616 |
| screen | 702 |
| screen | 704 |
| screen | 706 |
| screen | 708 |
| screen | 710 |
| screen | 712 |
| screen | 714 |
| screen | 716 |
| screen | 718 |
| screen | 720 |
| screen | 722 |
| screen | 724 |
| screen | 726 |
| screen | 728 |
| home screen | 730 |
| screen | 732 |
| screen | 734 |
| screen | 736 |
| screen | 738 |
| screen | 740 |
| screen | 742 |
| screen | 744 |
| screen | 746 |
| screen | 748 |
| home screen | 802 |
| screen | 804 |
| screen | 806 |
| screen | 808 |
| screen | 810 |
| screen | 812 |
| screen | 814 |
| screen | 816 |
| screen | 818 |
| screen | 820 |
| screen | 822 |
| screen | 824 |
| screen | 826 |
| screen | 828 |
| screen | 830 |
| user interface | 900 |
| interface | 950 |
| interface | 980 |
| patient | 1000 |
| other patient | 1002 |
| other patient | 1004 |
| bed partner | 1100 |
| patient interface | 3000 |
| RPT device | 4000 |
| external housing | 4010 |
| upper portion | 4012 |
| portion | 4014 |
| panel(s) | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| air circuit | 4171 |
| supplemental oxygen | 4180 |
| electrical components | 4200 |
| Single Printed Circuit Board Assembly | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow sensor | 4274 |
| speed sensor | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre-processing module | 4310 |
| pressure compensation algorithm | 4312 |
| vent flow rate estimation | 4314 |
| leak flow rate estimation | 4316 |
| leak flow rate estimation | 4316 |
| respiratory flow rate estimation | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| snore determination algorithm | 4326 |
| snore determination algorithms | 4326 |
| airway patency determination algorithm | 4327 |
| target ventilation determination algorithm | 4328 |
| therapy parameter determination algorithm | 4329 |
| therapy control module | 4330 |
| algorithm | 4340 |
| method | 4500 |
| step | 4520 |
| step | 4560 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| humidifier transducer | 5210 |
| pressure transducers | 5212 |
| flow rate transducers | 5214 |
| temperature transducers | 5216 |
| humidity sensor | 5218 |
| heating element | 5240 |
| humidifier controller | 5250 |
| central humidifier controller | 5251 |
| heating element controller | 5252 |
| air circuit controller | 5254 |
| remote external device | 5286 |
| communication link | 6020 |
| server | 6030 |
| cloud computing platform | 6040 |
| medical devices | 6062 |
| medical devices | 6064 |
| setup step | 7010 |
| step | 7012 |
| step | 7014 |
| step | 7016 |
| step | 7018 |
| step | 7020 |
| step | 7022 |
| step | 7024 |
| step | 7026 |
| step | 7028 |

-continued

| 5.12 REFERENCE SIGNS LIST | |
| --- | --- |
| step | 7030 |
| step | 7032 |
| step | 7034 |
| step | 7036 |
| display screen | 7050 |
| display screen | 7052 |
| display screen | 7054 |
| display screen | 7056 |
| display screen | 7058 |
| display screen | 7060 |
| display screen | 7062 |
| display screen | 7064 |
| patient survey service | 8010 |
| patient survey service | 8020 |
| MCS device | 8024 |
| patient portal | 8030 |

The invention claimed is:

1. A respiratory pressure therapy system for providing continuous positive air pressure (CPAP) to a patient, the respiratory pressure therapy system comprising:
 a flow generator configured to generate a supply of breathable gas for delivery to the patient, wherein the breathable gas is output from the flow generator at a pressure level that is above atmospheric pressure;
 at least one sensor that is configured to measure a physical quantity while the breathable gas is supplied to the patient;
 a computing device including memory and at least one hardware processor, the computing device configured to control the respiratory pressure therapy system to:
  before initial use of the respiratory pressure therapy system to provide a therapy to the patient:
   display, on a display device, one or more demographic questions relating to demographic information of the patient and a plurality of selectable responses to the one or more demographic questions;
   responsive to displaying the one or more questions, receive one or more inputs selecting of one or more of the selectable responses to the one or more demographic questions;
   display, on the display device, a first question relating to subjective feedback from the patient and a plurality of selectable responses to the first question;
   responsive to displaying the first question, receive a first input selecting one of the selectable responses to the first question; and
   in response to receiving the first input, display a first coaching response from among a plurality of coaching responses corresponding to the selected response to the first question, wherein each of the selectable responses to the first question relating to subjective feedback corresponds to a different coaching response from among the plurality of coaching responses; and
  during use of the respiratory pressure therapy system to provide therapy to the patient:
   receive, from the at least one sensor, sensor data that is based on measured physical property of the supply of breathable gas; and
   control, based on the received sensor data and the inputs selecting one or more of the selectable responses to the one or more demographic questions, the flow generator to adjust a property of the supply of breathable gas that is delivered to the patient.

2. The respiratory pressure therapy system of claim 1, wherein the computing device is further configured to control the respiratory pressure therapy system to:
 after displaying the first coaching response, transmit the selected response to the first question to a remote processing system in response to receiving a second input to continue;
 receive, from the remote processing system, settings for the respiratory pressure therapy system; and
 adjust, based on the received settings, control settings of the respiratory pressure therapy system.

3. The respiratory pressure therapy system of claim 2, wherein the plurality of coaching responses corresponding to the plurality of selectable responses are received from the remote processing system.

4. The respiratory pressure therapy system of claim 2, wherein the computing device is further configured to control the respiratory pressure therapy system to: display a second coaching response corresponding to the selected response to the first question in response to receiving the second input to continue.

5. The respiratory pressure therapy system of claim 4, wherein displaying the second coaching response includes displaying a plurality of selectable options, each of the selectable options corresponding to resolving a different issue in using the respiratory pressure therapy system.

6. The respiratory pressure therapy system of claim 5, wherein the plurality of selectable options include using an application associated with the respiratory pressure therapy system to guide a user of the respiratory pressure therapy system in resolving the issue in using the respiratory pressure therapy system.

7. The respiratory pressure therapy system of claim 6, wherein the computing device is further configured to control the respiratory pressure therapy system to: display, after receiving the second input to continue, a second question relating to subjective feedback and a plurality of selectable responses to the second question;
 responsive to displaying the second question, receive a third input selecting one of the selectable responses to the second question;
 display a third coaching response corresponding to the selected response to the second question in response to receiving the third input to continue; and
 after displaying the third coaching response, transmit the selected response to the second question to the remote processing system in response to receiving a fourth input to continue.

8. The respiratory pressure therapy system of claim 2, wherein the computing device is further configured to control the respiratory pressure therapy system to:
 receive, from a system associated with a clinician, additional settings for the respiratory pressure therapy system determined based on the transmitted response to the first question.

9. The respiratory pressure therapy system of claim 8, wherein the system associated with the clinician is an on-demand cloud computing platform configured to perform machine learning using data received from a plurality of patients.

10. The respiratory pressure therapy system of claim 8, further comprising the system associated with the clinician and the system associated with the clinician is configured to determine tailored coaching programs for the patient based on responses to questions transmitted to the remote processing system from the computing device.

11. The respiratory pressure therapy system of claim 8 further comprising the system associated with the clinician and the system associated with the clinician is configured to determine personalized therapy for the patient based on responses to questions transmitted to the remote processing system from the computing device.

12. The respiratory pressure therapy system of claim 1, wherein the plurality of coaching responses corresponding to the plurality of selectable responses are stored in the memory.

13. The respiratory pressure therapy system of claim 1, wherein the first coaching response includes insights and/or encouragement to a user of the respiratory pressure therapy system.

14. The respiratory pressure therapy system of claim 1, wherein the first question is related to how well therapy provided by the respiratory pressure therapy system is going for a user of the respiratory pressure therapy system.

15. The respiratory pressure therapy system of claim 1, wherein the first question and the plurality of selectable responses to the first question are displayed at predetermined intervals of time.

16. The respiratory pressure therapy system of claim 15, wherein the first question and the plurality of selectable responses to the first question are displayed to a user of the respiratory pressure therapy system when the respiratory pressure therapy system is first used by the user.

17. The respiratory pressure therapy system of claim 1, wherein the first question and the plurality of selectable responses to the first question are displayed to a user of the respiratory pressure therapy system on predetermined days from when the user started using the respiratory pressure therapy system.

18. The respiratory pressure therapy system of claim 1, further comprising a patient interface configured to engage with at least one airway of the patient and supply breathable gas to the patient.

19. The respiratory pressure therapy system of claim 1, wherein the first question includes a question relating to subjective feedback from the patient about using the respiratory pressure therapy system.

20. The respiratory pressure therapy system of claim 1, further comprising a remote processing system and the remote processing system is configured to determine tailored coaching programs for the patient based on responses to questions transmitted to the remote processing system from the computing device.

21. The respiratory pressure therapy system of claim 1, wherein settings for the respiratory pressure therapy system and/or tailored coaching programs are received by an application, website, email, and/or a mobile device associated with the patient.

22. An apparatus for treating a respiratory disorder in a patient, the apparatus comprising:
a display;
a pressure generator configured to generate a flow of air for treating the respiratory disorder;
a transducer configured to generate a flow signal representing a property of the flow of air;
a controller, coupled to the display, the pressure generator, and the transducer, the controller configured to:
before initial use of the apparatus to provide therapy to the patient;
control the display to display a first question relating to subjective feedback from the patient and a plurality of selectable responses to the first question;
responsive to displaying the first question, receive a first input selecting one of the selectable responses to the first question; and
after receiving the first input, display a first coaching response from among a plurality of coaching responses corresponding to the selected response to the first question and transmit information about the selected response to the first question to a remote processing system, wherein each of the selectable responses to the first question relating to subjective feedback corresponds to a different coaching response from among the plurality of coaching responses; and
during use of the apparatus to provide therapy to the patient;
receive the flow signal from the transducer; and
based on the received flow signal, control the pressure generator to adjust a property of the flow air.

23. The apparatus of claim 22, wherein the controller is further configured to:
receive, from the remote processing system, further coaching responses; and
control the display to display the further coaching responses.

24. The apparatus of claim 23, wherein the controller is further configured to receive, from the remote processing system questions for the patient and a plurality of selectable responses for each question.

25. The apparatus of claim 23, wherein the further coaching responses include instructions for using the apparatus.

26. The apparatus of claim 23, wherein the further coaching responses include a personalized therapy for the patient.

27. The apparatus of claim 22, wherein the controller is further configured to:
receive, from the remote processing system, analysis results determined based on the transmitted response to the first question; and
adjust, based on the received analysis results, control settings of the apparatus.

28. The apparatus of claim 27, wherein the controller is configured to transmit operational data of the apparatus to the remote processing system, and the analysis results are determined based on the subjective feedback and the operational data of the apparatus.

29. The apparatus of claim 27, wherein the analysis results include tailored coaching program for the patient.

* * * * *